US007812712B2

(12) United States Patent
White et al.

(10) Patent No.: US 7,812,712 B2
(45) Date of Patent: Oct. 12, 2010

(54) METHOD AND SYSTEM FOR CONTROLLING A VEHICLE GIVEN TO A THIRD PARTY

(75) Inventors: Steve White, La Quinta, CA (US); Michael Dorin, Bedford, MA (US); John Noto, Ayer, MA (US)

(73) Assignee: All Protect, LLC, La Quinta, CA (US)

( * ) Notice: Subject to any disclaimer, the term of this patent is extended or adjusted under 35 U.S.C. 154(b) by 403 days.

(21) Appl. No.: 11/702,795

(22) Filed: Feb. 5, 2007

(65) Prior Publication Data
US 2007/0200663 A1 Aug. 30, 2007

Related U.S. Application Data

(60) Provisional application No. 60/773,141, filed on Feb. 13, 2006, provisional application No. 60/789,822, filed on Apr. 5, 2006.

(51) Int. Cl.
*B60R 25/10* (2006.01)
(52) U.S. Cl. .................. 340/426.2; 180/272; 180/287
(58) Field of Classification Search .............. 340/426.2, 340/576; 180/272, 287; 713/186
See application file for complete search history.

(56) References Cited

U.S. PATENT DOCUMENTS

| | | | | |
|---|---|---|---|---|
| 3,824,538 A | * | 7/1974 | Slemp | 180/272 |
| 5,081,667 A | * | 1/1992 | Drori et al. | 340/426.2 |
| 5,191,215 A | * | 3/1993 | McClelland et al. | 356/326 |
| 5,361,758 A | | 11/1994 | Hall et al. | |
| 5,429,128 A | | 7/1995 | Cadell et al. | |
| 5,515,847 A | | 5/1996 | Braig et al. | |

(Continued)

FOREIGN PATENT DOCUMENTS

FR 2 801 262 A1 5/2001

(Continued)

OTHER PUBLICATIONS

Ghionea, Simon; "Ethanol Sensing for Detecting Blood Alcohol Concentration," ECE499 Paper, Winter 2006, 18 pgs.

(Continued)

*Primary Examiner*—John A Tweel, Jr.
(74) *Attorney, Agent, or Firm*—Christie, Parker & Hale, LLP

(57) ABSTRACT

A method and system for controlling a vehicle given to a third party. The system includes a system controller; a mode-indicating device coupled to the system controller; and an authenticator coupled to the system controller. Here, the system controller is adapted to communicate a driving restriction to the vehicle upon an activation of the mode-indicating device by an authorized driver and until a deactivation of the mode-indicating device by the authorized driver, the system controller is adapted to restrict the activation and the deactivation of the mode-indicating device unless the authorized driver has been authenticated by the authenticator, and the driving restriction includes a limit selected from the group consisting of a limit in number of starts, a limit in speed, a limit in acceleration, a limit in number of minutes, a limit in distance, a limit in gears, a limit in locations, and combinations thereof.

39 Claims, 41 Drawing Sheets
(13 of 41 Drawing Sheet(s) Filed in Color)

U.S. PATENT DOCUMENTS

| | | | |
|---|---|---|---|
| 5,743,349 A | | 4/1998 | Steinberg |
| 5,815,070 A | * | 9/1998 | Yoshikawa ................. 180/272 |
| 6,078,265 A | | 6/2000 | Bonder et al. |
| 6,100,811 A | | 8/2000 | Hsu et al. |
| 6,124,805 A | | 9/2000 | Gabbard |
| 6,148,212 A | * | 11/2000 | Park et al. ................ 340/426.2 |
| 6,157,317 A | | 12/2000 | Walker |
| 6,225,890 B1 | * | 5/2001 | Murphy ................. 340/426.19 |
| 6,229,908 B1 | | 5/2001 | Edmonds, III et al. |
| 6,232,874 B1 | | 5/2001 | Murphy |
| 6,232,884 B1 | | 5/2001 | Gabbard |
| 6,310,542 B1 | | 10/2001 | Gehlot |
| 6,313,740 B1 | * | 11/2001 | Goetz .................... 340/426.23 |
| 6,356,186 B1 | * | 3/2002 | Price et al. ................. 180/287 |
| 6,430,488 B1 | | 8/2002 | Goldman et al. |
| 6,441,725 B1 | | 8/2002 | Helm et al. |
| 6,626,537 B1 | | 9/2003 | Odom et al. |
| 6,748,792 B1 | * | 6/2004 | Freund et al. ............... 180/272 |
| 6,810,309 B2 | | 10/2004 | Sadler et al. |
| 6,898,493 B2 | | 5/2005 | Ehrman et al. |
| 6,914,668 B2 | | 7/2005 | Brestel et al. |
| 6,926,429 B2 | * | 8/2005 | Barlow et al. ................ 340/576 |
| 6,946,966 B2 | * | 9/2005 | Koenig ........................ 340/576 |
| 6,956,467 B1 | * | 10/2005 | Mercado, Jr. ............ 340/426.2 |
| 7,003,337 B2 | | 2/2006 | Harjunmaa et al. |
| 7,016,713 B2 | | 3/2006 | Gardner et al. |
| 7,088,219 B2 | * | 8/2006 | Dawson et al. ........... 340/426.2 |
| 2002/0186144 A1 | | 12/2002 | Meunier |
| 2004/0008103 A1 | | 1/2004 | Kady et al. |
| 2004/0073440 A1 | | 4/2004 | Garbers et al. |
| 2004/0263357 A1 | | 12/2004 | Hamilton |
| 2005/0171413 A1 | | 8/2005 | Blair |
| 2005/0184858 A1 | | 8/2005 | Griffin et al. |
| 2007/0049809 A1 | | 3/2007 | Bechtel et al. |
| 2007/0073118 A1 | | 3/2007 | Ridder et al. |
| 2008/0208018 A1 | * | 8/2008 | Ridder et al. ................ 600/322 |

FOREIGN PATENT DOCUMENTS

| | | |
|---|---|---|
| JP | 2000-326670 | 11/2000 |
| JP | 2003-120094 | 4/2003 |
| JP | 2004-38278 | 2/2004 |
| WO | WO 03/091711 A1 | 11/2003 |

OTHER PUBLICATIONS

Ver Steeg, Benjamin et al.; "Photonics technology enables accurate, noninvasive alcohol testing. A New Eye on Law Enforcement," *SPIE'S oemagazine*, Jun./Jul. 2005, pp. 26-28.

Burmeister, Jason J. et al.; "Evaluation of Measurement Sites for Noninvasive Blood Glucose Sensing with Near-Infrared Transmission Spectroscopy," *Clinical Chemistry 45*, vol. 9; 1999, pp. 1621-1627.

Billbill, "20. Technology to the rescue!," Internet page, Nov. 17, 2005, 1 pg., found at http://216.239.51.104/search?q=cache:279mIvATXXAJ:www.plastic.com/article.html%3Bsid%3.., Oct. 7, 2009.

Internet page, "A. Modification to Existing Vehicles," 1 pg., found at http://personalpages.tds.net/~cimarron/technical%20report/chapter%206.htm, Oct. 7, 2009.

"Magnetic stripe card," Wikipedia, 4 pgs., found at http://en.wikipedia.org/wiki/Magnetic_stripe_card, Jan. 27, 2006.

NCADD National Commission Against Drunk Driving, "Sanctioning and Supervising Impaired Drivers," website page, found at http://www.ncadd.com/santion_edlsdl.cfm, 1 pg., Jan. 27, 2006.

The Library of Congress, Search results—Thomas (Library of Congress), 3 pgs., found at http://thomas.loc.gov/cgi-bin/bdquery/z?d107:HR04633:@@@L&summ2=m&, Jan. 27, 2006.

"Swipe," website pages, 6 pgs, found at http://www.we-swipe.us/research.html, Jan. 27, 2006.

"Maxking—Driving License Smart Card," website pages, 4 pgs., found at http://www.maxking.com/drivelic.htm, Jan. 27, 2006.

National Drivers License ID, "Congress Debates National Drivers License with ID Tracking Chip. Senate Follows up by Passing The Real ID Act," 5 pgs, found at http://www.dojgov.net/national_license-01.htm, Jan. 27, 2006.

"Smart card," Wikipedia, 7 pgs., found at http://en.wikipedia.org/wiki/Smart_card, Jan. 27, 2006.

* cited by examiner

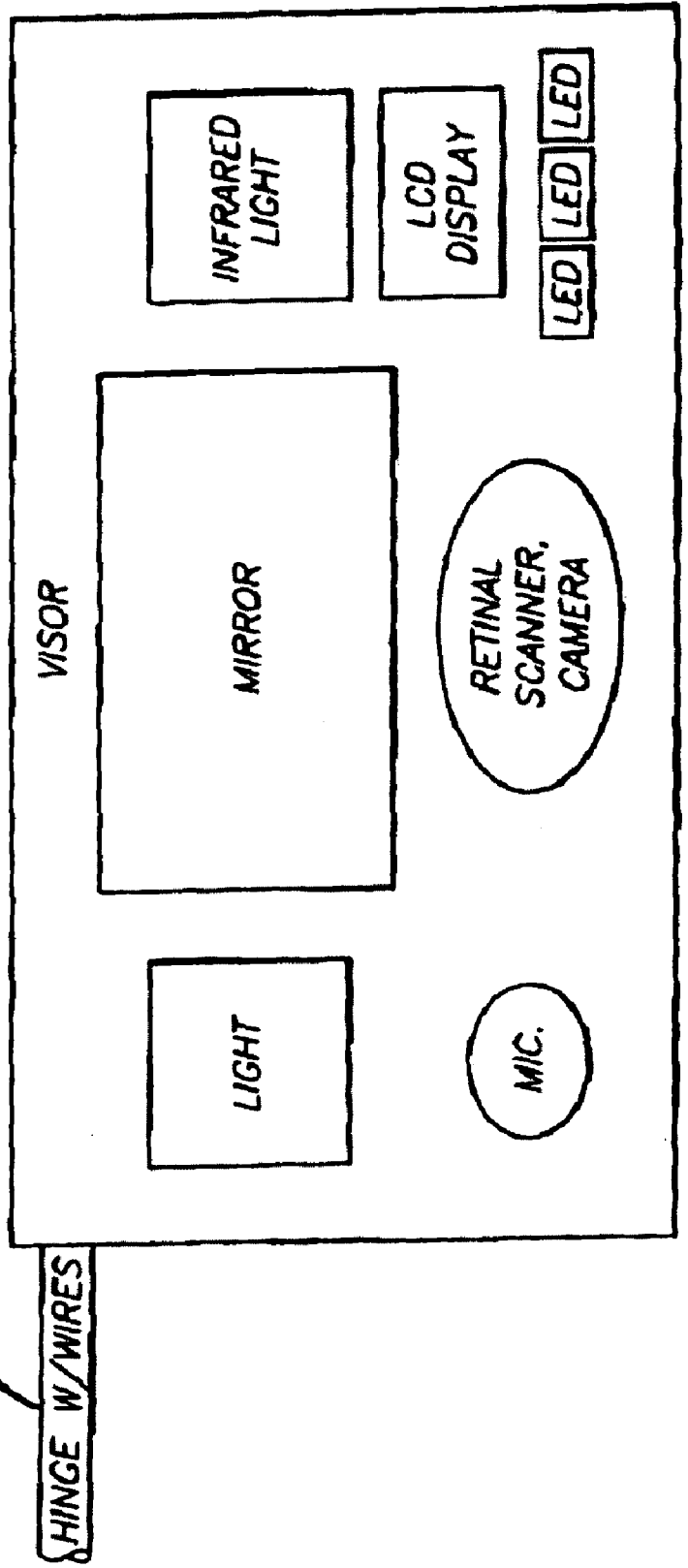

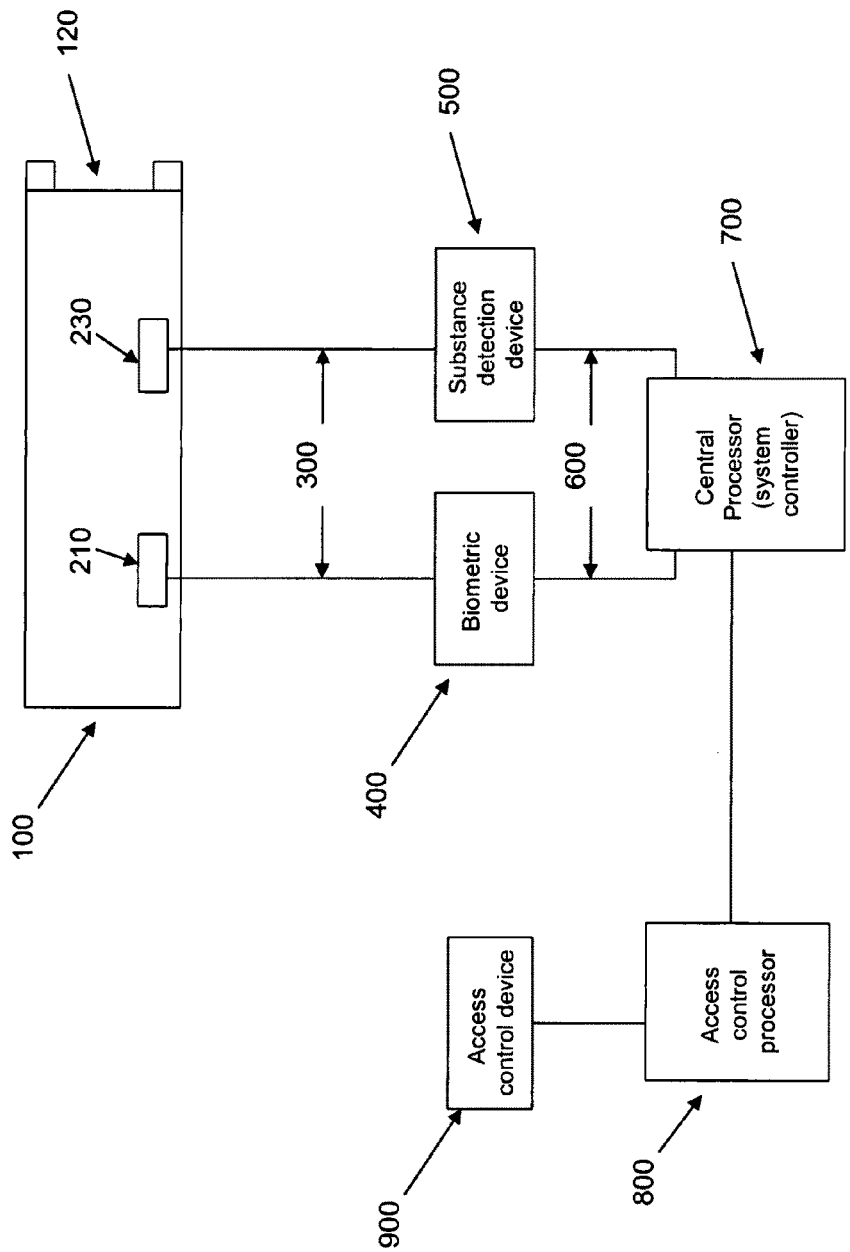

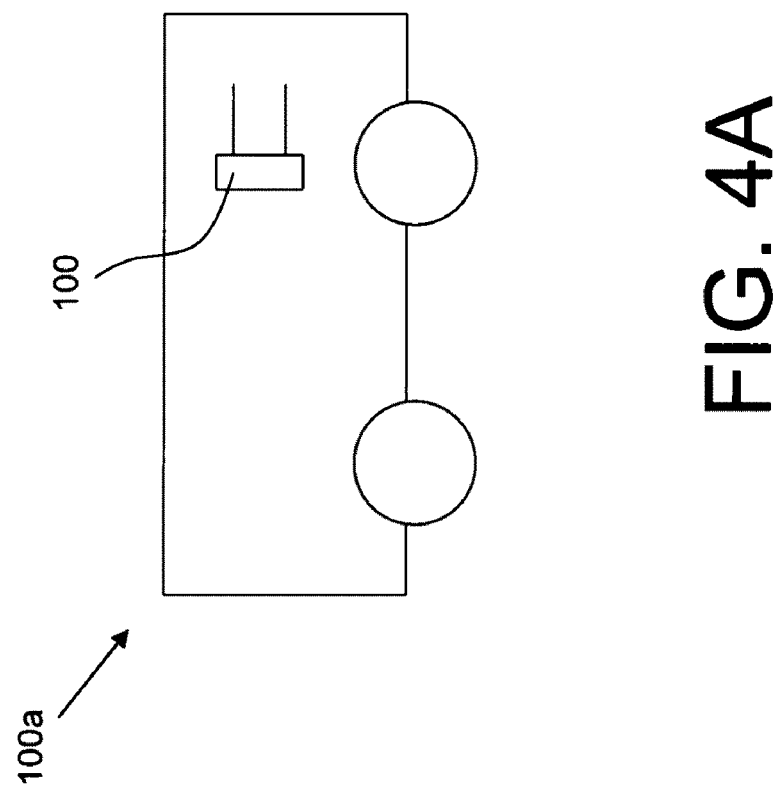

FIG. 24A Transmission mass path x2
FIG. 24B Transmission mass path x1
FIG. 24C reflective path

METHOD AND SYSTEM FOR CONTROLLING A VEHICLE GIVEN TO A THIRD PARTY

CROSS-REFERENCE TO RELATED APPLICATION(S)

This application claims priority to and the benefit of U.S. Provisional Application No. 60/773,141, filed on Feb. 13, 2006, and U.S. Provisional Application No. 60/789,822, filed on Apr. 5, 2006, the entire contents of which are incorporated herein by reference.

FIELD OF THE INVENTION

The present invention relates to method and system for controlling a vehicle given to a third party.

BACKGROUND OF THE INVENTION

According to the National Institute on Alcohol Abuse and Alcoholism No. 25 PH 351 July 1994, "Epidemiologic studies reveal the extent of alcohol's effect on transportation safety in the United States. First, 40 percent of all traffic fatalities (the leading cause of accidental death) are alcohol related. Second, although alcohol has not been directly implicated in U.S. commercial airline crashes, typical estimates of alcohol involvement by pilots in fatal general aviation crashes range from 10 to 30 percent. Third, a recent review of Coast Guard reports suggests possible alcohol involvement in 60 percent of boating fatalities (including persons who fell overboard). Finally, in post-accident testing of railroad employees in 1990, 3.2 percent tested positive for alcohol or other prohibited drugs. The percentage of alcohol or other drug involvement may be higher when a fatality is involved."

As such, there is a need for a method and system adapted to test and/or prevent an intoxicated individual from operating a vehicle or other device, whether it is a car, boat, plane, bus, heavy equipment, or entry point.

Biometric authentication sensors have been used to prevent or limit access to secure facilities and as a substitute for alternative forms of security such as keycards or passwords. Biometric sensors are often considered superior to other identification systems as they are generally more difficult to disable, tamper with, or bypass. However, biometric sensors have still not gained wide acceptance in the field of automobiles and other vehicles. This may be because biometric sensors are expensive, difficult to integrate with existing vehicles, or difficult to operate.

The operation of a vehicle normally requires only a key. Anti-theft devices exist which add security based on a pass code. More advanced anti-theft devices exist to disable vehicles if biometric authentication, such as a fingerprint scan, is unsuccessful. Limited standalone breathalyzer devices exist to disable a vehicle if a driver's blood alcohol level exceeds preset levels.

Vehicle control systems are severely lacking in a variety of aspects. For example, there is not one individual system that ties each of the elements together. For example, to require a breathalyzer test and a biometric identification would presently require two distinct systems that are redundant, costly, and not necessarily compatible.

Also, although substance testing, such as alcohol testing, is typically associated with driving under the influence (DUI), it can also be associated with medicine, workplace safety, probation monitoring, etc. Breath and in-vitro (e.g., blood and saliva) substance measurement methods are currently used to correlate (determine) a concentration of the substance in a person. The breath and in-vitro substance measurement techniques suffer from three key limitations. That is, they require handling of a bodily fluid, which gives rise to biohazard concerns, they require some degree of direct subject supervision from a test administrator, and they do not measure the concentration of substance actually in the person in real time.

Therefore, there is a need for a method and system for non-invasive and/or in-vivo substance testing that can improve biohazard safety and/or provide unsupervised and/or actual real time testing. Further, there exists a need for a method and system that can be combinable with an authenticator, such as a biometric sensor, to automate the testing, reduce and/or eliminate fraud and/or the need for supervision during testing and/or to prevent or limit an intoxicated individual from operating a vehicle or other device, whether it is a car, boat, plane, bus, heavy equipment, or entry point. The coupling of the biometric sensor with the substance testing system should be as close as possible for concurrent and/or substantially simultaneous authentication and substance evaluation.

SUMMARY OF THE INVENTION

An aspect of an embodiment of the present invention is directed to a light source (such as an LED(s)), a mercury xenon arc lamp, a tungsten halogen lamp, or a diode laser at a specific (single) wavelength for non-invasive and/or in-vivo testing of a concentration of a substance in a tissue of a person. Another aspect of an embodiment of the present invention is directed to two or more specific wavelengths for non-invasive and/or in-vivo substance analysis. Another aspect of an embodiment of the present invention is directed to a base reading and a later reading for comparison and/or determination of a concentration of a substance in a tissue of a person. Another aspect of an embodiment of the present invention couples a biometric sensor with a substance sensor at close proximate locations for concurrent and/or substantial simultaneous authentication and substance evaluation. Another aspect of an embodiment of the present invention provides a method and system for controlling a vehicle given to a third party (e.g., a valet).

An embodiment of the present invention is directed to an optical substance detector including a light source (e.g., a halogen lamp) and a fiber optic bundle attached to the halogen lamp to illuminate a test sample (e.g., an area of the test sample) with a configured wavelength filtering system. The desired wavelength bands are reflected back to a detector. Through an evaluation involving a statistical modeling analysis, the test sample's blood alcohol concentration (BAC) is determined with respect to a legal limit to operate a vehicle and, if the BAC is not within the legal limit, the vehicle is disabled.

An embodiment of the present invention provides a system for preventing use of a vehicle by an operator of the vehicle. The system includes a system controller; a biometric authenticator coupled to the system controller; and a substance detecting device adapted to provide a substance level in the operator to the system controller. Here, the system controller is adapted to communicate a driving restriction to the vehicle if the substance level in the operator is above a tolerance level or if the operator is not authenticated by the authenticator, the substance level is determined at an extremity of the operator, the operator is also authenticated at the extremity, and the extremity is selected from the group consisting of finger, thumb, toe, ear, palm, sole, foot, hand, and head.

In one embodiment, the system controller is further adapted to communicate with the vehicle to permit the vehicle to start if the operator has been authenticated by the authenticator and the substance level in the operator is not above the tolerance level.

In one embodiment, the authenticator includes a biometric authenticator selected from the group consisting of a fingerprint authenticator, a face recognition authenticator, a hand-geometry authenticator, a voice authenticator, and combinations thereof.

In one embodiment, the authenticator includes a fingerprint sensor, and wherein the substance level in the operator is determined in-vivo within the finger of the operator.

In one embodiment, the substance detecting device is adapted to detect an alcohol level in the operator.

In one embodiment, the substance detecting device includes a broadband detector. The substance detecting device may further include a light source configured to direct a light beam at a specific wavelength band toward the broadband detector, which may be achieved by directing the light beam at an extremity such that reflected light is received by the detector. The specific wavelength band may be within a range from about 1300 nm to about 2400 nm. The range may be selected from the group consisting of a first range from about 1400 nm to about 1500 nm, a second range from about 1650 nm to about 1750 nm, and a third range from about 2200 nm to about 2400 nm. The specific wavelength band may be at about 1450 nm. The broadband detector may be a single detector. The single detector may be an InGaAs detector.

In one embodiment, the extremity is the finger.

In one embodiment, the substance detecting device includes a broadband detector, a first light beam at a first specific wavelength band directed toward the broadband detector, and a second light beam at a second specific wavelength band directed toward the broadband detector. The first specific wavelength band may be at a wavelength where ethanol is less absorptive than water and the second specific wavelength band is at a wavelength where ethanol is more absorptive than water. The broadband detector may be a single detector. The single detector may be an InGaAs detector. The first specific wavelength band may be within a range from about 1400 nm to about 1500 nm and the second specific wavelength band may be within a range from about 1650 nm to about 1750 nm. Alternatively, the first specific wavelength band may within a range from about 1400 nm to about 1500 nm and the second specific wavelength band may be within a range from about 2200 nm to about 2400 nm.

In one embodiment, the substance detecting device includes a broadband detector, a first light beam at a first specific wavelength band directed toward the broadband detector, a second light beam at a second specific wavelength band directed toward the broadband detector, and a third light beam at a third specific wavelength band directed toward the broadband detector. The broadband detector may be a single detector. The first specific wavelength band may be within a range from about 1400 nm to about 1500 nm, the second specific wavelength band may be within a range from about 1650 nm to about 1750 nm, and the third specific wavelength band may be within a range from about 2200 nm to about 2400 nm. The first specific wavelength band may be at about 1450 nm. In one embodiment, the system for preventing use of the vehicle by the operator of the vehicle may further include a light source configured to provide the first, second, and third light beams. In one embodiment, the system for preventing use of the vehicle by the operator of the vehicle may further include a filtering system disposed between the light source and the broadband detector and adapted to provide the first, second, and third light beams at the first, second, and third specific wavelength bands to the broadband detector.

In one embodiment, the substance detecting device includes a single broadband detector selected from the group consisting of a PbS detector, a PbSe detector, an InAs detector, an InGaAs detector, an InSb detector, and a HgCdTe detector and a light source adapted to direct a light beam at a specific wavelength to the single broadband detector. In one embodiment, the system for preventing use of the vehicle by the operator of the vehicle may further include a wavelength filtering system disposed between the light source and the single broadband detector and adapted to provide the light beam at the specific wavelength band to the single broadband detector. The wavelength filtering system may be disposed closer in distance to the single broadband detector than to the light source. In one embodiment, the system for preventing use of the vehicle by the operator of the vehicle may further include a platform coupled to both the light source and the single broadband detector, wherein the platform is configured to contact a surface of the extremity of the operator and has an index of refraction substantially equal to that of the surface of extremity of the operator.

In one embodiment, the vehicle includes an automobile. The automobile may be a rental car.

In one embodiment, the vehicle includes a vehicle selected from the group consisting of an aircraft, a mass transit vehicle, a watercraft, a piece of industrial equipment, and a piece of heavy machinery and equipment.

In one embodiment, the authenticator includes a fingerprint sensor, and the substance level in the operator is determined in-vivo at a tissue within the finger of the operator.

In one embodiment, the substance detecting device is adapted to detect an alcohol level in the operator.

In one embodiment, the substance detecting device includes a broadband detector. Here, the substance detecting device may further include a diode laser configured to direct a light beam at a specific wavelength toward the broadband detector. The broadband detector may be a single photodiode detector. The single photodiode detector may be an InGaAs photodiode detector. The extremity may be the finger.

In one embodiment, the system further includes a credential sensor coupled to the system controller and adapted to sense a verifiable credential of the operator. Here, the system controller may be adapted to verify that the operator authenticated by the authenticator matches the verifiable credential of the operator. The verifiable credential may include a credential selected from the group consisting of a driver's license, an RFID tag, a smartcard, a credit card, a key ring including an infrared (IR) adapter, an under-skin implant, and combinations thereof.

In one embodiment, the substance detecting device includes a broadband detector, a first diode laser configured to direct a light beam at a first specific wavelength toward the broadband detector, and a second diode laser configured to direct a light beam at a second specific wavelength toward the broadband detector. Here, the first specific wavelength may be at a wavelength where ethanol is less absorptive than water and the second specific wavelength is at a wavelength where ethanol is more absorptive than water. The broadband detector may be a single photodiode detector. The single photodiode detector may be an InGaAs photodiode detector.

In one embodiment, the substance detecting device includes a broadband detector, a first diode laser configured to direct a light beam at a first specific wavelength toward the broadband detector, a second diode laser configured to direct a light beam at a second specific wavelength toward the broadband detector, and a third diode laser configured to direct a light beam at a third specific wavelength toward the broadband detector. Here, the broadband detector is a single photodiode detector.

An embodiment of the present invention provides a time clock system. The system includes a system controller; a biometric authenticator coupled to the system controller; and a substance detecting device adapted to provide a substance level in an operator of the time clock system to the system controller. Here, the substance level is determined at an extremity of the operator, the operator is also authenticated at the extremity, and the extremity is selected from the group consisting of finger, thumb, toe, ear, palm, sole, foot, hand, and head.

In one embodiment, the system controller is adapted to create an alert if the substance level in the operator is above a tolerance level or if the operator is not authenticated by the authenticator. The time clock system may further include a time clock adapted to determine a time when the alert is created.

In one embodiment, the system controller is adapted to communicate with a building security device to permit the operator to access the building security device if the operator has been authenticated and the concentration of the substance is not above a tolerance level. The system controller may also be adapted to communicate with the building security device to restrict the operator from accessing the building security device if the operator has not been authenticated or the concentration of the substance is above the tolerance level. The building access device may include a time clock adapted to determine a time when the operator is permitted access to the building security device.

An embodiment of the present invention provides a system for preventing use of a vehicle by an operator of the vehicle. The system includes a system controller; a biometric authenticator adapted to detect at least one biometric parameter at a first dermal location of an operator of a vehicle and generate an authentication output indicating that the operator has been authenticated; and a substance detecting device adapted to detect a level of a substance in the operator at a second dermal location proximate to the first dermal location and generate a level output. Here, the system controller operates in response to the authentication output and the level output to selectively restrict use of the vehicle if the operator is not authenticated or the detection output is above a preselected tolerance value.

In one embodiment, the first dermal location of the operator is a location capable of biometrically authenticating the operator.

In one embodiment, the first dermal location of the operator is located at a fingerprint of the operator.

An embodiment of the present invention provides a method for in-vivo measurement of a concentration of a substance in a tissue of a person. The method includes directing an incident light beam at a specific wavelength from a diode laser into the tissue; measuring a portion of the incident light beam at the specific wavelength reflected from the tissue with a broadband detector; determining a light beam absorption at the specific wavelength of the substance from the measured portion of the incident light beam reflected from the tissue; and calculating the concentration of the substance in the tissue from the determined light beam absorption. Here, the tissue may include the person's blood, and/or the substance may be alcohol.

In one embodiment, the method further includes authenticating the person whose tissue is being evaluated via a biometric authenticator and a system controller. Here, the system controller may be adapted to communicate with a controlled vehicle to permit the controlled vehicle to operate if the person has been authenticated and the concentration of the substance is not above a tolerance level. The system controller may be adapted to communicate an operating restriction to the controlled vehicle if the person has not been authenticated or the concentration of the substance is above the tolerance level. The controlled vehicle may include an automobile. The automobile may be a rental car. The controlled vehicle may include a vehicle selected from the group consisting of an aircraft, a mass transit vehicle, a watercraft, a piece of industrial equipment, and a piece of heavy machinery and equipment The system controller may be adapted to communicate with a building security device to permit a person to access the building security device if the person has been authenticated and the concentration of the substance is not above a tolerance level. The system controller may be adapted to communicate with the building security device to restrict the person from accessing the building security device if the person has not been authenticated or the concentration of the substance is above the tolerance level. The building access device may include a time clock adapted to determine a time when the person is permitted access to the building security device. The biometric authenticator may include an authenticator selected from the group consisting of an iris authenticator, a retinal authenticator, a fingerprint authenticator, a face recognition authenticator, a hand-geometry authenticator, a voice authenticator, and combinations thereof. The biometric authenticator may include a fingerprint sensor.

In one embodiment, the broadband detector is a single photodiode detector. The single photodiode detector may be an InGaAs photodiode detector.

In one embodiment, the concentration of the substance in the tissue is calculated using only the determined light beam absorption at the specific wavelength of the substance.

In one embodiment, the specific wavelength is about 1310 nm.

In one embodiment, the concentration of the substance from the determined light beam absorption is calculated by using a first concentration regime of the substance having a first light beam absorption characteristic and a second concentration regime of the substance having a second light beam absorption characteristic. Here, the concentration of the substance may be proportional to the light beam absorption at the specific wavelength of the substance in the first concentration regime of the substance, and the concentration of the substance may not be proportional to the light beam absorption at the specific wavelength of the substance in the second concentration regime of the substance. The second light beam absorption characteristic may be determined experimentally. The first light beam absorption characteristic may be determined by:

$$I(\lambda)=I_o(\lambda)e^{-\alpha(\lambda)L},$$

wherein $\lambda$ is the specific wavelength, Io is an incident intensity of the incident light beam, I is a measured transmitted intensity, $\alpha$ is an absorption co-efficient as a function of the specific wavelength $\lambda$, and L is a mass path length of the portion of the incident light beam transmitted through the tissue.

In one embodiment, the step of directing the incident light beam at the specific wavelength from the diode laser into the tissue includes directing the incident light beam to strike a mirror to double a mass path length of the portion of the incident light beam transmitted through the tissue.

In one embodiment, the step of directing the incident light beam at the specific wavelength from the diode laser into the tissue includes directing the incident light beam to a first side of the tissue, and the step of measuring the portion of the incident light beam transmitted through the tissue includes measuring the portion of the incident light beam transmitted through the tissue from a second side of the tissue, and wherein the second side is opposite to the first side.

In one embodiment, the step of directing the incident light beam at the specific wavelength from the diode laser into the tissue includes directing the incident light beam from a first side of the tissue toward a second side of the tissue, and the step of measuring the portion of the incident light beam transmitted through the tissue includes measuring the portion of the incident light beam transmitted through a portion of the tissue and reflected back to the first side of the tissue.

In one embodiment, the diode laser includes a diode selected from the group consisting of a double heterostructure laser diode, a quantum well laser diode, a distributed feedback laser diode, a vertical cavity surface emitting laser (VCSEL) diode, and a vertical external-cavity surface-emitting laser (VECSEL) diode.

In one embodiment, the tissue is located within a finger of the person.

In one embodiment, the specific wavelength is an infrared (IR) wavelength.

An embodiment of the present invention provides a method for in-vivo measurement of a concentration of a substance in a tissue of a person. The method includes directing a first incident light beam at a first specific wavelength from a first diode laser into the tissue; measuring a portion of the first incident light beam at the first specific wavelength reflected from the tissue; determining a first light beam absorption at the first specific wavelength of the substance from the measured portion of the first incident light beam reflected from the tissue; directing a second incident light beam at a second specific wavelength from a second diode laser into the tissue; measuring a portion of the second incident light beam at the second specific wavelength reflected from the tissue; determining a second light beam absorption at the second specific wavelength of the substance from the measured portion of the second incident light beam reflected from the tissue; and calculating the concentration of the substance in the tissue from the determined first light beam absorption and the determined second light beam absorption.

In one embodiment, the concentration of the substance in the tissue is calculated using only the determined first light beam absorption at the first specific wavelength of the substance and the determined second light beam absorption at the second specific wavelength.

In one embodiment, the method further includes directing a third incident light beam at a third specific wavelength from a third diode laser into the tissue; measuring a portion of the third incident light beam reflected from the tissue; and determining a third light beam absorption at the third specific wavelength of the substance from the measured portion of the second incident light beam reflected from the tissue. Here, the step of calculating the concentration of the substance in the tissue also includes calculating the concentration of the substance in the tissue from the determined third light beam absorption.

In one embodiment, the concentration of the substance in the tissue is calculated using only the determined first light beam absorption at the first specific wavelength of the substance, the determined second light beam absorption at the second specific wavelength, and the determined third light beam absorption at the third specific wavelength.

In one embodiment, the first specific wavelength is at a wavelength where ethanol is less absorptive than water and the second specific wavelength is at a wavelength where ethanol is more absorptive than water.

In one embodiment, the portion of the second incident light beam at the second specific wavelength reflected from the tissue is measured after the portion of the first incident light beam at the first specific wavelength reflected from the tissue had been measured.

In one embodiment, the portion of the first incident light beam at the first specific wavelength reflected from the tissue and the portion of the second incident light beam at the second specific wavelength reflected from the tissue are measured with a same broadband detector. Here, the same broadband detector may be a single photodiode detector. The single photodiode detector may be an InGaAs photodiode detector.

An embodiment of the present invention provides a method for in-vivo measurement of a concentration of a substance in a tissue of a person. The method includes directing a first incident light beam at a specific wavelength from a diode laser into the tissue; measuring a portion of the first incident light beam at the specific wavelength reflected from the tissue; determining a first light beam absorption at the specific wavelength of the substance from the measured portion of the incident light beam reflected from the tissue; directing a second incident light beam at the specific wavelength from the diode laser into the tissue after a time interval; measuring a portion of the second incident light beam at the specific wavelength reflected from the tissue; determining a second light beam absorption at the specific wavelength of the substance from the measured portion of the second incident light beam reflected from the tissue; and determining a characteristic of change in the tissue from the determined first light beam absorption at the specific wavelength and the determined second light beam absorption at the specific wavelength.

In one embodiment, the method further includes calculating the concentration of the substance in the tissue after the time interval from the determined characteristic of change in the tissue. Here, the concentration of the substance from the determined light beam absorption may be calculated by using a first concentration regime of the substance having a first light beam absorption characteristic and a second concentration regime of the substance having a second light beam absorption characteristic. The concentration of the substance may be proportional to the light beam absorption at the specific wavelength of the substance in the first concentration regime of the substance, and the concentration of the substance may not be proportional to the light beam absorption at the specific wavelength of the substance in the second concentration regime of the substance. The second light beam absorption characteristic may be determined experimentally.

In one embodiment, the specific wavelength is at a wavelength where ethanol is less absorptive than water.

In one embodiment, the specific wavelength is at a wavelength where ethanol is more absorptive than water.

In one embodiment, the tissue includes the person's blood, and/or the substance is alcohol.

In one embodiment, the tissue is located within a finger of the person.

In one embodiment, the diode laser includes a diode selected from the group consisting of a double heterostructure laser diode, a quantum well laser diode, a distributed feedback laser diode, a vertical cavity surface emitting laser (VCSEL) diode, and a vertical external-cavity surface-emitting laser (VECSEL) diode.

In one embodiment, the portion of the first incident light beam at the specific wavelength reflected from the tissue and the portion of the second incident light beam at the specific wavelength reflected from the tissue are measured with a broadband detector. Here, the broadband detector may be a single photodiode detector. The single photodiode detector may be an InGaAs photodiode detector.

In one embodiment, the tissue is located within a finger of the person.

An embodiment of the present invention provides a method for in-vivo measurement of a concentration of a substance in a tissue of a person. The method includes directing a first incident light beam at a first specific wavelength from a first diode laser into the tissue; measuring a portion of the first incident light beam at the first specific wavelength reflected from the tissue; determining a first light beam absorption at the first specific wavelength of the substance from the measured portion of the first incident light beam reflected from the tissue; directing a second incident light beam at a second specific wavelength from a second diode laser into the tissue; measuring a portion of the second incident light beam at the second specific wavelength reflected from the tissue; determining a second light beam absorption at the second specific wavelength of the substance from the measured portion of the first incident light beam reflected from the tissue; directing a third incident light beam at the first specific wavelength from the first diode laser into the tissue after a first time interval from the directing of the first incident light beam; measuring a portion of the third incident light beam at the first specific wavelength reflected from the tissue; determining a third light beam absorption at the first specific wavelength of the substance from the measured portion of the third incident light beam reflected from the tissue; directing a fourth incident light beam at the second specific wavelength from the second diode laser into the tissue after a second time interval from the directing of the second incident light beam; measuring a portion of the fourth incident light beam at the second specific wavelength reflected from the tissue; determining a fourth light beam absorption at the second specific wavelength of the substance from the measured portion of the fourth incident light beam reflected from the tissue; determining a first characteristic of change in the tissue from the determined first light beam absorption at the first specific wavelength and the determined third light beam absorption at the first specific wavelength; and determining a second characteristic of change in the tissue from the determined second light beam absorption at the second specific wavelength and the determined fourth light beam absorption at the second specific wavelength.

In one embodiment, the method further includes calculating the concentration of the substance in the tissue after the first and second time intervals from the first determined characteristic of change in the tissue and the second characteristic of change in the tissue.

In one embodiment, the first time interval is substantially equal to the second time interval.

In one embodiment, the method further includes directing a fifth incident light beam at a third specific wavelength from a third diode laser into the tissue; measuring a portion of the fifth incident light beam at the fifth specific wavelength reflected from the tissue; determining a fifth light beam absorption at the third specific wavelength of the substance from the measured portion of the fifth incident light beam reflected from the tissue; directing a sixth incident light beam at the third specific wavelength from the third diode laser into the tissue after a third time interval from the directing of the fifth incident light beam; measuring a portion of the sixth incident light beam at the sixth specific wavelength reflected from the tissue; determining a sixth light beam absorption at the third specific wavelength of the substance from the measured portion of the sixth incident light beam reflected from the tissue; and determining a third characteristic of change in the tissue from the determined fifth light beam absorption at the third specific wavelength and the determined sixth light beam absorption at the third specific wavelength. Here, the method may further include calculating the concentration of the substance in the tissue after the first, second, and third time intervals from the first determined characteristic of change in the tissue, the second characteristic of change in the tissue, and the third characteristic of change in the tissue.

An embodiment of the present invention provides a system for controlling a vehicle given to a third party. The system includes a system controller; a mode-indicating device coupled to the system controller; and an authenticator coupled to the system controller. Here, the system controller is adapted to communicate a driving restriction to the vehicle upon an activation of the mode-indicating device by an authorized driver and until a deactivation of the mode-indicating device by the authorized driver, the system controller is adapted to restrict the activation and the deactivation of the mode-indicating device unless the authorized driver has been authenticated by the authenticator, and the driving restriction includes a limit selected from the group consisting of a limit in number of starts, a limit in speed, a limit in acceleration, a limit in number of minutes, a limit in distance, a limit in gears, a limit in locations, and combinations thereof.

In one embodiment, the system further includes a substance detecting device coupled to the system controller and adapted to provide a substance level in the third party to the system controller. Here, the system controller may be further adapted to communicate with the vehicle to permit the vehicle to start if the substance level in the third party is not above a tolerance level. The system controller may be further adapted to communicate another driving restriction to the vehicle if the substance level in the third party is above the tolerance level. The driving restriction may include a command adapted to be sent via a vehicle bus of the vehicle to limit a maximum speed of the vehicle, and the another driving restriction may include a command adapted to be sent via the vehicle bus of the vehicle to block the vehicle from starting.

In one embodiment, the substance detecting device includes a broadband detector. Here, the substance detecting device may further include a diode laser configured to direct a light beam at a specific wavelength toward the broadband detector. The broadband detector may be a single photodiode detector. The single photodiode detector may be an InGaAs photodiode detector. The extremity may be the finger.

In one embodiment, the substance detecting device includes a broadband detector, a first diode laser configured to direct a light beam at a first specific wavelength toward the broadband detector, and a second diode laser configured to direct a light beam at a second specific wavelength toward the broadband detector. Here, the first specific wavelength may be at a wavelength where ethanol is less absorptive than water and the second specific wavelength is at a wavelength where ethanol is more absorptive than water. The broadband detector may be a single photodiode detector. The single photodiode detector may an InGaAs photodiode detector.

In one embodiment, the substance detecting device includes a broadband detector, a first diode laser configured to direct a light beam at a first specific wavelength toward the broadband detector, a second diode laser configured to direct a light beam at a second specific wavelength toward the broadband detector, and a third diode laser configured to direct a light beam at a third specific wavelength toward the broadband detector. Here, the broadband detector is a single photodiode detector.

In one embodiment, the driving restriction further includes another limit selected from the group consisting of a limit in activatable accessories, a limit in openable compartments, and combinations thereof. Here, the control panel may be further adapted to send a message to a cell phone if the limit has been exceeded to notify a designated individual remotely, and/or the control panel may be further adapted to create an alert if the limit has been exceeded to notify the authorized driver when the authorized driver retakes control of the vehicle.

In one embodiment, the third party is a valet.

BRIEF DESCRIPTION OF THE DRAWINGS

The accompanying drawings, together with the specification, illustrate exemplary embodiments of the present invention, and, together with the description, serve to explain the principles of the present invention.

The patent or application file contains at least one drawing executed in color. Copies of this patent or patent application publication with color drawing(s) will be provided by the Office upon request and payment of the necessary fee.

FIG. 3 shows a visor mounted biometric device pursuant to aspects of an embodiment of the present invention.

FIG. 4 shows a block diagram of an enhanced biometric and substance detection system and device pursuant to aspects of an embodiment of the present invention.

FIG. 4A shows a block diagram of a vehicle including the enhanced biometric and substance detection system and device of FIG. 4 pursuant to aspects of an embodiment of the present invention.

DETAILED DESCRIPTION

Figure 1:
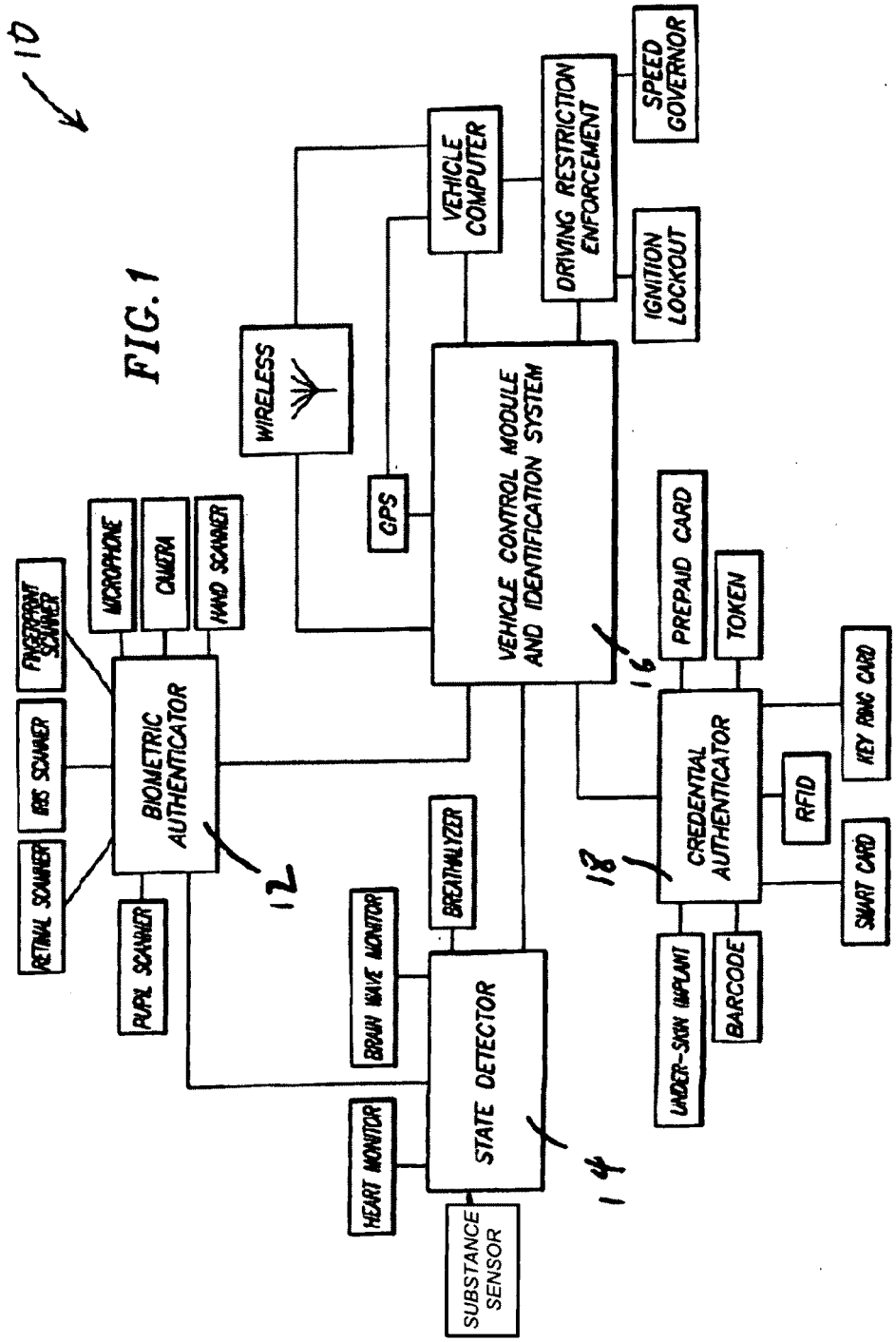
FIG. 1 shows a block diagram of a driver's card identification system and/or a system of preventing use (or unauthorized use) of a vehicle by an operator (or driver) of the vehicle pursuant to aspects of an embodiment of the present invention.

In the following detailed description, only certain exemplary embodiments of the present invention are shown and described, by way of illustration. As those skilled in the art would recognize, the described exemplary embodiments may be modified in various ways, all without departing from the spirit or scope of the present invention. Accordingly, the drawings and description are to be regarded as illustrative in nature, and not restrictive.

As envisioned in an embodiment of the present invention, a driver's card identification system is provided. The system allows for, among other things, using personal biometrics in combination with verifiable credentials to restrict and enforce operations of a vehicle. The system allows restriction to authorized drivers, provides theft protection, assures compliance with driving and/or licensing laws, offers customizable control for use by parents or when a vehicle is given to a third party such as a valet, service facility, designated driver, friend, or employee. The system further provides secure, encrypted, verifiable statistical information about a person's driving habits and who was driving at a particular time. The system may further restrict the driving of vehicles while under the influence of alcohol or drugs.

One embodiment of the present invention envisions a system that blocks or prevents unauthorized use of a vehicle by using biometrics coupled with verifiable credentials. This may be accomplished by requiring a biometric verification, such as an iris scan, retinal scan, fingerprint scan, face recognition scan, hand-geometry scan, or voice authentication in combination with a verifiable credential. A verifiable credential may be a driver's license with barcode, magnetic stripe, an RFID, a smartcard, a credit card, a key ring including an infrared adapter, an under-skin implant, or other credential issued by a trusted source. Such a system could further include adjusting the requirements to start or drive the vehicle based on the time of day, day of week, number of hours driven in a particular time period, driving conditions, location, number of passengers or their status, government-issued alert status, or planned route or destination. Such a system may be implemented in a variety of ways. One implementation is through the use of a software and hardware-based tamper-proof control module (or system controller) that accepts as inputs a biometric authenticator, and a credential-reader. The control module may include or be connected to a database either in the vehicle or through a wireless connection. The control module can verify that the biometric authentication matches the verifiable credentials and that the credentials and/or authentication is valid. Based on the results of the verification, the control module may communicate with the vehicle computer to permit the vehicle to start or to communicate driving restrictions including those received from the database or wireless connection. The control module may also report an error or request additional credentials based on the verification, information from the database, or information from the wireless connection.

Another embodiment of the present invention envisions a system that blocks or prevents unauthorized use of a vehicle by using biometrics and/or verifiable credentials coupled with a detection system for alcohol or drugs. Such a system could include requiring a particular driver or class of drivers to pass a breathalyzer test based on their biometric scan and/or use information obtained from the biometric identification to restrict the use of the vehicle. For example, retinal scanners may identify that a person is under the influence of alcohol or drugs because the scanned retinal pattern or blood vessel pattern is different for a person under the influence of alcohol and certain drugs as compared to that same person when not under the influence. Further, a pupil dilation test may be performed to determine intoxication by measuring the speed and extent that the pupil dilates when a beam of light is flashed at the eye. This change in retinal pattern or pupil dilation may be quantifiable or measured as a percent of deviation from the expected pattern. If the deviation exceeds a tolerance, then the vehicle may be restricted or may require an alternate form of verification such as a call to an operator, visit from a police officer, or an alternate proof of sobriety such as a breathalyzer. For example, if a driver who is under the influence of alcohol attempts to verify his identity using a retinal scan, a flag in the system could be activated requiring him to prove that he is not drunk (such as by notifying a police officer or family member via wireless communications) or disabling the vehicle or limiting his speed or route. Such a coupling of biometrics with substance detection is beneficial since it allows different detection thresholds and responses to be set for different individuals. It also reduces the likelihood that a friend or passenger could fool a standard ignition lockout breathalyzer device by blowing into it then letting the intoxicated driver drive. Tolerances could be controlled from state-to-state or customized to a particular driver by storing the tolerance level in their credentials. Customization of tolerance levels could allow particular drivers to be authorized to drive if their scan differentiation exceeds certain percentages, such as an elderly person whose eyes may be changing. If an alternate proof is provided, such as an override code from a police officer, any information about that code would be stored in a log, such as the overriding officer's badge number.

Another embodiment of the present invention envisions a hand-held biometric identification device that may also function as a substance detector and may also function as a credentials verifier. A hand-held biometrics device may include a portable retinal scanner, fingerprint scanner, voice analyzer, iris scanner, RFID reader, face recognition scanner, or hand-geometry scanner. Such a device may be used by a police officer during a traffic stop or wherever highly reliable identification is desired. The device may include a power supply or battery, a biometric authenticator, a state detector, or a credentials authenticator. The device may further include a database or wireless access to a database. The hand-held device may further communicate with a vehicle control module to download biometric information, state information, credentials information, or logs. In an exemplary embodiment, the hand-held biometric identification device would include a biometric authenticator, in one representative embodiment, a retinal scanner, coupled to a credentials authenticator, in one representative embodiment, a barcode reader. A government authority, such as a police officer, could swipe a person's driver's license and/or insurance card, and perform a retinal scan. The device could then cross-check the license, insurance card, and retinal scan to authenticate the identity of the individual. The system may further verify the credentials against a database to determine that they are currently valid and may interface with a computer, such as one in a police car, to determine if there is a reason to further detain the individual.

Another embodiment of the present invention envisions a system that allows parental control of a vehicle through the use of biometric identification. For instance, a parent may use such a system to assure that only their child may drive the car and may not lend the car to a third party. Similarly, a parent using such a system may view logs of driving statistics such as speed, route, and number of stops. By coupling such a system with biometrics, a parent can be assured that the person driving the vehicle is their child. Further, through the use of biometrics coupled to a GPS, a parent could allow their child to drive only on specific routes, such as to and from school. The system may also be optionally reset or driving privileges increased remotely by the use of a pin number, password, or remote authorization. The parental control system may allow multiple 'home locations' to be programmed, so that the system can track how far the vehicle is from each location. The vehicle may also be 'recalled' home by sending an SMS message or communication to the vehicle. If a vehicle is recalled, it may restrict the driver from deviating from a course home. In the event of a deviation, various enforcement measures may be taken such as limiting the speed, opening a telephone connection to a phone number, or requiring a reply message to be sent explaining why the deviation occurred. The parental control system may also be coupled with the state detector to prevent a child from operating the vehicle while intoxicated or tired. The system may further provide logs of route, speed, stops, braking habits, and number of passengers. Driving times may further be restricted during specified hours to prevent the driver from operating the vehicle. For parental controls, this may prevent a child from operating the vehicle during school hours once they have parked the vehicle. A principal or other individual may be preauthorized to allow exceptions to the policy. Preauthorization may occur by that individual's credentials being entered into the system by the parent.

The system may optionally be connected to a computer or the information downloaded wirelessly to allow logs to be analyzed and settings to be customized. A computer software program may be operable to connect to the system, authenticate, and download the information. The information may be analyzed, published to a web page, or used to provide reports of third party driving habits, such as children or employees.

Another embodiment of the present invention envisions a system to restrict driving privileges of particular individuals by a government, police, or law enforcement agency. For example, an individual may only be allowed to drive to and from work although the vehicle may be used by other people without such restrictions. Therefore, such a system could use biometric verification to enforce particular driving restrictions with respect to particular drivers.

Another embodiment of the present invention envisions a system that allows for control of a vehicle given to a third party. A third party may include a valet, service facility, designated driver, friend, or employee. The vehicle may be configured to operate in a restricted capacity, such as by limiting its speed, acceleration, number of minutes or miles it can travel, gears that it can shift, locations that it can go, accessories that can be activated, or compartments that may be opened. A time-delayed valet button or system may be activated to engage the restrictions until an authorized driver retakes control of the vehicle or a proper non-valet key is used. A valet may not be required to perform a biometric identification, but access to the vehicle would be restricted. A valet option may also include a limited number of additional starts, so that the valet has the ability to move the car if needed. If the valet attempts to exceed the number of starts or other restrictions the vehicle can create an alert and optionally notify a designated individual remotely, such as by sending an SMS message to a cell phone. When such a system is engaged a sound may be emitted or a visual alert provided. The system may also be optionally reset by the use of a pin number or password. This aspect may be coupled with biometric identification and/or credential verification to assure ease of operability between drivers.

The system may also be coupled with a state detector such as a breathalyzer, a noninvasive finger scan, a heart rate monitor, brain activity monitor, or other device for detecting conditions of a driver to restrict driving based on those conditions—for example, to detect the onset of a heart attack or a tired driver or to prevent road rage.

Another embodiment of the present invention envisions a system and method adapted to enforce driving restrictions based on biometric verification or verifiable credentials. Vehicles may be equipped to drive on certain designated streets, lanes, or park in particular parking lots based on the driver's identity. Speeds may be limited through the use of a governor or other speed control device based on the biometric verification or verifiable credentials. Drivers with bad driving histories may be required to limit their speed or routes based on such biometric identification. Similarly, if the government determines it is necessary, the driver's credentials may be revoked, or restrictions may be placed on them which the vehicle would enforce or keep and/or transmit a log if violated.

Another embodiment of the present invention envisions a master-override feature for use by authorized individuals such as police, tow-trucks, and emergency responders. When a vehicle's biometric override feature has been enabled it may flash lights, emit sounds, or communicate wirelessly with a database or alert system.

Another embodiment of the present invention envisions a visor-mounted biometrics device. Such a device may be an iris scanner, retinal scanner, or microphone and/or camera. The visor is a particularly good location for such a device since it is generally a fixed distance from the driver, may include a mirror or light, may include a swivel or adjustment for height or distance from the driver, and may be easily stowed for cosmetic or antitheft purposes. The biometrics device may also continue to operate while the vehicle is in use or when the driver door is opened or when a sensor detects a new driver has entered the vehicle. Such a visor mounted biometrics device could also prevent carjacking by assuring that the driver is verified. The visor-mounted biometrics device may include an entire biometrics system or just one element, such as a camera. The logic and circuitry driving the biometrics device need not be located in the visor. The visor may also include a series of LEDs to indicate status or success of the biometrics system or overall system. The visor may also include an LCD display to assist with alignment of the biometrics device in the case of a retinal, iris, or pupil scanner. An LCD in the visor may also display status information about the current driver or the system, which is particularly beneficial for retrofitting existing vehicles where dashboard space may be limited. A microphone may also be included in the visor to perform authentication or for voice-activated control of the system.

Another embodiment of the present invention envisions a biometrics authentication system coupled to an alternate driving device such as a joystick, eye-tracker, or voice-controlled steering or driving control system. Such a system could include a fingerprint scanner positioned on a joystick, or a retinal scanner that also functions to track eye movement to control aspects of the driving in addition to providing driver authentication. A voice-activated biometric identifier may also be used for voice-activation of vehicle features such as the radio.

Another embodiment of the present invention envisions a system and method adapted to allow the biometric verification or credential information to be wirelessly transmitted to a law enforcement officer during a chase or when a vehicle is pulled over. Such transmission may be encrypted by the system and unencrypted by a handheld system or a system located in the officer's vehicle. The officer may download any logs from the system wirelessly or view any logs, including the recent route, speed, or drivers of the vehicle by performing a biometric scan cross-checked to their credentials inside the vehicle. The information may also be relayed to a central location for further analysis.

Another embodiment of the present invention envisions a system and method adapted to allow the biometric verification and credential information to be easily communicated between drivers in the event of a vehicle collision. Such communication helps prevent individuals from providing false information and provides speed and accuracy of the information. The information may be communicated wirelessly or a paper report may be printed from an in-vehicle printer attached to the system. The information may also be wirelessly transmitted to insurance companies or the DMV for a report to be generated.

Another embodiment of the present invention envisions a system and method adapted to allow the biometric verification and credential information to be received and stored by a vehicle involved in a hit-and-run accident. Further, such information may be encrypted to protect privacy and may be brought to a law enforcement agency such as the DMV or a police station where it can be decrypted. Such a system may provide a virtual snapshot of an accident or crime scene, furthering the ability of parties and witnesses to be located. The police can also backtrack or pull up what routes had previously been driven. Routes may be stored in an encrypted manner or a checksum may be calculated to confirm authenticity.

Another embodiment of the present invention envisions a system and method adapted to keep a log of the previous drivers of the vehicle. The information may be stored in the system, transmitted wirelessly at particular intervals, transmitted each time the car is started or the foot is depressed on the brake, or transmitted at fixed intervals such as during vehicle renewal.

As envisioned, another embodiment of the present invention further includes charging different individuals different fees based on where they are traveling or for what purpose. A pay-per-use refillable credential may be used to authorize particular individuals to drive to certain locations at a low cost and to drive to other locations at a higher cost. For example, driving to work may be charged at a low cost, but driving to a bar at a higher cost. Such costs may be paid at standalone kiosks or directly billed to a driver's account.

Another embodiment of the present invention envisions a system and method adapted to allow the biometric verification or credential information to be transmitted to a parking lot attendant or automated system to provide desired services, such as premium parking spots to particular customers.

Another embodiment of the present invention envisions a system and method adapted to require biometric identification and/or credential information for all individuals entering a vehicle. Such information can be used to encourage carpooling by restricting access to particular roads based on the individuals in the vehicles, prevent terrorism, or charge or debit each passenger based on their travel.

Another embodiment of the present invention envisions a wireless vehicle monitoring system. The monitoring system may include a satellite connection, either bidirectional or unidirectional. The wireless connection could provide periodic updates of license and insurance information. Further, the system may be configured to power-up or receive the wireless communications at specific days/times or may be configured for constant monitoring. The system may also communicate through a cell-phone including via blue-tooth. Providing wireless updates may allow the system to work without the need to swipe a valid driver's license or insurance card, as such information would already be stored in the system and matched to a driver's biometric information. Further, the system may be capable of receiving targeted communications including SMS messages. The communications could be interpreted by the system and, upon an initial verification of authenticity or key exchange, operations contained in the messages could be performed, such as throttling the speed of the vehicle, shutting down the vehicle, sounding the horn or lights, or updating the system to reflect a change in the verified credentials such as a suspended driver's license.

Another embodiment of the present invention envisions a system and method for linking insurance rates and driving taxes to the amount or type of driving of a driver of a vehicle. Different plans may be purchased, including an unlimited use plan, a limited mileage plan, a single-driver plan, and plans that include certain number of over-miles at different prices. Insurance rates may be set based upon the information logged in the system. To accomplish this end, the logs may be transmitted to the insurance company or a summary report may be generated and sent. Information contained in the insurance ID card may also be used to enforce driving restrictions. For example, if the driver exceeds the number of miles on his plan he may be restricted from certain routes. Similarly, top-up cards may be purchased or a charge to the driver's account may be authorized. Drivers with low mileage, low average speed, safe routes, low-traffic routes, or who average a high number of passengers may be rewarded by offering a credit, discount, or points redeemable for a gift.

Another embodiment of the present invention envisions an easy-to-use voice-responsive system. The system can provide audible prompts and includes voice recognition to accept commands. When a driver enters the vehicle the system can greet the driver, prompt the driver to provide their credentials and biometric information. A cross-check can be performed and a database queried. If the verification is successful, the driver may be further greeted, presets may be set on the radio or other in-vehicle devices, and the vehicle enabled. If the verification fails the driver may be given additional attempts before being prompted to leave the vehicle. If the driver does not leave the vehicle an alarm may sound or a designated person or police may be notified.

The driver may also request guidance about a route or assistance in finding a store. Advertisements may be presented based on the driver. Coupons may also be offered. An individual, for example, looking for a dry cleaner along a particular route or within a radius may be presented with a list of options including coupons. Advertisers may agree to pay in exchange for a premium listing including better placement or further details.

Embodiments of the present invention, however, are not limited to automobiles. For example, suitable embodiments of the present invention can be used in trucks, airplanes, railroad cars, boats, elevators, metro systems, high-speed vehicles, motorcycles, and other forms of transportation. This system may be encased in a waterproof film or box such as for use in outdoor applications such as motorcycles. The system may also be integrated into the dashboard of motorcycles. The system may also be used in rental vehicles to prevent unauthorized drivers.

In any of the above suitable embodiments it may be desirable to provide biometric verification each time somebody sits in the driver's seat, periodically during driving, when requested by law enforcement, when a further form of identification fails, such as a password, keycard, or verifiable credential, or when authorization is required to enter a toll or restricted road or area.

In any of the above suitable embodiments the biometric information may be encrypted and transmitted, including wirelessly, to a local official, a transceiver/receiver unit, or to a satellite, cellular or other receiving station.

There may be different levels of credentials, such as an owner, a parent, a valet, a friend, a police officer, a tow-truck, or the dealership. The system may be programmed to respond differently to different credentials. Credentials may be assigned levels of authorization, and different levels of authorization may permit different actions. Police officers, for example, may have high levels of authorization, permitting them to override the system or view logs from other drivers. Valets, on the other hand, may have low authorization levels permitting them to drive at low speeds and restricting them from, for example, opening the trunk.

The system may be configured to interface directly with the vehicle computer, or may communicate through blue-tooth, other wireless protocols, or through the vehicle's ODBC diagnostic port or directly by interface with the ignition or starter.

As envisioned, certain embodiments of the present invention include cross-checking a biometric identification with a valid driver's license and valid insurance card to control access to a vehicle. In one embodiment, a driver would enter a vehicle, scan their driver's license and insurance card, and then perform a biometric identification. The system would cross-check the information on the driver's license, insurance card, and biometric identification. If the cross-check was successful, the car would be allowed to start. The information stored on the driver's license and insurance card in an exemplary embodiment would be stored on a tamper-resistant smart card. The biometric information could be cross-checked against the information stored in the smart card, or, in one representative embodiment, be used as a key to unlock an encrypted vehicle starting code stored in the smart-card.

As envisioned, in addition to cross-checking the biometric information with the driver's license and insurance card, substance detectors (e.g., breathalyzer, pupil dilation/retinal scanner device, IR detection device) would be used to verify that the driver is not under the influence of a prohibited substance.

As envisioned, one embodiment of the present invention is adapted to prevent unlicensed, uninsured, or drunk drivers from operating a vehicle. By requiring a driver to verify that he has valid insurance, a valid driver's license, is not intoxicated, and is the same person who is on the insurance card/driver's license, the roads can be made safer. As a further benefit, once such a system is implemented it will reduce vehicle theft since potential thieves would not be authorized drivers and thus could not start the vehicle. Further, such a system would reduce crime, since logs created could be authenticated as accurate to prove that a particular person was in their vehicle or at a particular destination at a certain time. Further, if a vehicle is implicated in a crime, the vehicle's logs can be examined to determine who the driver was and where they had gone before and after the crime scene. Further, such a system will reduce drunk drivers since it can be configured to prevent drivers who are intoxicated from driving. This can be done by using the same retinal or biometric scanner that is used for the initial biometric identification.

The system is designed to be user friendly and easy to operate. When a person buys a car the seller of the vehicle will grant them access. This may be done by performing a change of ownership command. The original owner, or car dealer, would identify themselves to the vehicle, such as through the biometric or retinal scanner, and then notify the system (preferably through voice-activated commands) that they are transferring ownership to a new person. They would then step out of the vehicle and the new person would enter the vehicle to perform their biometric identification and/or swipe their driver's license or insurance card. The system could then delete the old owner's rights and grant rights to the new owner.

A current owner of the vehicle can also add new drivers. For example, a spouse can add their significant other. This could be performed by the current owner verifying his biometric information and selecting an option (preferably through voice activated commands) to add a new driver. The current owner could also specify what rights the new driver would be entitled to. For example, the rights could be restricted to particular speeds, could restrict whether the new driver is allowed to add additional new drivers, and may select an expiration date for the new driver's privileges. The new driver would then sit in the driver's seat, perform a biometric authentication, and the information would be saved to the system's memory.

As envisioned, certain embodiments of the present invention include using a biometric device for the dual purpose of providing authentication of identity and performing a state test. A retinal scanner may used, for example, to identify not only who a particular driver is, but also to assure that they are not drunk. When individuals drink, the blood vessel patterns in their eyes may swell or change. When an individual is originally added to the vehicle their retinal scan would likely capture their blood-vessel pattern in a nonintoxicated state. If they are later intoxicated, their blood vessel pattern would not match their original, stored, blood-vessel pattern. As such, the retinal scanner could therefore be used not only for identification, but also to determine that an individual is intoxicated. Similarly, a camera and light can be used to perform a pupil dilation test while also recording the identity of the individual. The light may be the dome light or a light on the visor.

The original biometric information may also be stored on the verifiable credential. A retinal scan or fingerprint scan, for example, could be taken at the Department of Motor Vehicles or another authorized location and stored on the credential. This stored and verified credential could then be cross-checked against the biometric information obtained when the vehicle is started to guarantee that the driver of the vehicle is the person who has the valid insurance and driver's license.

Where used for parental control, the system may be customized at the request of a parent. In one embodiment, the system identifies a pin-code or password with the parent. Any driver who fails to enter the pin-code will be treated as a child.

A parent may set hours of the day that the vehicle may be driven by entering the information on a touch screen display, through a keyboard, with voice activated commands, by pre-programming the information on another computer and communicating the information to the system, or through a wireless communications link. The system is dynamic and can allow parents to remotely control aspects of the vehicle. A communications link may be opened so that the parents can talk to the driver or the parents may remotely enforce driving restrictions including setting a maximum speed or requiring the vehicle to follow a particular route. This may include an automated driving system or providing an indicator when the child has gone off-route. The system may also allow the radio to be remotely controlled or a camera to be initiated that displays the road or passenger compartment to the parents through the wireless connection, such as by using a webcam. If a parent wishes to remotely access the system they may be required to enter a pin-code on their telephone or speak a password. If done through a computer link, they may be required to perform a biometric identification or enter a password on their computer. Once a parent has been granted remote access they may be permitted to perform any function as if they were inside the vehicle.

FIG. 1 shows a block diagram of a driver's card identification system and/or a system of preventing use (or unauthorized use) of a vehicle by an operator (or driver) of the vehicle according to an embodiment of the present invention.

As shown in FIG. 1, the system 10 includes a control module (or system controller) 16, a biometric authenticator 12, a state detector 14, and/or a credential authenticator (or sensor) 18. The biometric authenticator 12 is coupled to the control module 16. The state detector 14 can be a substance detecting sensor (or detecting device) adapted to provide a substance level in the operator to the control module 16. Here, the control module 16 is adapted to communicate a driving restriction to the vehicle if the substance level in the operator is above a tolerance level or if the operator is not authenticated by the authenticator 12.

Also, in one embodiment of the present invention, the substance level is determined at an extremity of the operator, the operator is also authenticated at the extremity, and the extremity is selected from the group composed of finger, thumb, toe, ear, palm, sole, foot, hand, and/or head.

In one embodiment, the control module 16 is further adapted to communicate with the vehicle to permit the vehicle to start if the operator has been authenticated by the authenticator 12 and the substance level in the operator is not above the tolerance level. Also, as shown in FIG. 1, the authenticator 12 may be a fingerprint authenticator, a face recognition authenticator, a hand-geometry authenticator, a voice authenticator, etc. In one embodiment, the authenticator 12 includes a fingerprint sensor (or scanner), and the substance level in the operator is determined in-vivo at a tissue within the finger of the operator.

In one embodiment, the substance detecting sensor is adapted to detect an alcohol level in the operator. Here, the substance detecting sensor may include a broadband (or wideband) detector (e.g., a single photodiode detector) described in more detail below. In addition, as described in more detail below, the substance detecting sensor may include a broadband light source and a wavelength filtering system between the broadband detector and the light source. The wavelength filtering system and the broadband light being configured to direct a light beam at a specific wavelength band toward the broadband detector. In the context of the present application, the specific wavelength band can refer to one or more wavelengths or wavelengths ranging from one specific wavelength to another specific wavelength. Alternatively, the substance detecting sensor may include a diode or a diode laser configured to direct a light beam at a specific wavelength band toward the broadband detector and described in more detail below.

Referring back to FIG. 1, the credential authenticator (or sensor) 18 adapted to sense a verifiable credential of the operator is coupled to the control module 16. Here, the control module 16 is adapted to verify that the operator authenticated by the authenticator 12 matches the verifiable credential of the operator. As shown in FIG. 1, the verifiable credential that can be sensed by the credential authenticator includes a driver's license, an RFID tag, a smartcard, a credit card, a key ring including an infrared (IR) adapter, and/or an under-skin implant.

Figure 2:
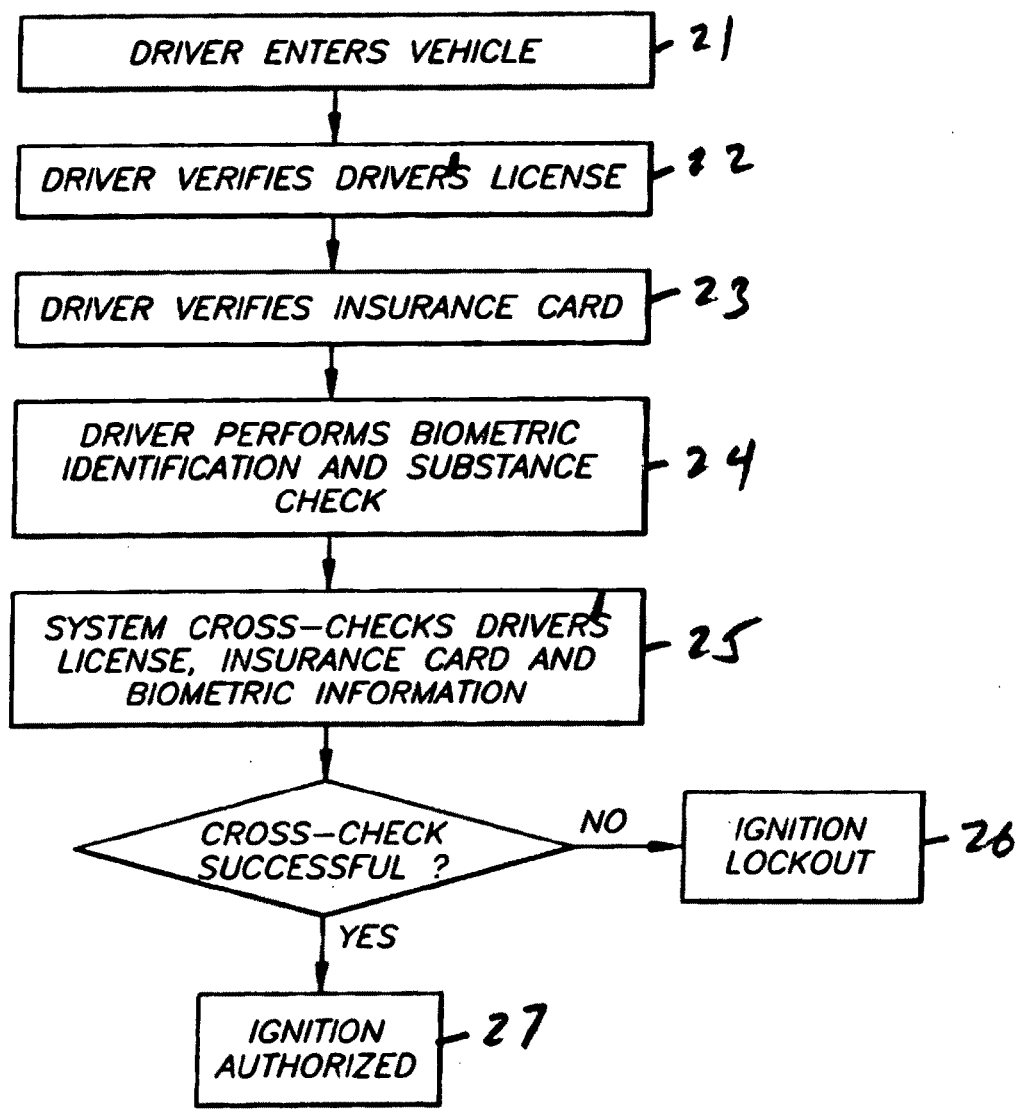
FIG. 2 shows a flowchart of process blocks associated with a driver's card identification system and/or a system of preventing use (or unauthorized use) of a vehicle by an operator (or driver) of the vehicle pursuant to aspects of an embodiment of the present invention.

FIG. 2 shows a flowchart of process blocks associated with a driver's card identification system and/or a system of preventing use (or unauthorized use) of a vehicle by an operator (or driver) of the vehicle according to an embodiment of the present invention. As shown in FIG. 2, the operator or driver enters the vehicle with the system (e.g., the system 10 of FIG. 1) in block 21. In block 22, the driver verifies his driver's license to the system. In block 23, the driver verifies insurance card to the system. In block 24, the driver performs biometric identification and substance check with the system. In block 25, the system cross-checks the driver's license, insurance card, and biometric information. If the cross-check is unsuccessful, a control module of the system (e.g., the control module 16 of FIG. 1) communicates (or issues) a driving restriction, e.g., an ignition lockout, to the vehicle in block 26. By contrast, if the cross-check is successful, the control module communicates with the vehicle to permit the vehicle to start or to authorize ignition (e.g., issues an ignition authorized command) in block 27. Here, the controlled vehicle may include a vehicle selected from the group consisting of an aircraft, a mass transit vehicle, a watercraft, a piece of industrial equipment, and a piece of heavy machinery and equipment FIG. 3 shows a visor mounted biometric device 30 according to an embodiment of the present invention. Here, the visor mounted biometric device 30 may be included in the biometric authenticator 12 of FIG. 1, and coupled with the control module 16 of FIG. 1 via a hinge with wires 31.

As envisioned, an embodiment of the present invention provides an enhanced system and method for biometric and/or substance detection. In one embodiment, a system identifies a person using biometric techniques and also checks for the presence of substances in the body such as alcohol through the use of non-invasive techniques such as Near Infra-Red (NIR) spectroscopy, Raman Spectroscopy, Photoacoustic Spectroscopy, Scatter Changes, Polarization Changes, Mid-Infrared Spectroscopy, and/or Narrowband Detection.

An embodiment of the present invention envisions a design to integrate the two, ordinarily separate, functions of biometric identification and substance detection resulting in additional functionality and lower cost. Such a system may be readily capable of integration into existing and future applications for access control, improved safety, and equipment/vehicle operation.

Substances may be detected in the vascular system by measuring the spectral pattern in the Near IR range which allows quantitation of substances. For example, substance detection through noninvasive techniques may be performed by analyzing the changes in the water molecules of the vascular system with a spectrometer.

As envisioned, other embodiments of the present invention provide a system that includes an interface to an external hardware device or to a software application. The information may be provided to a multitude of suitable applications and/or systems as discussed above and in more detail below. The system, when integrated with some of the suitable applications and/or systems, could provide information to a main processing function that would then perform a decision or computation. For example, the processing function could access a database to determine whether the person is entitled to entry into a controlled area or limit the person in the operational functionality of equipment and/or vehicles. The processing function or system could also notify a third party, such as security personnel, police, or an administrator, or store the information in a database.

As envisioned, an embodiment for the present invention includes positioning of a sensor in a strategic location and informational data transfer to a processor which interprets the data and performs a function based on the data, such as enforcing access restrictions of a person. In the case of a controlled area access, the system could be installed near a door or other means of controlled access point such as a light curtain, optical sensor switches, motion detectors, gates, or human controlled check-points. In the case of operation of equipment or vehicles, the sensor could be installed on the operator's control panel for the equipment or for vehicles, on the dash, clutch, or near the area of the ignition starter of the vehicle. In the case of an airliner flight deck or airplane cockpit a simultaneous reading of both pilot and co-pilot would be performed in their operational positions.

In one embodiment, the sensor may be coupled to a pad or holder for positioning of a hand or finger. For example, a person using the system may place their finger into a mold or sheath. Upon input of the finger onto or into the device, a scan of biometric data would be performed and the data could be provided to a separate processing point whereupon the data could be matched to an existing database and/or locally within the device's central processing unit with a locally stored or remotely connected database. In a further embodiment, the system could identify the person based on the biometric information and determine if there are substances in their body. Based on this identification and/or substance determination, the system could perform any and all functions such as control doors or access points, record the information, require additional information such as a PIN code, or give the user a message. The noninvasive scan can be performed at any wavelength using any method of noninvasive scanning. An embodiment of the present invention can include an NIR spectroscopy scanner adapted to detect, for example, the presence, type, and magnitude of alcohol, drugs such as THC, or glucose in the case of previously known person's diabetic condition. An analysis could then be performed. NIR spectroscopy can detect drugs and alcohol at a range of about 1000 nm to 2000 nm. Alcohol, for example, may be detected at the wavelengths of about 1700 nm, 1600 nm, and 1300 nm. Other drugs or substances that could alter the cognitive capabilities of the person could also be examined within the limits of the sensor. These results could be used to determine the cognitive capability of the person to perform the functions required either in the area of operation, such as a bank vault, or equipment such as a crane, or heavy equipment, or a vehicle such as an automobile, truck, bus, train or airliner. The results could further be stored in a database for future verification including intoxication or identity. The results could further be sent to a third person for manual verification, especially where the identity or intoxication levels approach programmed ranges. The combined results of the sensor relating to a person's identification and to his/her cognitive capability could be processed to allow/disallow the access or operation of equipment or vehicles.

In a further embodiment, a simultaneous scan could be performed by conducting a source of light, such as NIR light, upon the finger and taking the back scatter of light into a beam splitter that would feed the biometric sensor and/or the substance sensor directly.

In another embodiment, a double beam of light could be impressed upon the finger, for the biometric function, near the extremity and for the spectroscopy nearer the knuckle on the bottom side of the finger where the skin is thinner. In another embodiment, the sliding action of the finger upon a scanning device would provide the biometric identification, and a beam of light, such as NIR light, would be used for the spectroscopy measurement performed on the bottom side of the finger nearer the knuckle.

In one embodiment, the biometric and/or substance detection system of the present invention is small enough to allow it to be positioned for convenient access and strategic location functionality, yet large enough to accept the 3 sigma case largest finger based upon population distribution. The electronic data interface provides an output, such as a standard USB, Ethernet, or serial plug or specialized interfaces for dedicated applications such as in automobiles post-1996 using the OBDC-II interface. Scanned and spectroscopy analyzed data may also be made available to near processing units using blue tooth or to local/long distance processing units through the Internet, such as via the IP protocol, cellular wireless or in remote locations using commercially available satellite communications such as GlobalStar or Iridium. The raw light or data may also be transmitted, for example, through fiber optic cable for analysis at a remote or central sensor. In remote or highly inaccessible applications the sensor could be a standalone unit including the main processor and authenticated person's information in its local database. Power for the operation of the device could either be through the host processing unit's power supply (+3.3 VDC, +5 VDC, +12 VDC, etc.), through AC (100 VAC, 115 VAC, 200 VAC, 230 VAC, etc), through an on-board battery and/or AC charging and/or solar panel charging, such as in remote or highly inaccessible applications.

There are commercially-available devices available for obtaining biometric data for identification purposes. There are devices available, in some form of operational readiness, that can perform and process non-invasive scans. The Iso-Chem NIR Material Analysis System, available from LT Industries, Inc. is a portable NIR analyzer with remotely triggered testing probes. The USB4000, for example, available from Ocean Optics is a spectrometer responsive to 200-1100 nm. The SM241, for example, available from Spectram Products is a compact CCD based spectrometer designed for NIR laser applications with a range of 900 nm to 1700 nm. The OSM-100, for example, available from Newport Corporation is a portable, economical spectrometer that is responsive to from 200 nm to 1700 nm. The Sugartrac is a noninvasive glucose monitor, available from Lifetrac Systems. The TouchPrint Enhanced Definition 3000 Live Scan is a portable biometric scanner and identification device, available from Live Scan Products.

Also, as envisioned, an embodiment of the present invention provides a method for combining biometric identification with substance detection. This may be performed using the system or device as described above or with any other biometric identification system and any other substance detection system. For example, a face scanner or retinal scanner may be used in combination with a substance detector (e.g., a breathalyzer). In an embodiment of the method for combining biometric identification with substance detection, the steps of a biometric scan and a substance detection scan are performed. Additional steps, such as activating the scan, processing the scan, comparing the scans, sending a notification or alarm, activating a recording device, saving the raw data or the processed results, or performing error-checking or a further type of scan may be performed. Additionally, the step of checking the temperature or pulse may be performed to verify that the scan is accurate.

FIG. 4 shows a block diagram of an enhanced biometric and substance detection system and device according to an embodiment of the present invention. As shown, a sheath (or cradle) 100 (e.g., a finger cradle) with a hole at one end 120 for the insertion by an extremity of an operator (e.g., a finger) is provided. A biometric sensor 210 and a substance sensor 220 are included with the sheath 100. In one embodiment, the extremity is selected from the group consisting of finger, thumb, toe, ear, palm, sole, foot, hand, and head.

In addition, the biometric sensor 210 and the substance sensor 230 are respectively coupled to a biometric device (or authenticator) 400 and a substance detection device 500 via leads 300. The biometric device 400 and the substance detection device 500 are coupled to a central processor (or system controller or control module) 700 via leads 600. The central processor 700 may then be coupled to the access control processor 800, which may be coupled to an access control device or interface 900.

Referring to FIG. 4A, in one embodiment, the enhanced biometric and substance detection system and device of FIG. 4 is incorporated within a vehicle 100a. In one embodiment, the vehicle 100a is selected from the group consisting of an aircraft, a mass transit vehicle, a watercraft, a piece of industrial equipment, and a piece of heavy machinery and equipment. In more detail, the vehicle 100a includes the sheath (or cradle) 100 for insertion by the extremity of the operator.

Figure 4B:
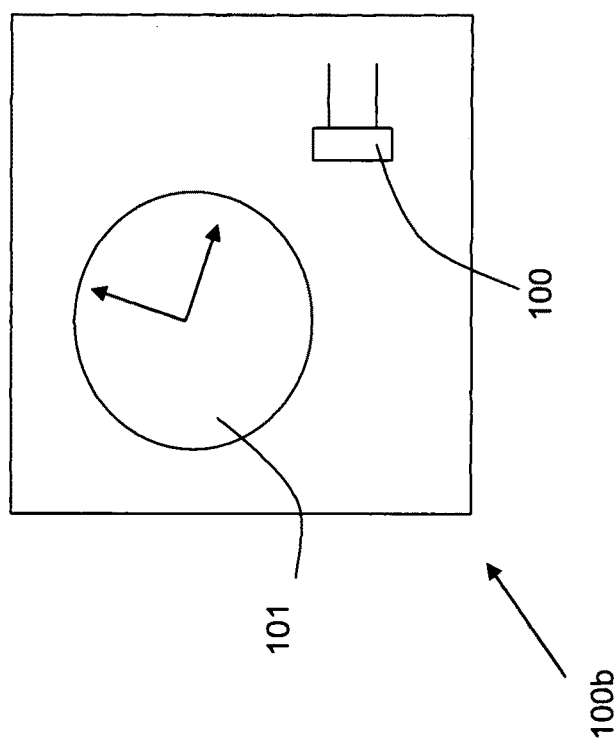
FIG. 4B shows a block diagram of a time clock system including the enhanced biometric and substance detection system and device of FIG. 4 pursuant to aspects of an embodiment of the present invention.

Referring to FIG. 4B, in another embodiment, the enhanced biometric and substance detection system and device of FIG. 4 is incorporated within a time clock system 100b. Here, in one embodiment, the time clock system 100b is adapted to create an alert if the substance level in the operator is above a tolerance level or if the operator is not authenticated by the authenticator. In one embodiment, the time clock system 100b also includes a time clock 101 adapted to determine a time when the alert is created. Also, the central processor (or system controller) 700 may be adapted to communicate with a building security device to permit the operator to access the building security device if the operator has been authenticated and the concentration of the substance is not above a tolerance level. In one embodiment, the central processor 700 is adapted to communicate with the building security device to restrict the operator from accessing the building security device if the operator has not been authenticated or the concentration of the substance is above the tolerance level. The building access device may include the time clock 101 adapted to determine a time when the operator is permitted access to the building security device.

Figure 5:
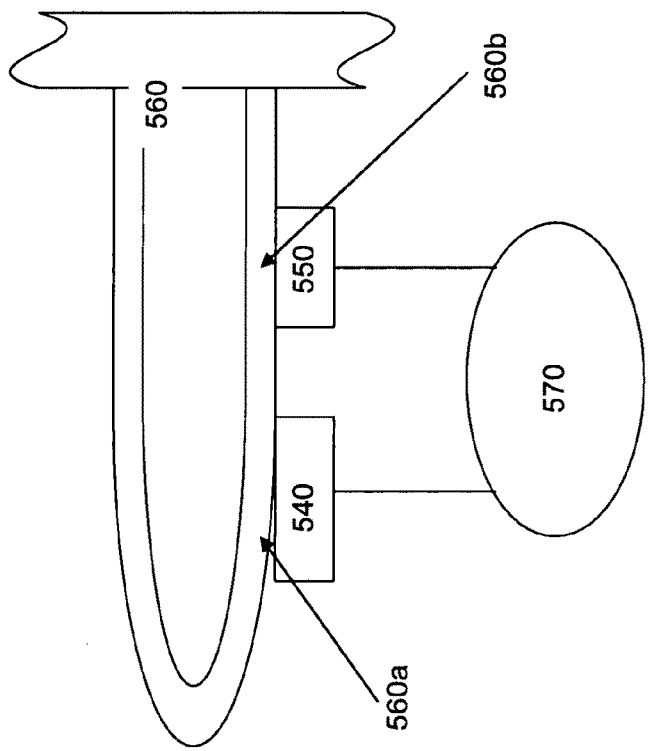
FIG. 5 shows a block diagram of an enhanced biometric and substance detection system and device pursuant to aspects of another embodiment of the present invention.

FIG. 5 shows another embodiment of the present invention. As shown in FIG. 5 a system for preventing use of a vehicle by an operator of the vehicle includes a system controller 570, a biometric authenticator 540, and a substance detecting device 550. Here, the system controller 570 is adapted to detect at least one biometric parameter at a first dermal location 560a of an operator (or at an extremity of the operator) 560 of a vehicle and generate an authentication output indicating that the operator 560 has been authenticated. Here, the first dermal location 560a of the operator 560 is a location capable of biometrically authenticating the operator 560 (e.g. at a fingerprint of the operator or a location where a fingerprint of the operator 560 is at). In addition, the substance detecting device 550 is adapted to detect a level of a substance in the operator 560 at a second dermal location 560b proximate to the first dermal location 560a and generate a level output.

Here, in one embodiment of the present invention, the two detection measurements (i.e., the authentication and the substance detection) take place on cutaneous (or dermal) locations of the operator that are proximate to (possibly adjacent) one another. In the context of the present embodiment, proximate and/or adjacent can be referred to as close enough to substantially preclude circumvention of the test by measuring the substance level of a person other than the one being authenticated.

In addition, referring still to FIG. 5, the system controller 570 operates in response to the authentication output and the level output to selectively restrict use of the vehicle if the operator 560 is not authenticated or the detection output is above a preselected tolerance value.

Also, in one embodiment, the substance detecting device 550 includes a light source and a single broadband detector described in more detail below. Here, a surface (or platform) of the substance detecting device 550 that is coupled to both the light source and the single broadband detector contacts the second dermal location 560b and has an index of refraction that corresponds (or is identical or substantially identical) to that of the second dermal location 560b to reduce or eliminate specular light (i.e., light that did not penetrate into the skin).

As envisioned in embodiments of the present invention, radiation passing through a sample is attenuated depending upon the path length traveled by the radiation and the strength of absorptions at various individual wavelengths for constituents within that particular sample. Recording and mapping the relative strength of the absorption versus wavelength results in a unique absorption spectra for that particular sample.

One application area for spectroscopy is the measurement of tissue attributes or analytes noninvasively. A specific application is the measurement of analytes, such as ethanol, noninvasively for subjects to be screened for substance abuse.

Near-infrared radiation (NIR) offers distinct advantages for measurements in tissue spectroscopy. Optical path lengths greater than one millimeter are readily achieved in the NIR in the therapeutic window of the electromagnetic spectrum. However, influences that interfering chemical species have on the accuracy of analytical determinations (e.g., determinations of ethanol) are issues that need to be resolved. In the context of the present application, the issues that need to be resolved can be referred to as backscatter and selectivity, or the extent to which a method can be used to determine particular analytes in mixtures or matrices without interference from other components of similar behavior.

That is, the primary source of noise is the light scatter that does not bear the complete signature of ethanol in the blood. Human skin has several layers: epidermis, dermis and subcutaneous tissue. Each layer has its own wavelength-dependent absorption and scattering properties. The light undergoes both forward and backscatter as it penetrates the skin, interacts with blood, and comes out. Further complications arise when the skin is not at a constant angle with respect to illumination and collection from sample to sample. Location of the part of the hand may also matter. Thus, a system should reduce or eliminate the amount of initial light scattering by using optical coupling and/or reducing differences in refractive index and/or reducing or eliminating detection of any light that is scattered before reaching the tissue containing the analyte.

Moreover, with respect to detection of the light that is reflected after reaching the tissue containing the analyte, spectral data arising from spectroscopic analysis provides a wealth of detailed information about the identity, structure, concentration or constituents of samples. Spectral data derives from the detected and recorded energy change of a molecule through the emission, scattering, or absorption of a photon. In particular, atoms within a molecular species vibrate back and forth about an average distance. Absorption of light by an atom at an appropriate energy causes the atoms to become excited, elevating the atom to a higher vibration level. The excitation of the atoms to an excited state occurs only at certain discrete energy levels, which are characteristic for that particular molecule. Infrared absorption spectroscopy is particularly useful for performing this type of analysis. In absorption spectroscopy, the net absorption of incident radiation at various wavelengths is measured. However, the system should be able to detect levels of a particular analyte and discriminate between that analyte and others that might have similar characteristics.

As envisioned and to resolve the above described issues, an NIR reflectance instrument was developed to include an illumination source and a spectrometer described in more detail above. The instrument utilized near-infrared radiation in the specific wavelengths ranging from about 1300 nm to about 2400 nm; more specifically, from about 1400 nm to about 1500 nm, from about 1650 nm to about 1750 nm, and/or from about 2200 nm to about 2400 nm. In one embodiment, a specific wavelength band at about 1450 nm is utilized. These wavelength ranges are of prime interest for making noninvasive alcohol measurements because they contain combination and overtone bands for a wide variety of chemical species including alcohol and other organic molecules present in tissue. The NIR spectrum of ethanol has pronounced features in these wavelength ranges due to bands of C—H bends and C—H stretches of the alcohol and other organic molecules and/or the combination band of the 0-H bends and 0-H stretches of alcohol and other organic molecules.

These wavelength ranges should also be less influenced by tissue scattering effects when compared to higher wavelength regions, as the effects of tissue scattering increase with wavelength. This has significant implications in tissue measurements because scattering effects can cause substantial spectral variability both within and between human subjects.

Figure 6:
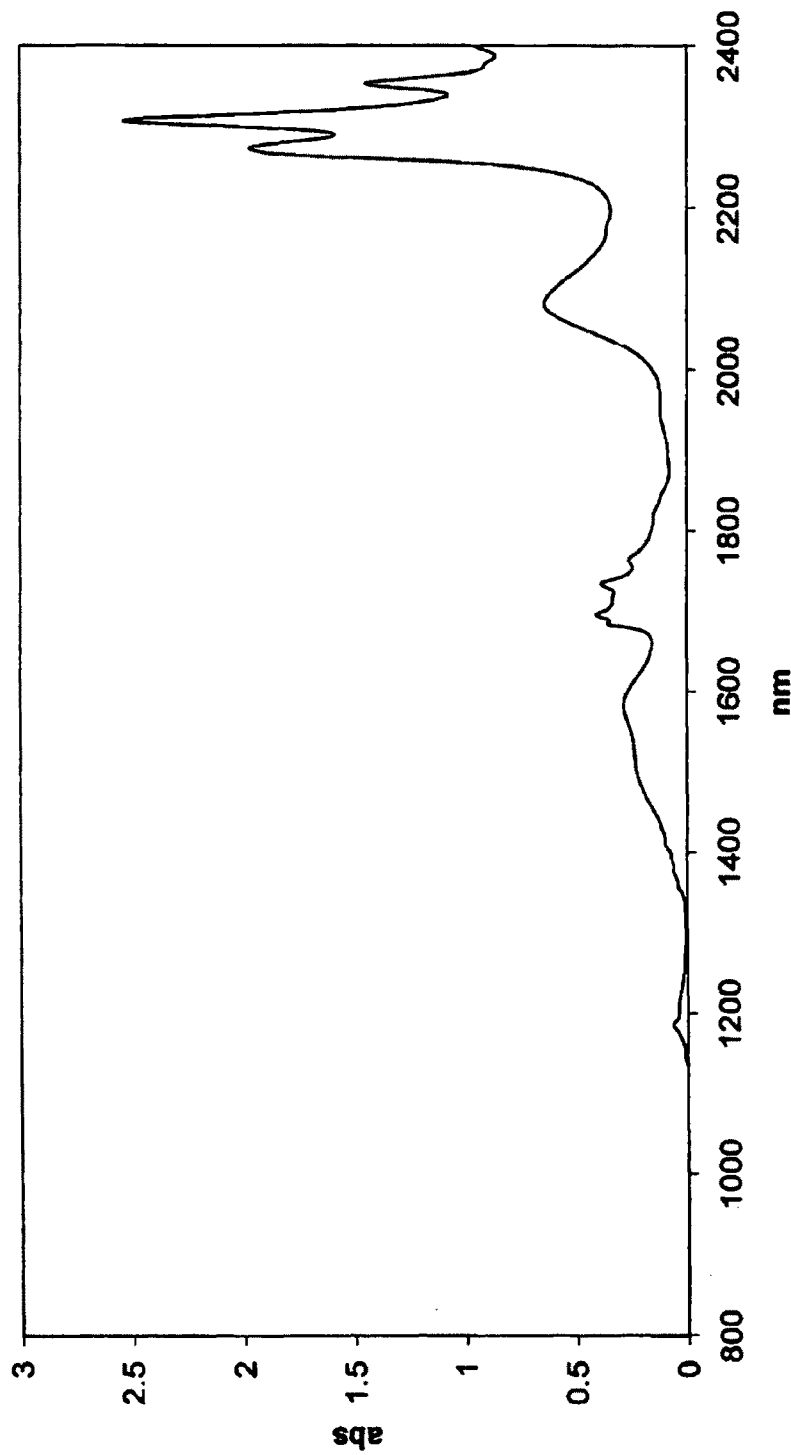
FIG. 6 shows a spectrum of 100% ethanol at specific wavelengths ranging from 800 nm to 2400 nm collected using a research grade NIR spectrometer pursuant to aspects of an embodiment of the present invention.

Referring to FIG. 6, a spectrum of 100% ethanol with a 1 mm sampling path at specific wavelengths ranging from 800 nm to 2400 nm were collected using a research grade NIR spectrometer. As can be derived from FIG. 6, the specific wavelengths ranging from about 1300 nm to about 2400 nm are of interest. Also, the specific wavelengths ranging from about 1400 nm to about 1500 nm, from about 1650 nm to about 1750 nm, and/or from about 2200 nm to about 2400 nm are of particular interest.

Figure 7:
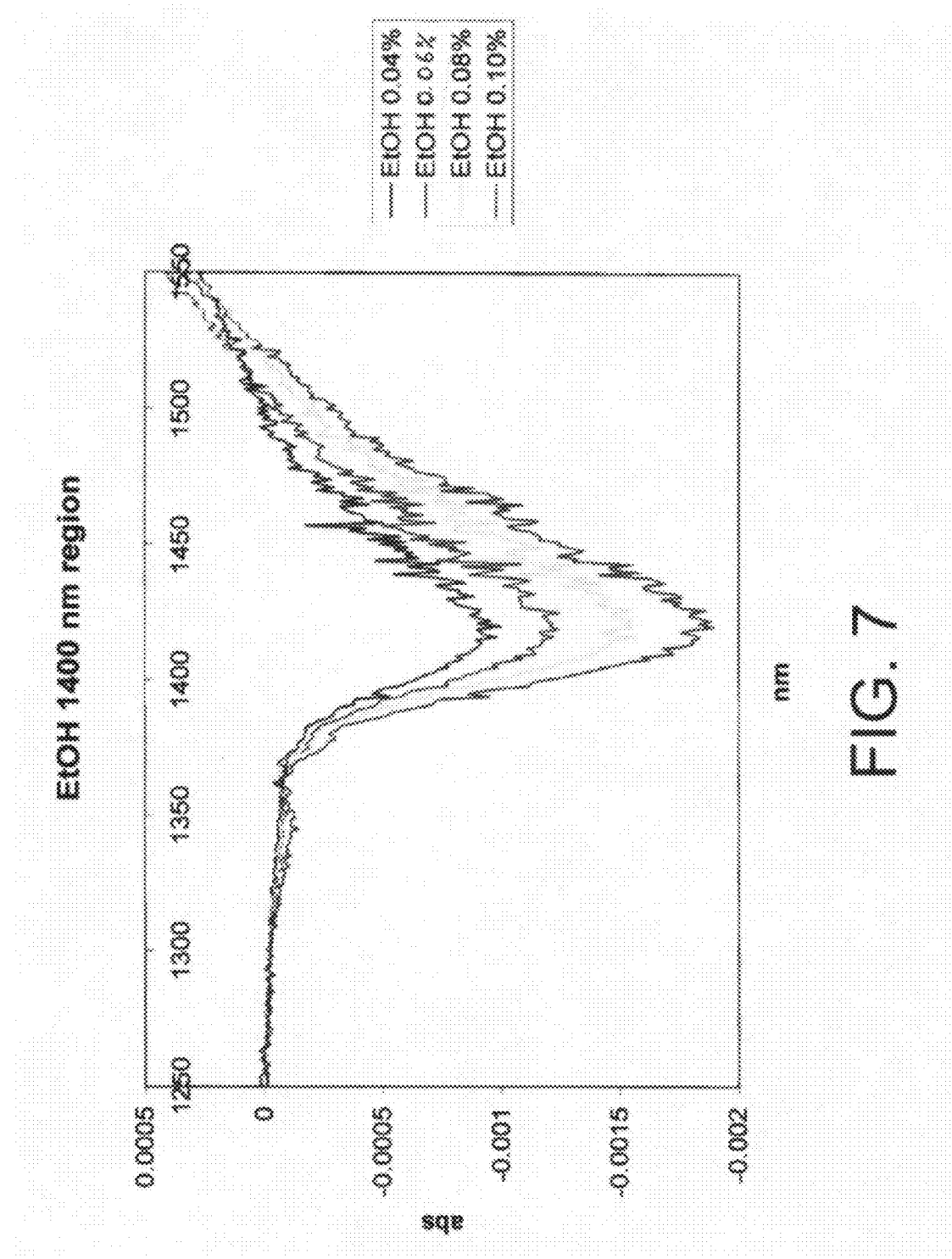
FIG. 7 shows spectra of 0.10%, 0.08%, 0.06%, and 0.04% ethanol in water at specific wavelengths ranging from 1400 nm to 1500 nm collected using a research grade NIR spectrometer pursuant to aspects of an embodiment of the present invention.

As shown by the research grade NIR spectrometer data in FIG. 7, the research grade NIR spectrometer is capable of distinguishing 0.10%, 0.08%, 0.06%, and 0.04% ethanol in water at the specific wavelengths ranging from about 1400 nm to about 1500 nm. As can be derived from FIG. 7, the specific wavelength band at about 1450 nm is of particular interest.

Figure 8:
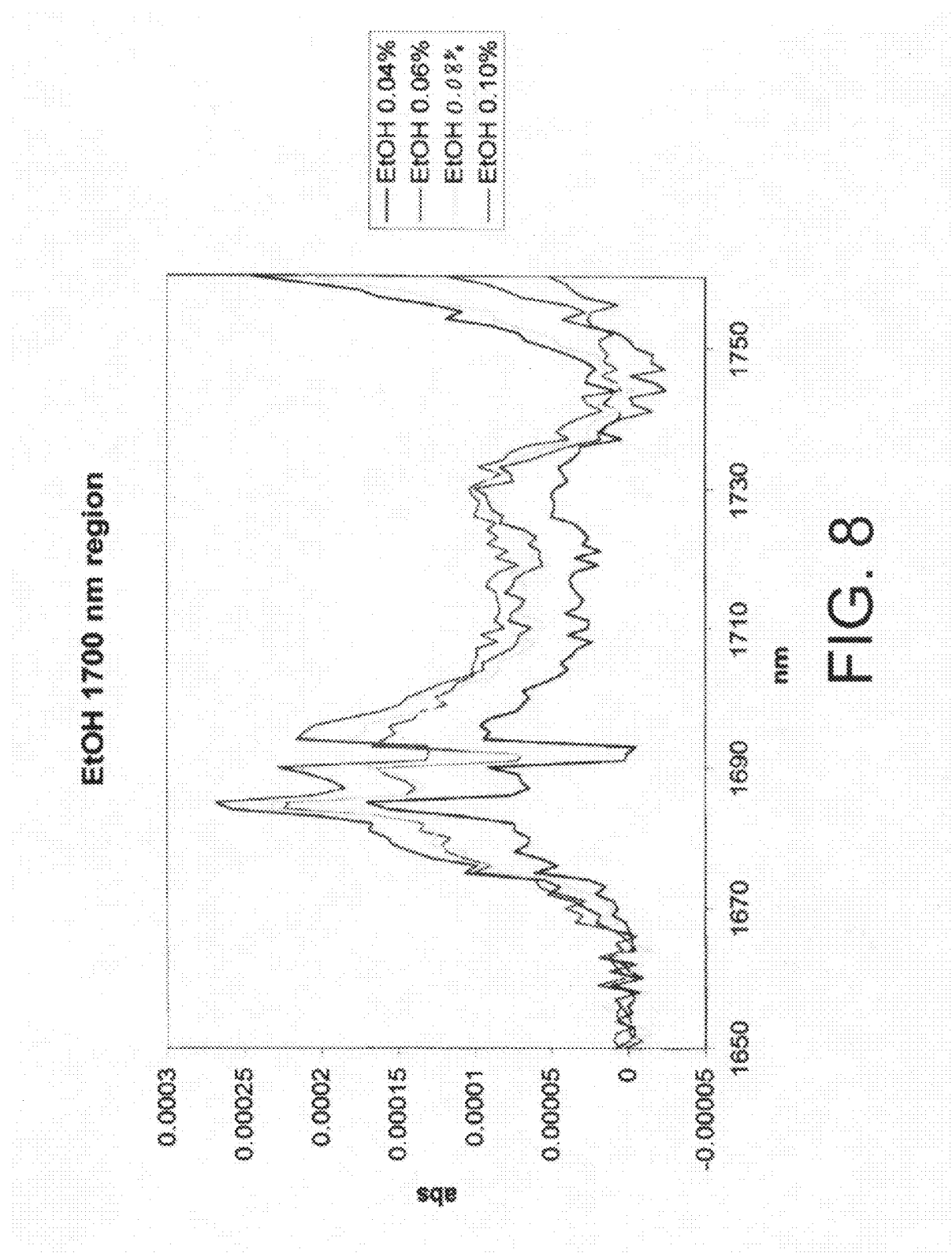
FIG. 8 shows spectra of 0.10%, 0.08%, 0.06%, and 0.04% ethanol in water at specific wavelengths ranging from 1650 nm to 1750 nm collected using a research grade NIR spectrometer pursuant to aspects of an embodiment of the present invention.
Figure 9:
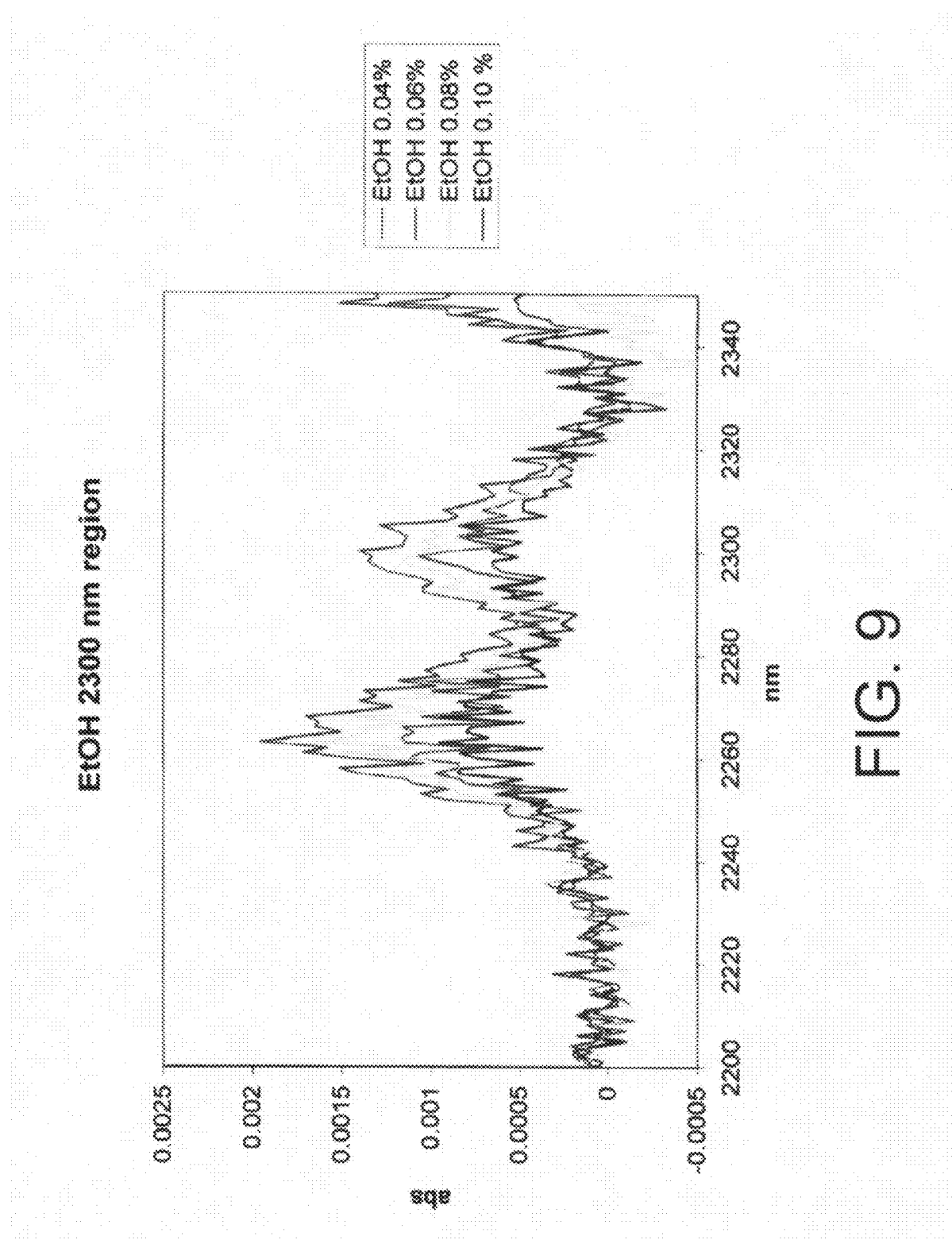
FIG. 9 shows spectra of 0.10%, 0.08%, 0.06%, and 0.04% ethanol in water at specific wavelengths ranging from 2200 nm to 2400 nm collected using a research grade NIR spectrometer pursuant to aspects of an embodiment of the present invention.

In addition, as shown in FIGS. 8 and 9, the research grade NIR spectrometer is capable of distinguishing 0.10%, 0.08%, 0.06%, and 0.04% ethanol in water at the specific wavelengths ranging from about 1650 nm to about 1750 nm, and at specific wavelengths ranging from about 2200 nm to about 2400 nm. In FIGS. 8 and 9, the specific wavelength bands at about 1700 nm and at about 2300 nm are of particular interest.

To investigate ethanol sensitivity and, more importantly, selectivity, samples should be constructed containing ethanol, glucose, creatinine, urea, water, and microspheres. The microspheres (e.g., polystyrene microspheres) provide an optical scattering medium that yields a reflectance signal whose intensity is similar to that of red-blood cells. Thus, the samples provide conditions that will mimic blood under a variety of circumstances. The concentration ranges of the analyte of interest, ethanol for example, and those of possibly interfering analytes should mirror those observed in a healthy subject population (i.e., human and/or biological ranges). The whole universe of samples of the concentrations should then be reduced using a suitable statistical modeling, such as a Latin hypercube of a suitable level. In one embodiment, a set of a 7-level Latin hypercube design is used to provide maximum inter-analyte correlations with manageable sample sizes.

Intensity spectra are then collected from the samples (or in-vitro) of various concentrations. The collected spectra are then analyzed to determine the wavelength ranges that are needed and the wavelength ranges that can be eliminated for proper ethanol analysis. Human (or in-vivo) testing should then be performed to validate the statistical modeling and design with respect to ethanol, the model should be able to detect ethanol in blood down to about 0.05% with an accuracy of preferably plus or minus 0.02%, more preferably plus or minus 0.01%.

The validated statistical model for analyzing the data then provides the spectral bands for the sensor. As envisioned according to one embodiment of the present invention, three (3) non-overlapping wavelength regions in the NIR ranges are utilized. Each wavelength region should have from 3 to 4 non-overlapping sub bands. Each of these wavelength bands has about a 25 nm bandwidth.

Figure 10A:
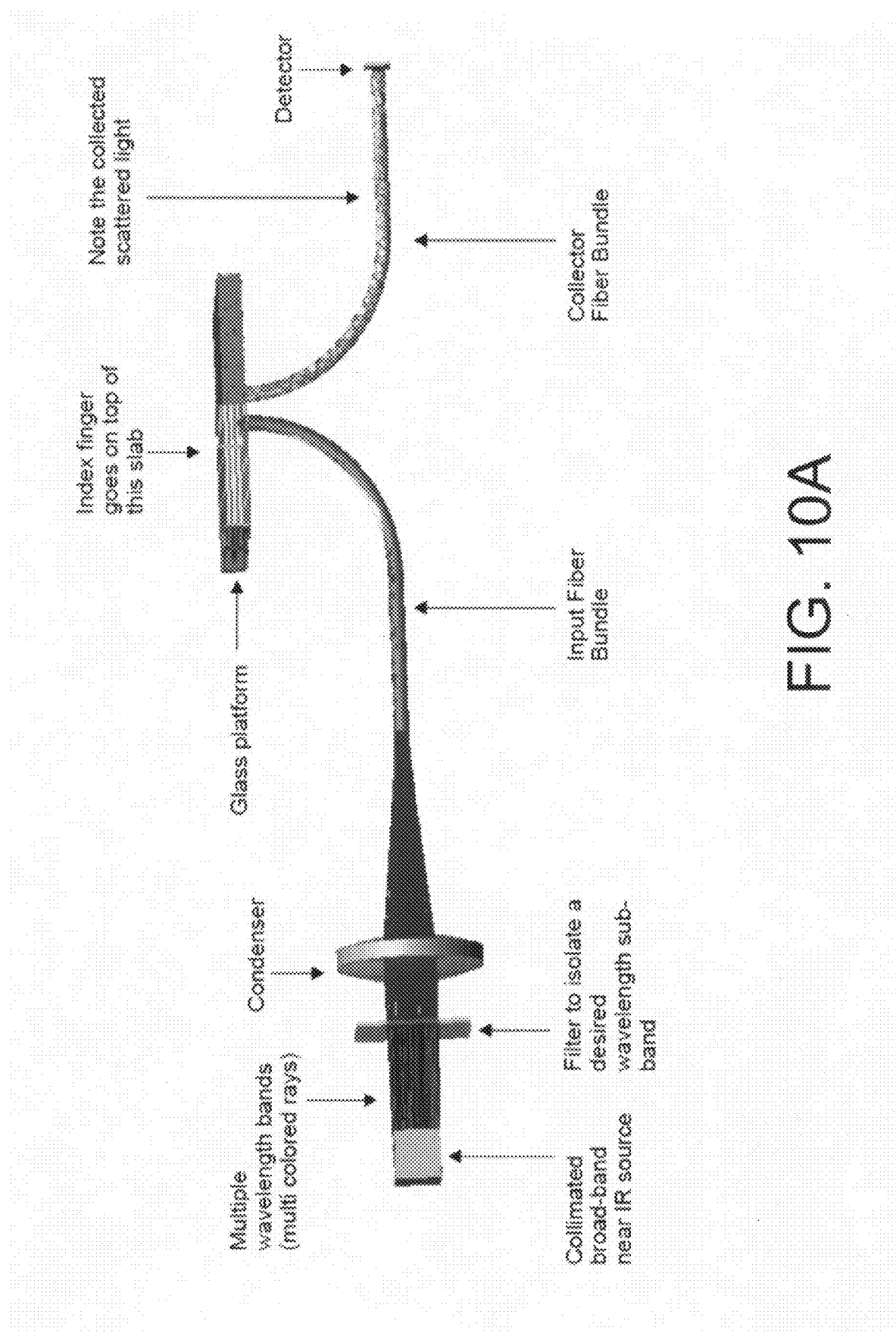
FIG. 10A shows an optical substance detector configuration according to an embodiment of the present invention.

FIG. 10A shows an optical substance detector configuration according to an embodiment of the present invention. In more detail, the detector includes a light source (collimated broad-band IR source) for providing a light beam having multiple wavelength bands (shown as multiple colored rays). The light beam is directed to a filter adapted to isolate a desired or specific wavelength band (or sub-band). The isolated light beam is then directed to a condenser and passes through an input fiber bundle (or plastic light guide or suitable light guide) to a glass platform (or finger cradle or index finger slab) in which a test sample (e.g., a finger or an extremity selected from the group consisting of finger, thumb, toe, ear, palm, sole, foot, hand, and head) is placed thereon. In one embodiment, the glass platform has an index of refraction that corresponds (or is identical or substantially identical) to that of the test sample to reduce or eliminate specular light (i.e., light that did not penetrate into the skin of the test sample). In addition, the glass platform can be formed of a 1 mm thick fused silica glass, preferably with a non-reflective coating. The light beam that has been reflected (or diffusely reflected) from the test sample (e.g., the finger) is collected by a collector fiber bundle (or plastic light guide or suitable light guide) coupled to the glass platform. A detector is then used to detect the light (or light intensity) diffusely reflected back from the test sample and collected by the collector fiber.

Figure 10B:
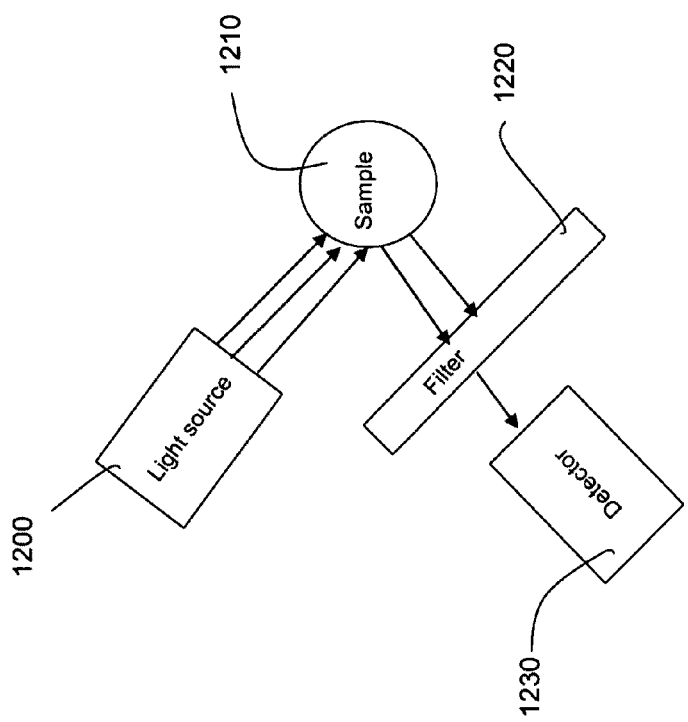
FIG. 10B shows an optical substance detector configuration according to another embodiment of the present invention.

Alternatively, FIG. 10B shows an optical substance detector configuration according to another embodiment of the present invention. In more detail, the detector here includes a light source 1200 for providing a light beam (or beams) having multiple wavelength bands (shown as multiple rays).

The light beam(s) is (or are) directed to a test sample 1210 (e.g., a finger or an extremity selected from the group consisting of finger, thumb, toe, ear, palm, sole, foot, hand, and head). In one embodiment, the light source 1200 has a parabolic or elliptical reflector to focus or direct the light beam. The light beam(s) that has been reflected (or diffusely reflected) from the test sample (e.g., the finger) is passed through a filter 1220 adapted to isolate a desired or specific wavelength band (or sub-band). A detector 1230 (e.g., a single broadband detector) is then used detect the light (or light intensity) diffusely reflected back from the test sample and filtered by the filter 1220. As such, in FIG. 10B, the filter 1220 is shown to be disposed closer in distance to the detector 1230 than to the light source 1200. Here, in FIG. 10B, since the light beam(s) from the light source 1200 is not filtered until it has been reflected back from the sample 1210 (i.e., the filter 1220 is at the detector end), a relatively large amount of light is directed to and diffusely reflected back from the sample 1210.

The present invention, however, is not limited to the filter positioning embodiments of FIGS. 10A and 10B. For example, to increase wavelength selectivity and/or to reduce signal to noise ratio, an embodiment of the present invention envisions configuring a first filter to be disposed at the light source end (e.g., the filter of FIG. 10A), and a second filter (e.g., the filter 1220) to be disposed at the detector end.

In one embodiment, the light source can be an incandescent light source, such as tungsten-halogen lamp, xenon arc lamp, mercury arc lamp, LED(s), and/or diode laser(s), which has abundant IR. In one embodiment, the light source is collimated prior to filtering using a narrow bandpass optical filter. The filter adapted to isolate a desired or specific wavelength band (or sub-band) can be part of a filter wheel that can be rotated to bring different filters in position. This allows collecting data from multiple wavelength bands. The condenser optics are used to focus light into the fiber, which carries the light to the optical tissue (e.g., the finger). The collector fiber collects the scatter signal from the tissue and carries it to the detector.

Also, various suitable types of fiber bundles may be used, such as a ring type light guide, a straight type light guide, a bifurcated type light guide, etc. In addition, instead of using fiber bundles, an embodiment of the present invention envisions the use of other suitable types of light guides, such as plastic light guides.

In one embodiment, an optical substance detector includes a light source including a halogen lamp and a fiber optic bundle attached to the halogen lamp to illuminate a test sample (e.g., an area of the test sample) with a configured wavelength filtering system. The wavelength filtering system can include various suitable types of filter, such as, interference, band pass, absorption, dichroic, monochromator grating, etc. The wavelength filtering system according to one embodiment is disposed closer in distance to a detector (e.g., a single broadband detector) than to the light source. The desired wavelength bands are reflected back to the detector. Through an evaluation involving a statistical modeling analysis, the test sample's blood alcohol concentration (BAC) is determined with respect to a legal limit to operate a vehicle and, if the BAC is not within the legal limit, the vehicle is disabled. In one embodiment, the statistical modeling is a Latin hypercube of a suitable level. However, the present invention is not thereby limited. For example, any suitable multivariate statistics or multivariate statistical analysis in statistics that can be used to describe a collection of procedures which involve observation and analysis of more than one statistical variable at a time can be used.

Another embodiment of the present invention provides a light source (e.g., a diode laser) at a specific (single) wavelength band in the infrared (IR) or near IR wavelength range (s) and a broadband detector for non-invasive and/or in-vivo testing of a concentration of a substance in a tissue of a person. The substance can be alcohol, more specifically, ethanol, and the tissue can include a person's blood.

Figure 11:
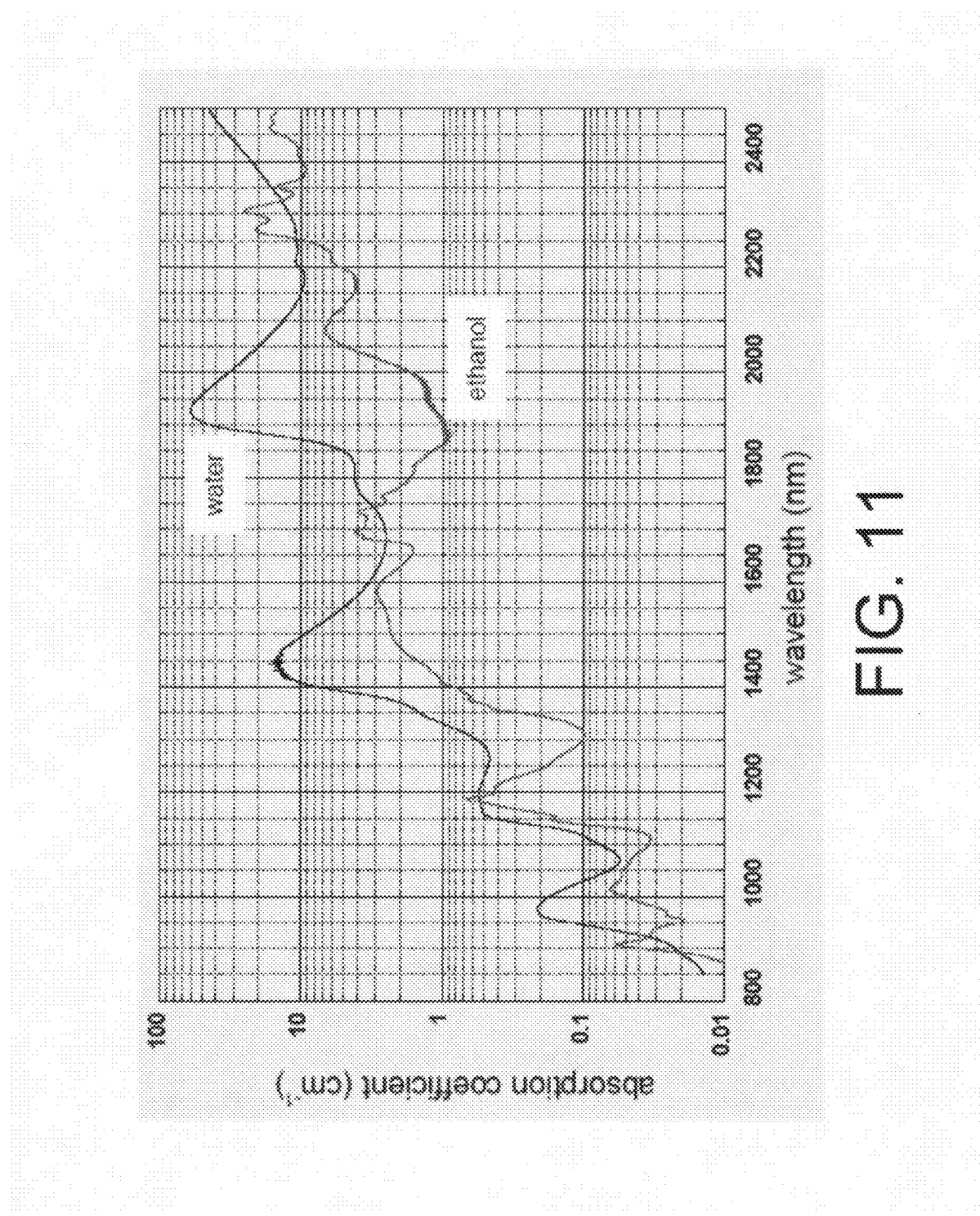
FIG. 11 shows ethanol and water optical absorption from 800 to 2400 nm pursuant to aspects of an embodiment of the present invention.

In more detail, FIG. 11 shows ethanol and water optical absorption from 800 to 2400 nm. As such, an embodiment of the present invention provides an optical method for non-invasive and/or in-vivo ethanol testing that exploits the difference in optical absorption between ethanol and water, and, because blood is primarily formed by water, a concentration of ethanol in the blood can be determined. As in all manner of absorption spectroscopy the amount of light absorption at a specific wavelength is used to positively identify the chemical compound in the solvent. A given aliquot of water and ethanol will absorb less light at certain wavelengths then an equivalent aliquot of water alone. At other wavelengths the phenomenon is reversed and the ethanol water mix will absorb more light.

Figure 12:
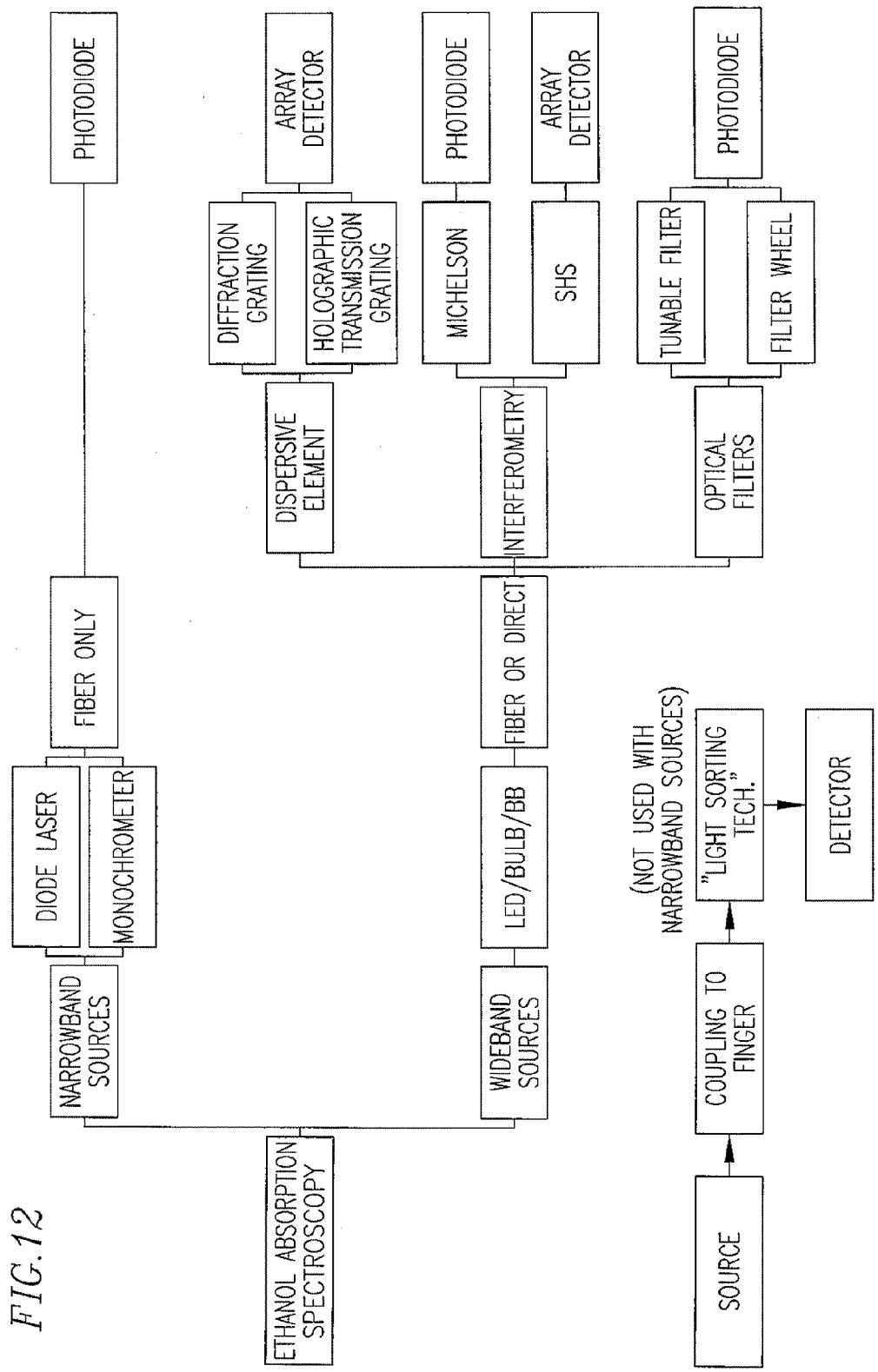
FIG. 12 shows a block diagram of a variety of technologies that can be used pursuant to aspects of an embodiment of the present invention.

It is possible to make these measurements using a variety of technologies at several different wavelengths as shown in FIG. 12. In one embodiment of the present invention, a wavelength at about 1000 nm, a wavelength at about 1310 nm, a wavelength at about 1550 nm, and/or a wavelength at about 1900 nm were selected, as regions (or regimes) where ethanol is more transmissive, (less absorptive) than water. Spectral regions at about 904 nm, about 1700 nm, and about 2300 nm were also selected, as regions (or regimes) where ethanol is less transmissive than water.

Figure 13:
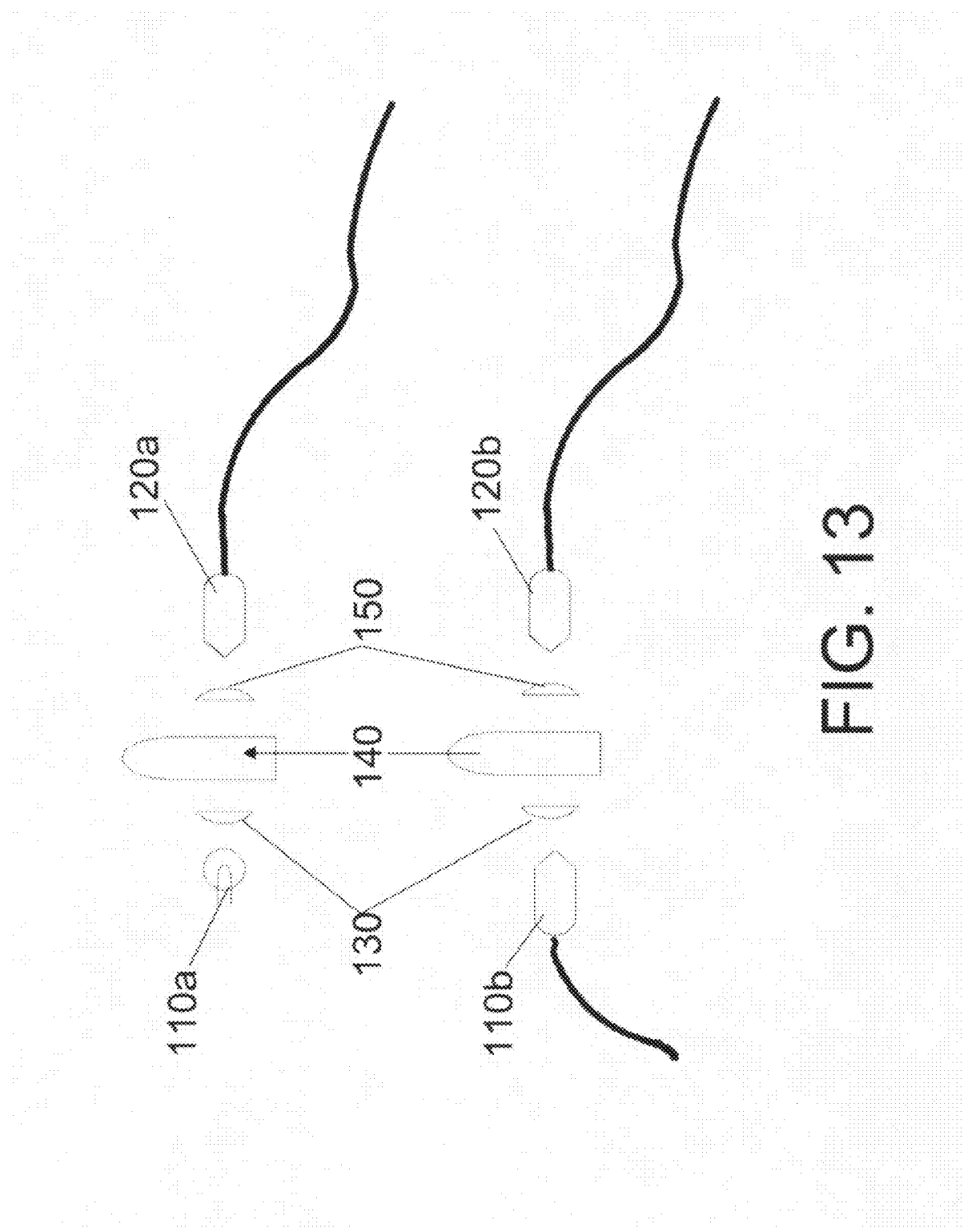
FIG. 13 shows a light source, a collimating lens, a finger, a reimaging lens, and a fiber pursuant to aspects of an embodiment of the present invention.

Referring to FIG. 13, a first distinction of the technologies that may be used to make the above described measures is the type of illumination, narrow-band or broadband. Most absorption spectroscopy technologies use a white light or broadband light source and then use either an interferometer or diffraction grating to "sort" the light into spectral bins. These systems have some common elements, coupling of finger to illumination either with a fiber or directly (FIGS. 13 and 14) and the final optical signal detection technology, which will be composed of either a linear CCD array or a photodiode detector.

In more detail, FIG. 13 shows illumination is on the left hand side. Here, the illumination is provided from a self-contained light source, bulb, blackbody etc. 110a or a fiber which is coupled to a remote light source 110b. To the right of the light source 110a, 110b is a collimating lens 130 that renders parallel the light as it traverses through or into a finger (e.g., middle finger) 140 to a reimaging lens 150, which focuses the "sampling beam" onto a fiber 120a, 120b that is connected to a diffraction grating spectrometer or some type of interferometer.

Figure 14:
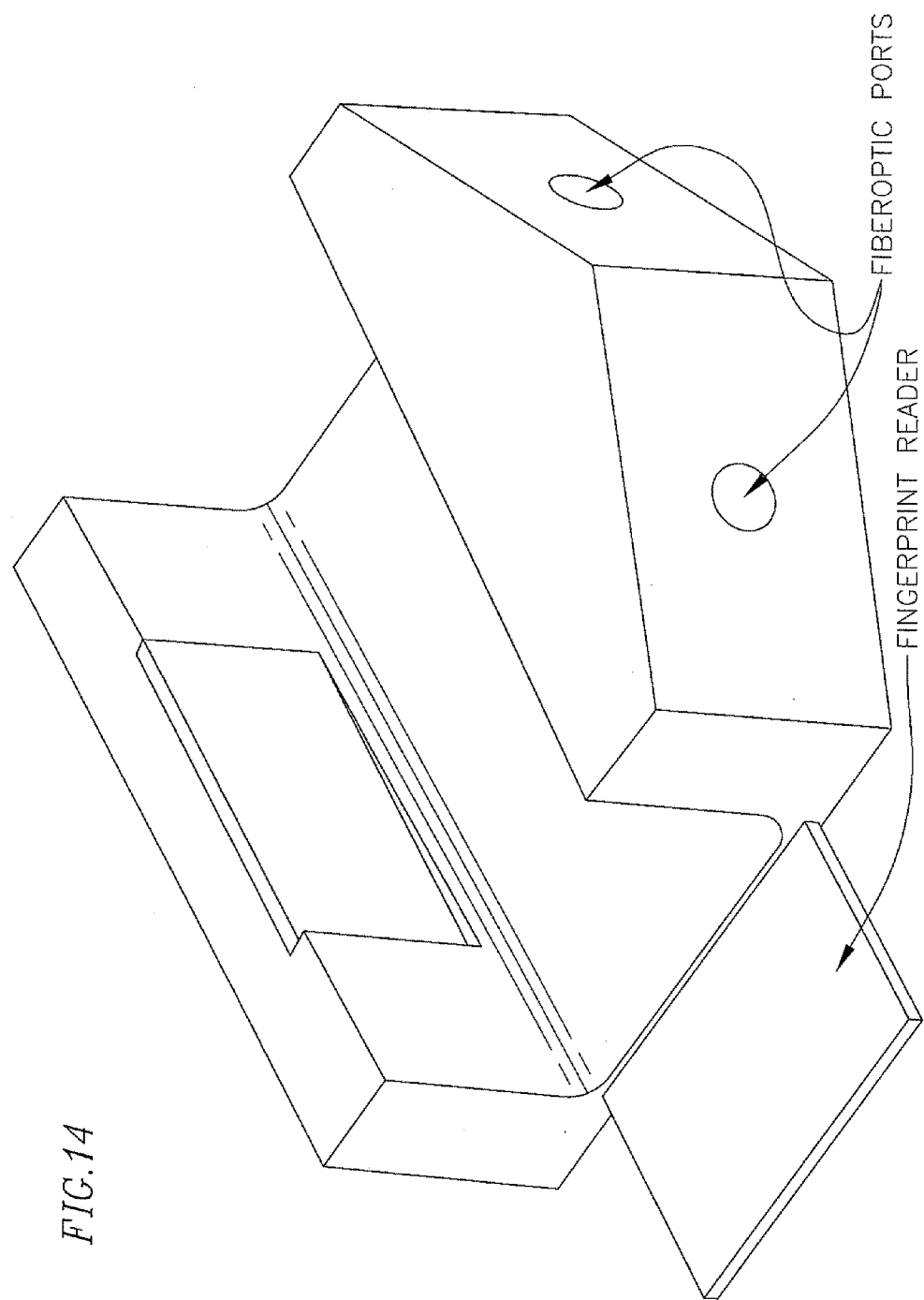
FIG. 14 shows a schematic of a finger sensor with integral fingerprint screen pursuant to aspects of an embodiment of the present invention.

FIG. 14 shows a schematic of a finger sensor with integral fingerprint screen according to an embodiment of the present invention. The two ports (Fiberoptic Ports) can be used for either fiber coupling optics or direct detection (i.e. a broadband detector or an InGaAs detector could be installed directly in one of the ports) to allow light from a light source (e.g., via another one of the light port) to be detected via, e.g., diffuse reflectance. That is, in FIG. 14, an incident beam of light can be directed from a first side of the finger toward a second side of the finger, and the broadband detector can be configured to measure the portion of the incident light beam transmitted through a portion of the tissue and reflected back to the first side of the finger. Also, other sensors, e.g., temperature, surface contaminant, etc., can be installed on the bottom of this unit.

Figure 15:
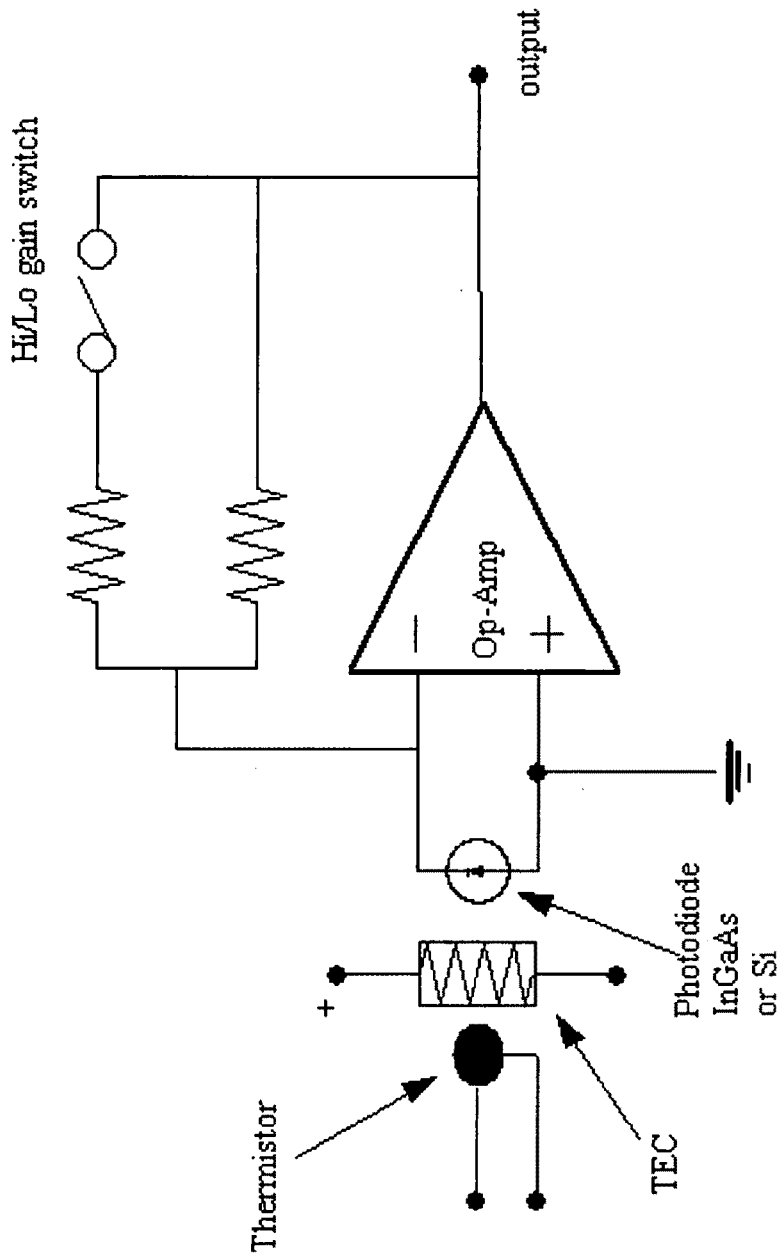
FIG. 15 is a schematic of a photodiode with a transimpedance amplifier and thermal control as envisioned pursuant to aspects of an embodiment of the present invention.

FIG. 15 is a schematic of a photodiode with a transimpedance amplifier and thermal control as envisioned according to an embodiment of the present invention. The photodiode detector schematic demonstrates the extant detector system. An InGaAs or Si photodiode is coupled to a trans-impedance amplifier. The detector is thermoelectrically cooled while an integral thermistor monitors the temperature. However, the present invention is not thereby limited. For example, instead of using an InGaAs detector as the detector (or the infrared detector), other embodiments of the present invention can use a PbS detector, a PbSe detector, an InAs detector, an InSb detector, a HgCdTe detector, etc.

As discussed above, absorption spectroscopy can be used to quantitatively identify a substance through the application of Lambert-Beer's law, usually referred to as Beer's law, as shown by the equation below.

$$A(\lambda_i) = -\log\left(\frac{I(\lambda_i)}{Io(\lambda_i)}\right) = \sum_k \alpha_k(\lambda_i) \cdot C_k \cdot d$$

where, the quantity of a substance A is proportional to the log of the ratio of the intensity, I, as a function of wavelength pre and post absorber. Which in turn is a function of the mass path d and the absorption coefficient $\alpha$. These quantities are all wavelength dependent so the usual approach is to take spectral measurements over many wavelengths, as seen in FIG. 11, which covers from 800 to 2400 nm. However, a task at hand was to exploit these differences in absorption spectra to create a sensor system that can detect the presence of ethanol in the human via tactile contact. As intoxication can result from small levels of ethanol, e.g., blood alcohol concentration (BAC) of 0.05% and above, the detection requirements should be capable of detecting such concentrations.

In one approach, interferometry at 2300 nm was used to sort light. In this approach, a movable mirror is used to create a two-beam interference pattern that creates a time modulated signal on a detection. In one embodiment of the present invention, an alternative interferometer was envisioned. In this alternative interferometer, the spatial heterodyne spectrometer (SHS), instead of a time varying interference pattern, an SHS would produce a spatially varying interference pattern that would be imaged onto an InGaAs array detector.

Figure 16:
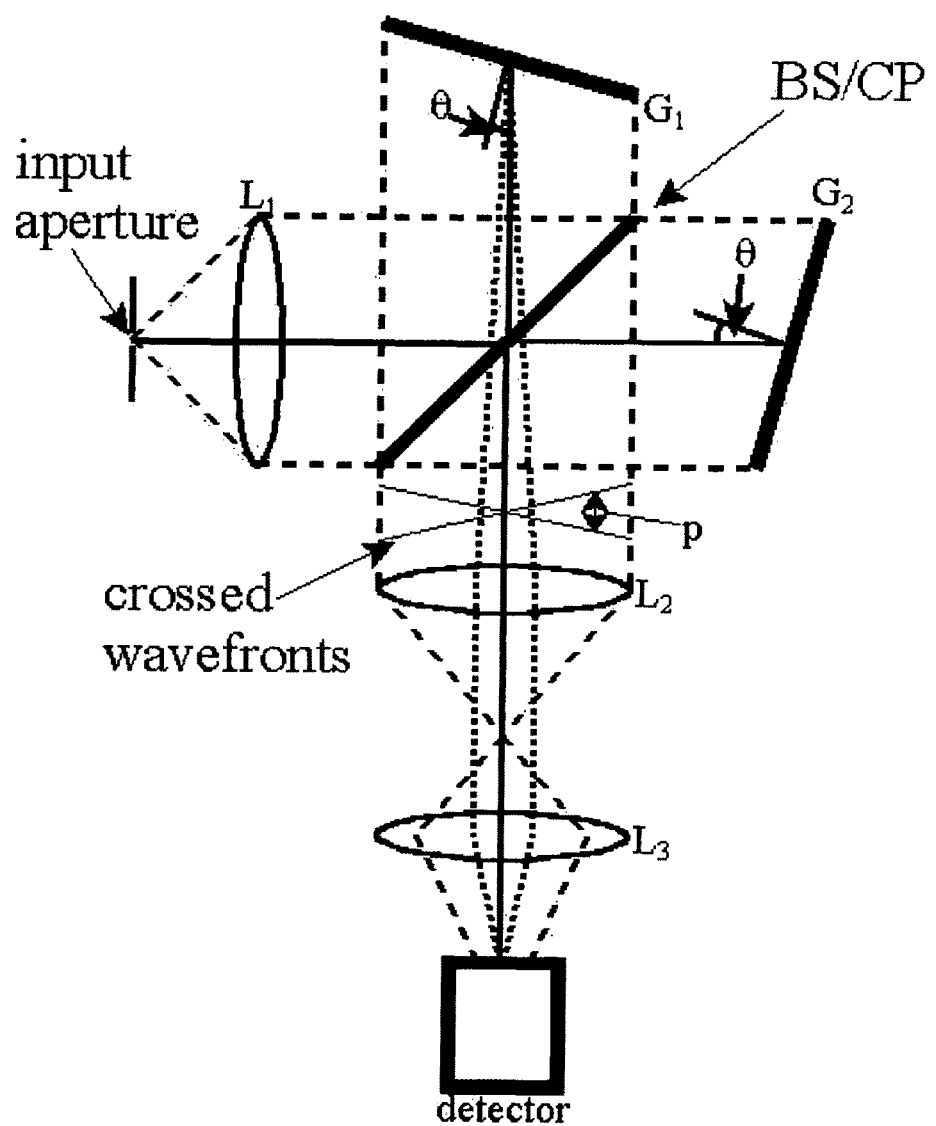
FIG. 16 shows a SHS schematic in which a fiber is used to couple the SHS to the "finger slot" via a fiber optic pursuant to aspects of an embodiment of the present invention.

In more detail, FIG. 16 shows a SHS schematic in which a fiber is used to couple the SHS to the "finger slot" via a fiber optic. The path length difference created by the beamsplitter (BS) and Grating 1 and Grating 2, G1 and G2 respectively created a linear fringe pattern on the detector. An FFT would be used to convert the signal into intensity versus wavelength.

Figure 17:
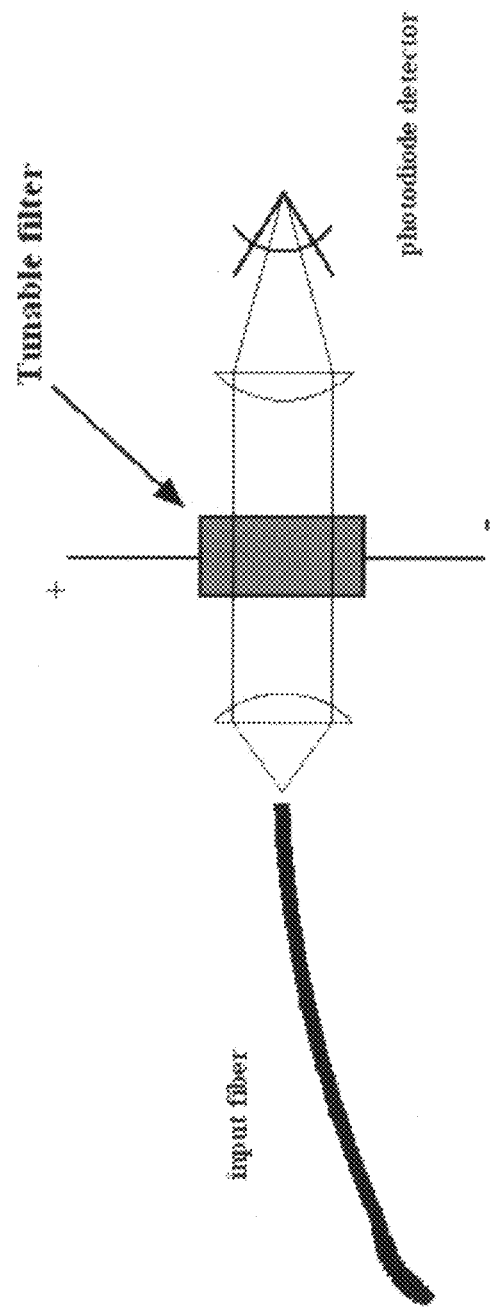
FIG. 17 shows the use of a filter, tunable or static, to sample light pursuant to aspects of an embodiment of the present invention.
Figure 18:
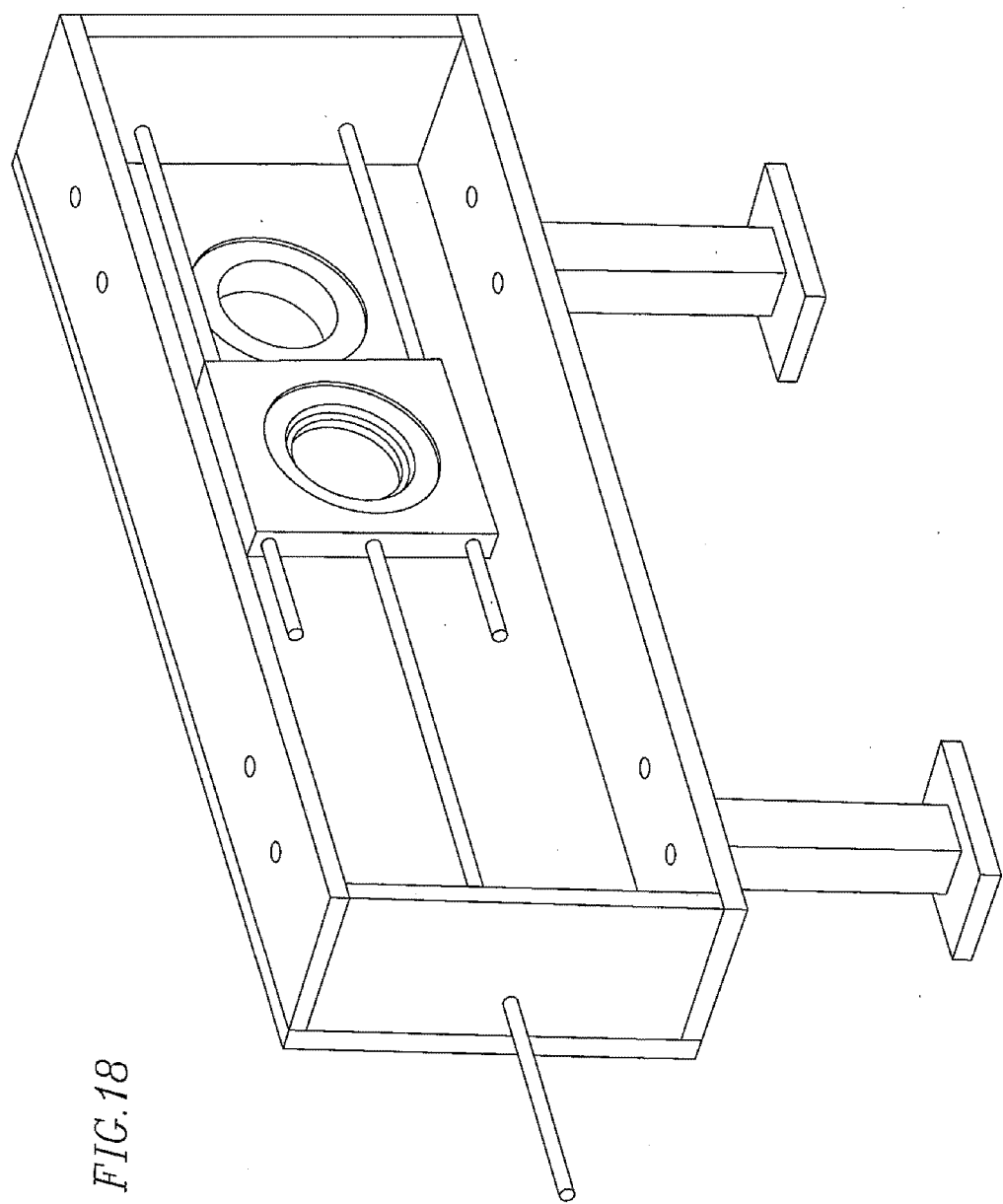
FIG. 18 shows a filter slider that can be used to change the filter in the light path sampling at different wavelengths pursuant to aspects of an embodiment of the present invention.

A common light sampling/sorting technique is to use optical filters designed to transmit a specific wavelength of light. A rotating wheel or slider can be used to change the filter in the light path sampling at different wavelengths. FIG. 18 shows a filter slider that can be used to change the filter in the light path sampling at different wavelengths. Alternatively, static filters can be used to replace the tunable filters. A static filter is a filter whose transmitted wavelength can be altered by changing an applied electrical voltage. In both cases the optical coupling is the same as shown in FIG. 17. That is, FIG. 17 shows the use of a filter, tunable or static, to sample light. The input fiber couples light from the finger to the filter. Post-filter the "sorted" light is focused on a photodiode detector.

Figure 19:
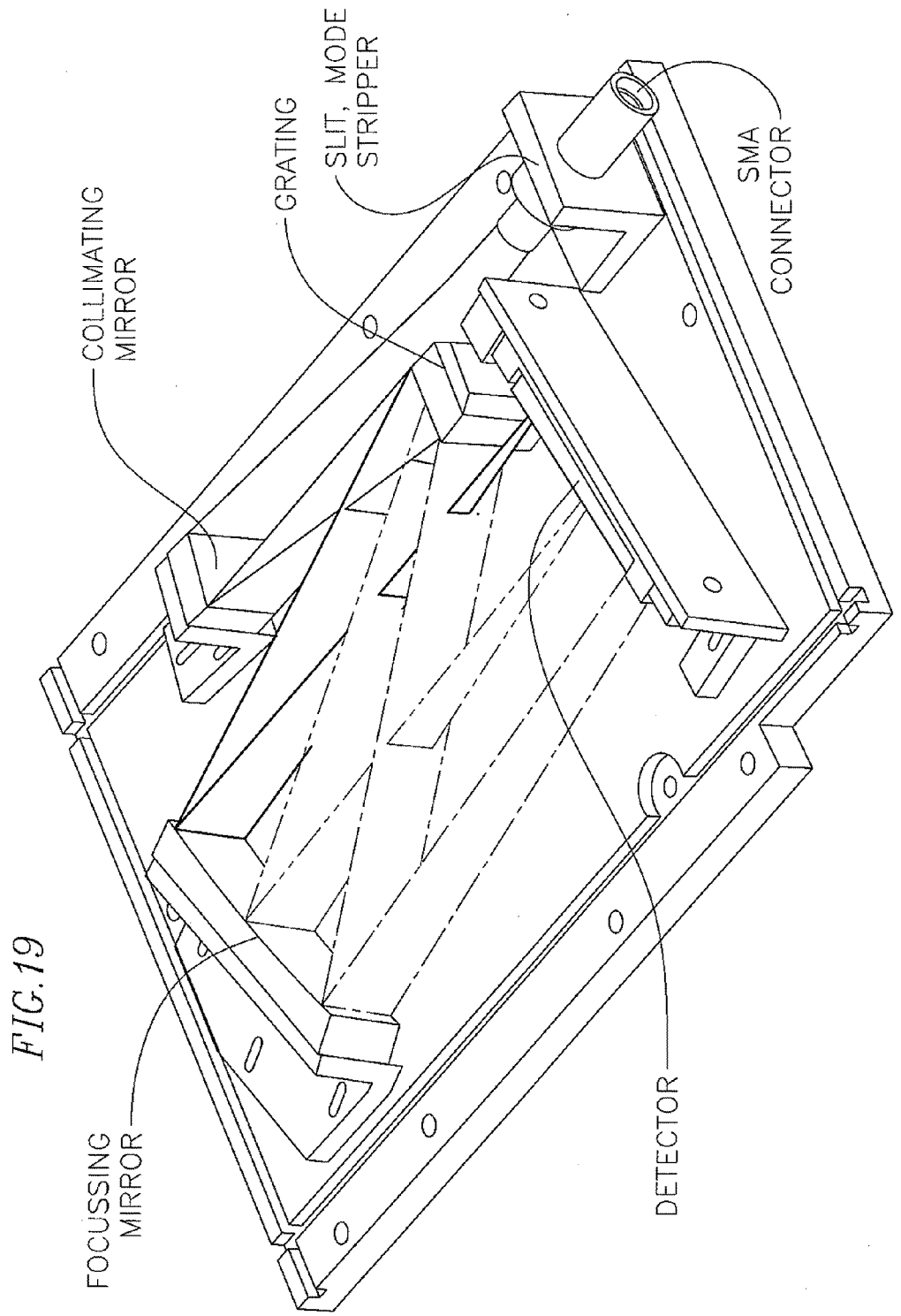
FIG. 19 shows a spectrometer pursuant to aspects of an embodiment of the present invention.
Figure 20:
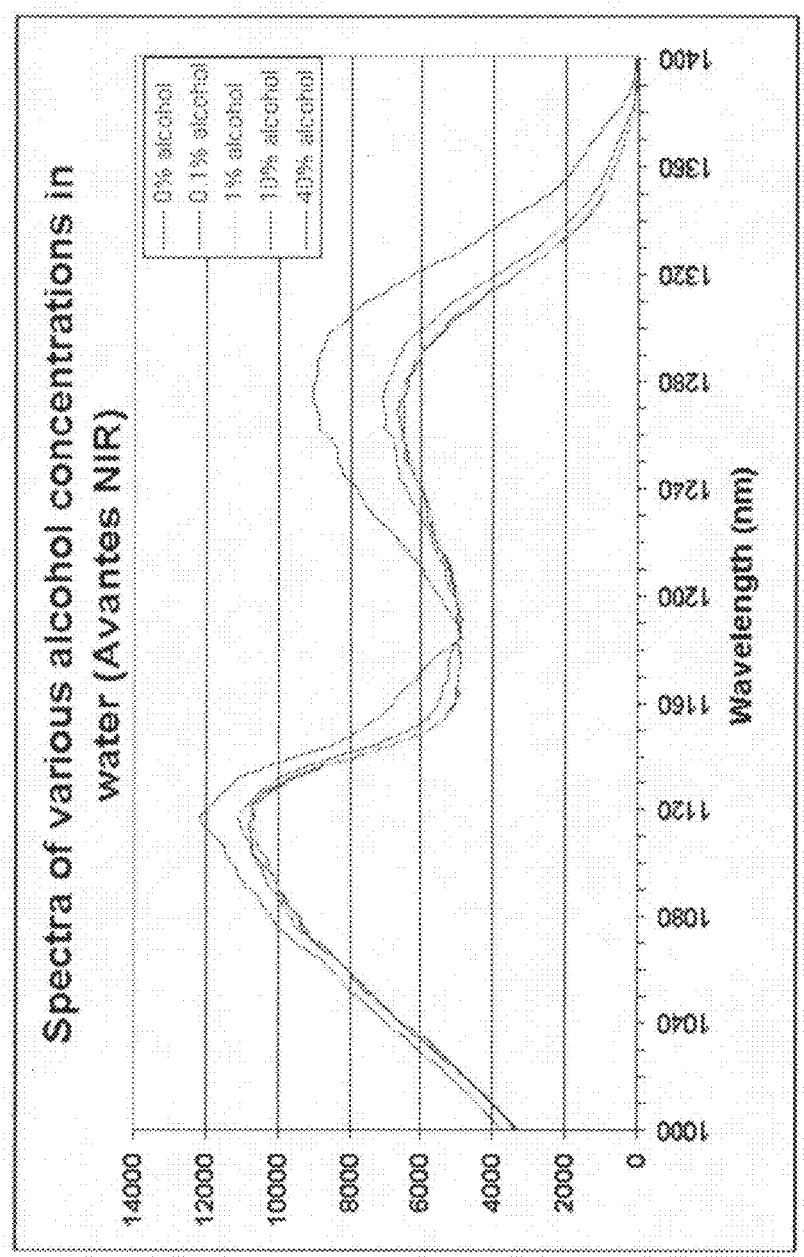
FIGS. 20 and 21 show portions of spectra from 1100 nm to 1700 nm pursuant to aspects of an embodiment of the present invention.
Figure 21:
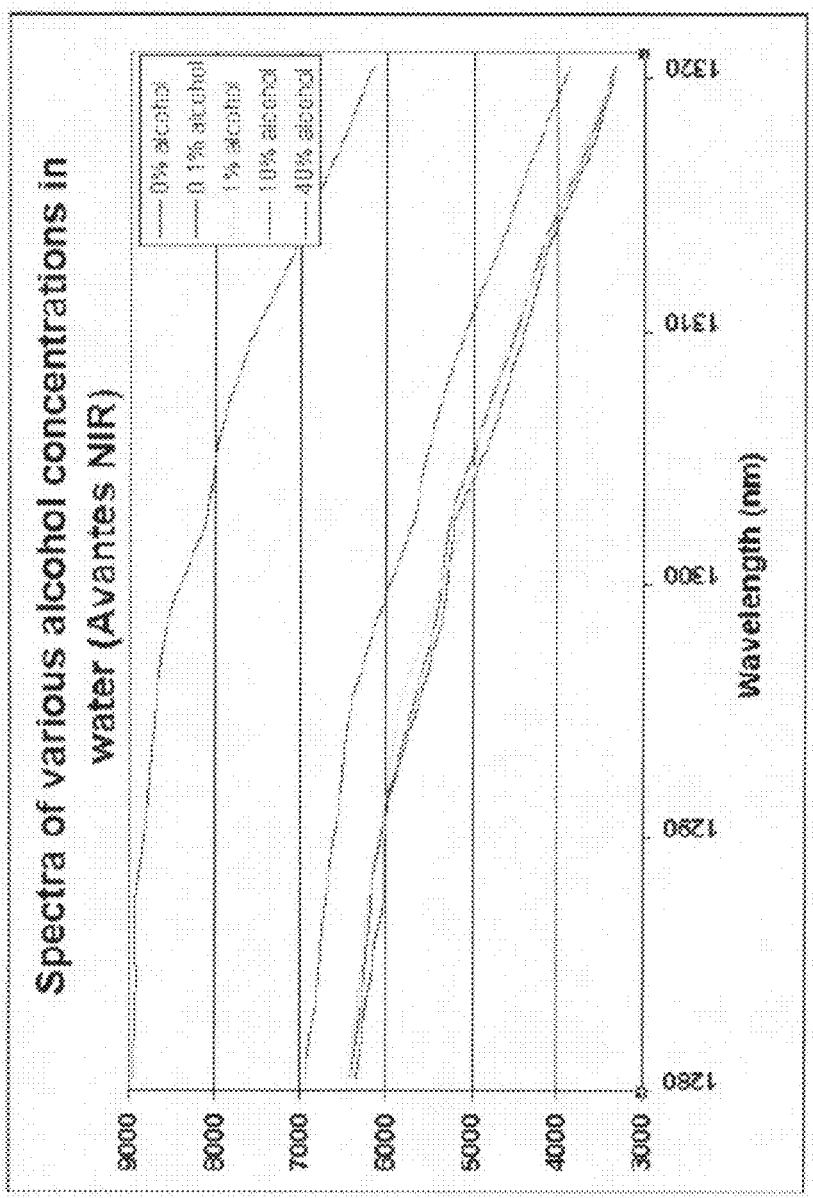

One embodiment of the present invention includes a diffraction grating spectrometer. Referring to FIG. 19, the spectrometer is shown to be a fiber optic spectrometer having a first mirror (Focussing mirror), a second mirror (Collimating mirror), a grating (Grating), a slit (Slit, mode stripper), a connector (SMA connector), and a detector (Detector) that are all coupled to an optical bench. Here, the detector is a linear InGaAs array detector having a linear array of InGaAs photodiodes. However, the present invention is not thereby limited, and any of various suitable spectrometers having a high single-to-noise ratio may be used. Here, a broadband fiber coupled light source was used to illuminate a cuvette that was filled with varying solutions of varying ethanol concentrations. Entire spectra from 1100 nm to 1700 nm were collected and a portion of which is shown in FIGS. 20 and 21. As shown by the spectrometer data in FIG. 21 having a wavelength range from 1280 nm to 1320 nm, the spectrometer of FIG. 19 is capable of distinguishing from 1% to 40%, but does not have enough resolution for distinguishing from 0 to 1%. That is, while ethanol detection was achieved it was not accurate enough to detect the from 0 to 0.1% level that might be found in the body of an intoxicated individual.

Figure 22:
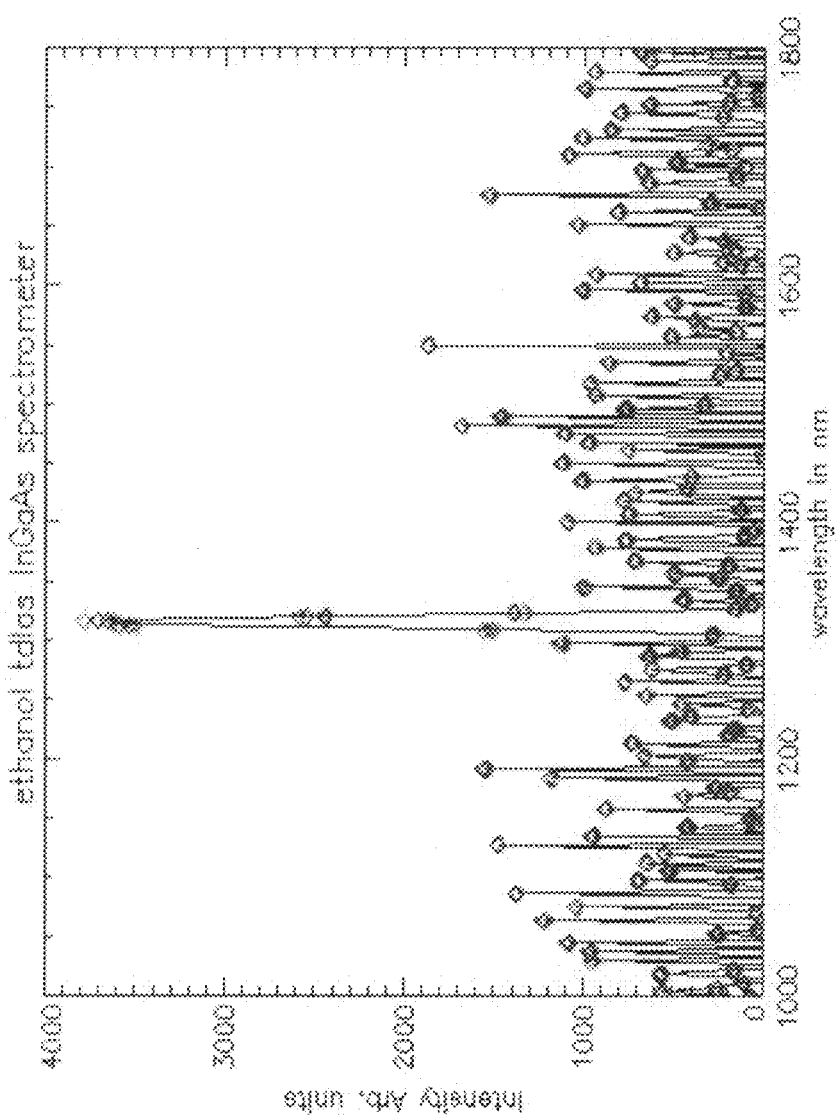
FIG. 22 shows a full spectrum, laser illumination pursuant to aspects of an embodiment of the present invention.
Figure 23:
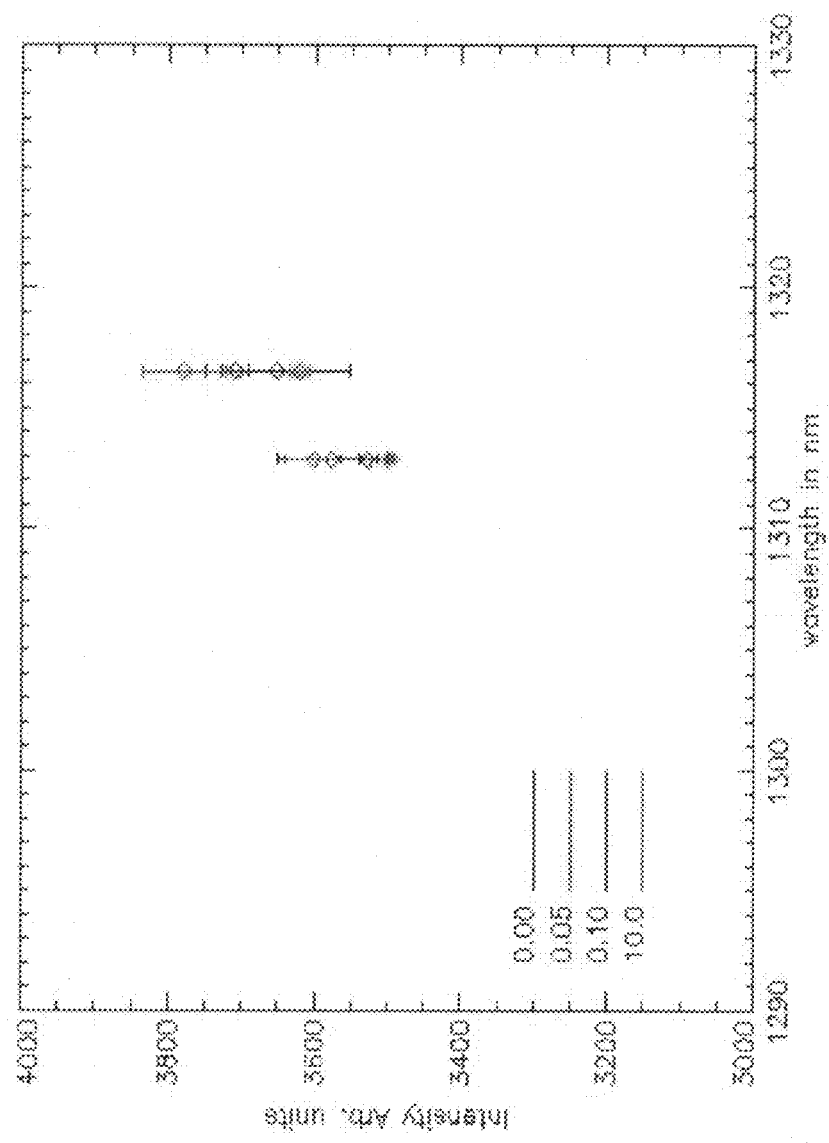
FIG. 23 shows NIR spectrometer data showing a statistically invalid but intriguing measurement of ethanol concentration versus observed intensity at about 1310 nm pursuant to aspects of an embodiment of the present invention.

To improve system sensitivity, a hybrid embodiment was envisioned. That is, in order to increase system sensitivity, a narrowband laser was selected as a replacement light source, using the data collected from the broadband source testing to identify appropriate wavelength regimes in which to operate. That is, as envisioned, an embodiment of the present invention includes a diode laser at about a 1310 nm band. Here, the diode laser at the 1310 nm band is used to illuminate the source and the NIR spectrometer would detect and isolate the ethanol signature. FIG. 22 shows a full spectrum, laser illumination of the embodiment. FIG. 23 shows NIR spectrometer data showing a statistically invalid but intriguing measurement of ethanol concentration versus observed intensity at about 1310 nm. That is, the NIR spectrometer observations of FIGS. 22 and 23 were not statistically significant. As such, a more accurate method was needed.

As such, while ethanol detection was achieved by the diffraction grating spectrometer of FIG. 19, it was not accurate enough to detect the 0-0.1% level that would be found in the body of an intoxicated individual. While not ultimately successful, these observations did indicate that the use of a narrowband source (or narrow band light source) can be utilized to detect ethanol.

In addition, it was realized that in the case of a narrowband source the spectrometer was a source of noise. As such, in another embodiment of the present invention, the spectrometer was replaced with a broadband detector or a single 3 mm diameter InGaAs photodiode detector (EO Systems). The 3 mm diameter InGaAs photodiode detector has a very low noise and is thermoelectric (TE) cooled. This created a very simple detection system involving a detector and a source, and no light sorting was needed.

Using a narrow band source abrogates the need for any post-sample light sorting technology, a spectrometer and/or a linear array of photodiode detectors. That is, the sample under consideration is illuminated with monochromatic and narrowband (typically a few nanometers wide) light from either a laser or monochromater. A single broadband detector (e.g., a single photodiode detector) is used to measure the amount of light that is transmitted through the sample; the amount of "absorber species" within the sample under test is calculated using:

$$I(\lambda) = I_o(\lambda) e^{-\alpha(\lambda)L}$$

where Io is the incident illumination of the sample, I is the observed transmitted intensity, $\alpha$ is the absorption co-efficient as a function of wavelength and L is the mass path length. Optical probing of the sample requires illumination either through the sample or of a uniform and standard volume, transmissive and/or reflective techniques can be used depending upon the sample involved.

Figure 24:
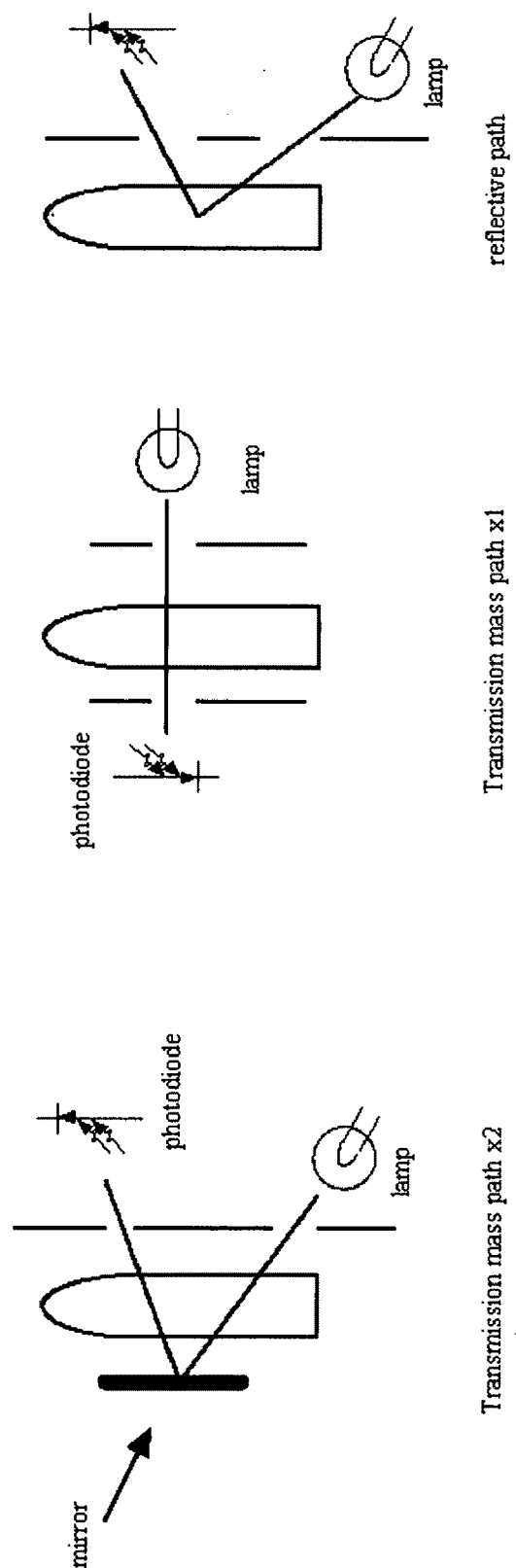
FIGS. 24A, 24B, and 24C show sample interrogation methods using a narrowband illuminate and photodiode detector pursuant to aspects of an embodiment of the present invention.

Also, FIGS. 24A, 24B, and 24C show sample interrogation methods using a narrowband illuminate and photodiode detector. FIGS. 24A, 24B, and 24C demonstrate transmission, reflection and variable path lengths through a tissue (e.g., a finger). Collimating and re-imaging optics would be used to render parallel light from the source and to image the collimated beam onto the photodiode after passage through the sample.

In more detail, FIG. 24A shows an incident light beam directed from a light source (lamp) to strike a mirror to double a mass path length of the portion of the incident light beam transmitted through the tissue. Due to effect of light scattering (e.g., with red blood cells), this mirror reflecting transmission approach in FIG. 24A may not be suitable for use with blood or finger sample(s), but this approach may still work with other relatively low light scattering samples (e.g., urine, saliva, water, etc.).

FIG. 24B shows an incident light beam directed from the light source (lamp) to a first side of the tissue, and a broadband detector (e.g., a single photodiode detector) configured to measure a portion of the incident light beam transmitted through the tissue from a second side of the tissue. In FIG. 24B, the second side is opposite to the first side. Again, due to effect of light scattering (e.g., with red blood cells), this direct transmission approach in FIG. 24B may not be suitable for use with blood or finger sample(s), but this approach may still work with other relatively low light scattering samples (e.g., urine, saliva, water, etc.).

FIG. 24C shows an incident light beam directed from a first side of the tissue toward a second side of the tissue, and a broadband detector (e.g., a single photodiode detector) configured to measure the portion of the incident light beam transmitted through a portion of the tissue and reflected back to the first side of the tissue. In FIG. 24C, e.g., due to the relatively large sampling surface area, this diffuse reflectance approach is likely to be suitable for use with blood or finger sample(s) even with light scattering (e.g., with red blood cells), and may also work well with other relatively low light scattering samples (e.g., urine, saliva, water, etc.).

Figure 25:
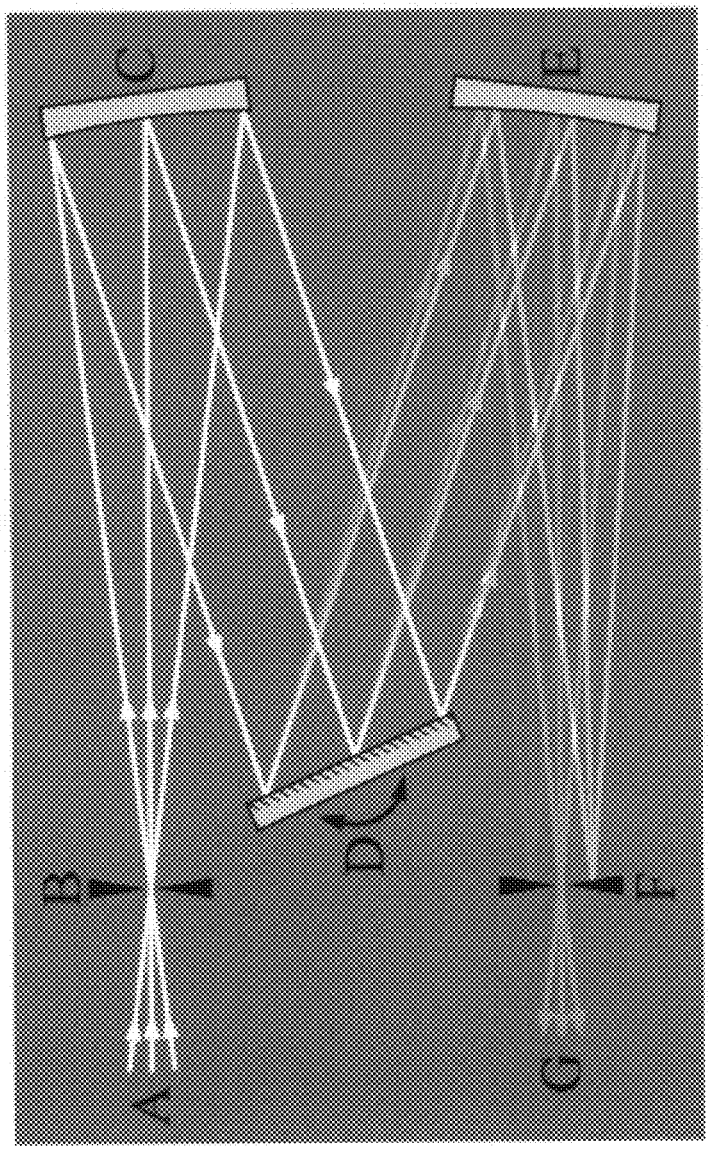
FIG. 25 shows detailed operating principles of a monochrometer pursuant to aspects of an embodiment of the present invention.

Also, in one embodiment, absorption spectroscopy with a narrowband source is performed with a monochrometer, which is essentially a grating spectrometer with an input and exit slit. FIG. 25 shows detailed operating principles of a monochrometer. That is, in FIG. 25, light (A) is focused onto an entrance slit (B) and is collimated by a curved mirror (C). The collimated beam is diffracted from a rotating grating (D) and the dispersed beam re-focused by a second mirror (E) at the exit slit (F). Each wavelength of light is focused to a different position at the slit, and the wavelength which is transmitted through the slit (G) depends on the rotation angle of the grating. While the scanning monochrometer of FIG. 25 would work for the ethanol detection problem, its bulk and mechanical motion make it impractical as a source for vehicular based ethanol detection.

As such, an embodiment of the present invention provides an enhanced system and method for ethanol detection. Here, the ethanol sensor uses a diode laser for illumination and a InGaAs photodiode as a receiver. This system is entirely or substantially passive yet retains spectral agility as the laser is tunable by changing the system temperature. Initially the spectral region around 1310 nm was selected as it has a large difference in absorption between ethanol and water as well as being accessible to lasers developed for the telecommunication industry. The diode laser can be composed of a diode selected from the group consisting of a double heterostructure laser diode, a quantum well laser diode, a distributed feedback laser diode, a vertical cavity surface emitting laser (VCSEL) diode, and a vertical external-cavity surface-emitting laser (VECSEL) diode.

Figure 26:
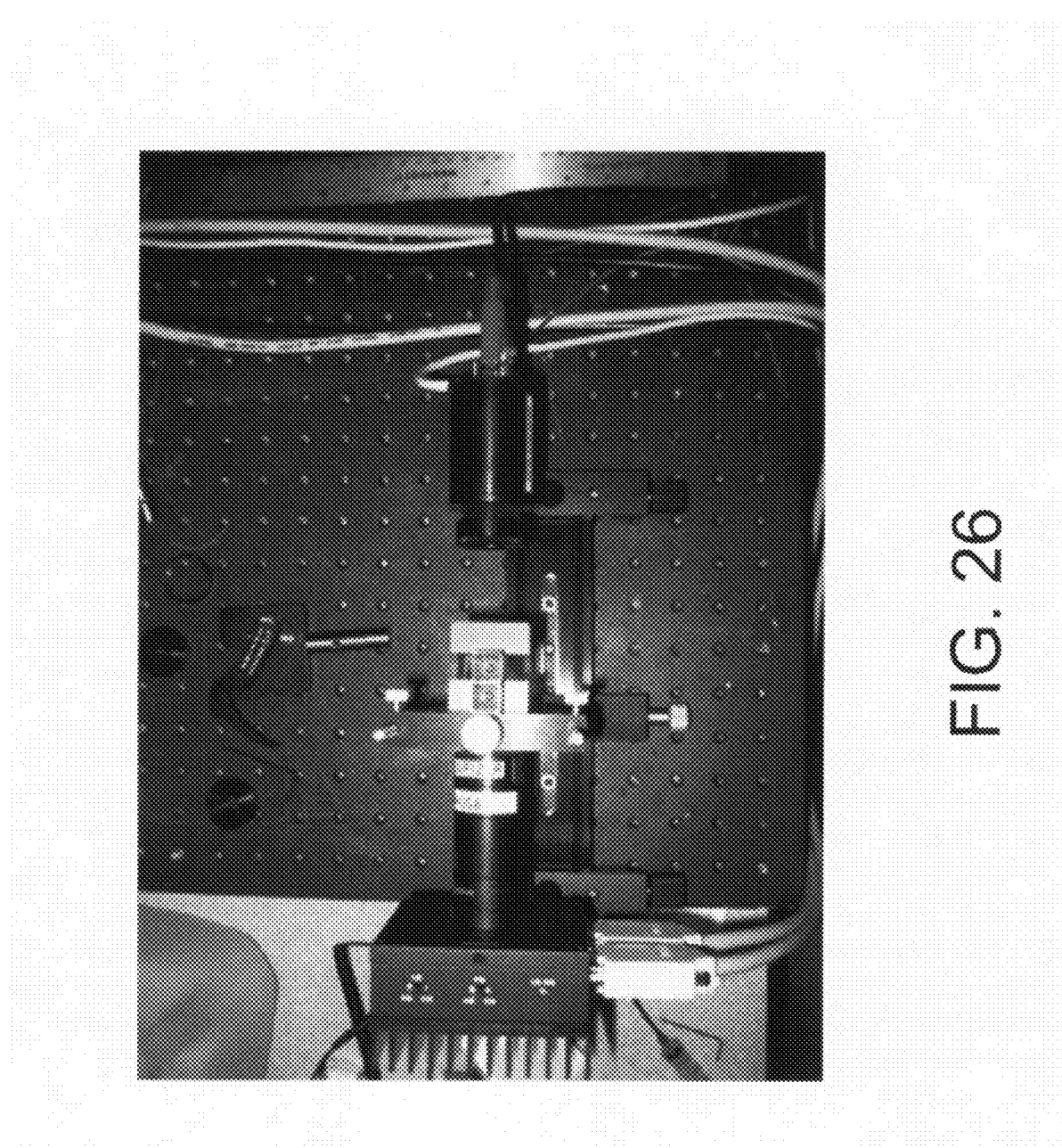
FIG. 26 shows an ethanol sensor apparatus pursuant to aspects of an embodiment of the present invention.

Referring to FIG. 26, an ethanol sensor apparatus according to an embodiment of the present invention includes a diode laser mounted with integral thermoelectric cooler (TEC) and thermistor monitor connected to a PID temperature controller and a laser diode driver system. In addition, the sensor may include some collimating and beam expanding optics between the diode laser and a cuvette adapted to increase a mass path. Here, the cuvette is placed between the diode laser and a broadband detector (e.g., a single InGaAs photodiode detector). That is, as a comparison, in the hybrid approach described above, the broadband detector is replaced with a fiber optic coupling cable that is attached to the entrance port of a NIR spectrometer.

In more detail, the ethanol sensor according to one embodiment of the present invention includes a laser diode mount with an integral thermistor and TE cooler. A laser diode driver was used to operate a laser diode in constant power output mode. The laser diode is an AlGaAs laser in a 18 5.6 mm package, which provides a stable single mode transverse mode oscillation at a nominal wavelength of 1310 nm and a CW light output of 10 mW. A spectrometer was used to tune the laser diode in temperature until an output wavelength of 1310 nm was achieved. Temperature of the laser diode to maintain 1310 nm output was controlled to an accuracy of 0.002 degree C. using a TE temperature controller.

A 25.4 mm diameter F/1 Plano-convex lens approximately one focal length from the laser diode emission surface is used to create a beam of collimate light that is then diffused by two 25.4 mm diameter pieces of opal glass. This creates a source of nearly lambertian illumination about 10 mm in diameter. A neutral density filter can be used to lower the intensity of the illumination as required. Two 10 mm cuvette holders, which have been epoxied together, are used to hold the water/ethanol mixture with a 20 mm sample path length. Both cuvettes are clamped into a cuvette holder.

After passing through the sample in the cuvette the collimated/diffused light is incident on the active surface of a 3 mm InGaAs photodiode detector. An integral TE cooling and a dual gain FET transimpedance amplifier is used to measure the optical intensity post sample. When operated at −30° C. this detector has a NEP of $<2.0 \times 10^{-14}$ $W/(Hz)^{1/2}$ with a responsivety of 0.9 A/W at 1310 nm. A 16-bit national instrument DAQ card is used to monitor the output of the detector and digitize the resulting data for further analysis.

The following bench tests illustrate the present invention in more detail. However, the present invention is not limited by these bench tests.

While the components and configuration of the successor bench test systems changed over time and when used at different wavelengths, it generally includes a laser module (whose wavelength could be altered by the replacement of the internal diode and subsequently fine-tuned via temperature control), collimating optics, diffusing optics, focusing optics, neutral density filter(s), apertures, a section to firmly hold samples in place, and a broadband or high performance photodiode detector operated with a thermoelectric cooler for stabilizing, a dual gain FET input transimpedence amplifier, and a bipolar power supply.

Of note during the bench test system testing was the need to completely isolate the sample(s) from the possibility of movement or change in absolute position as well as the need to expand the light beam size well beyond that of the clear aperture of the photodiode (overfill) so that any vibration in the system would not impart a change in measured intensity. Also, it became evident during testing that, in order to remain stable (not oscillate) the laser needed to be operated at a "sweetspot" which was generally towards the middle of its power range; further the laser had to be operated in constant power mode as opposed to constant current.

Potential cross-contamination of samples was avoided by using dedicated syringes and beakers for each concentration. Potential variations caused by temperature gradients within an individual sample were avoided by reusing the same aliquot of each concentration as opposed to using a subset of a greater size of the same sample concentration.

Figure 27:
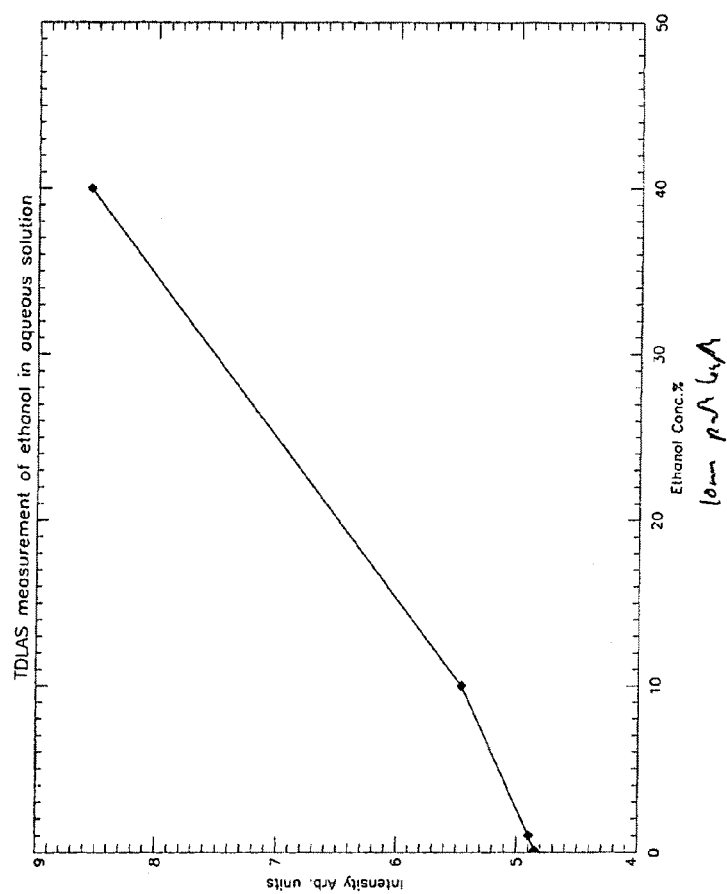
FIG. 27 shows a transmission intensity at about 1310 nm for samples pursuant to aspects of an embodiment of the present invention.
Figure 28:
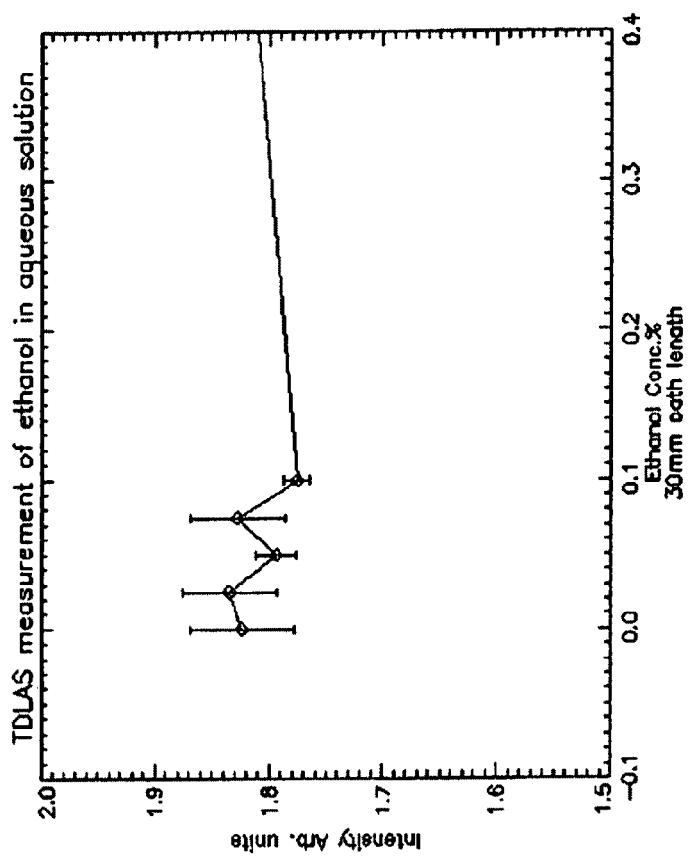
FIGS. 28 and 29 show results for a 0-0.1% region that did not correspond to Beer's law pursuant to aspects of an embodiment of the present invention.

Initial ethanol aliquots were prepared with concentrations varying from 0.1% vol to 40% vol. FIG. 27 shows the transmission intensity at a 1310 nm band for each sample. The initial results show a surprising correlation with Beer's law; however, FIG. 28 shows the results for the 0-0.1% region (or regime) did not correspond to Beer's law, and in fact were too noisy to use. That is, FIG. 27 shows the ethanol measurements 0-40% at 1310 nm. The calculated error bars were too small for the plot. However, FIG. 28 shows low concentration ethanol measurements with 1 sigma error bars. These results are not statistically valid.

Figure 29:
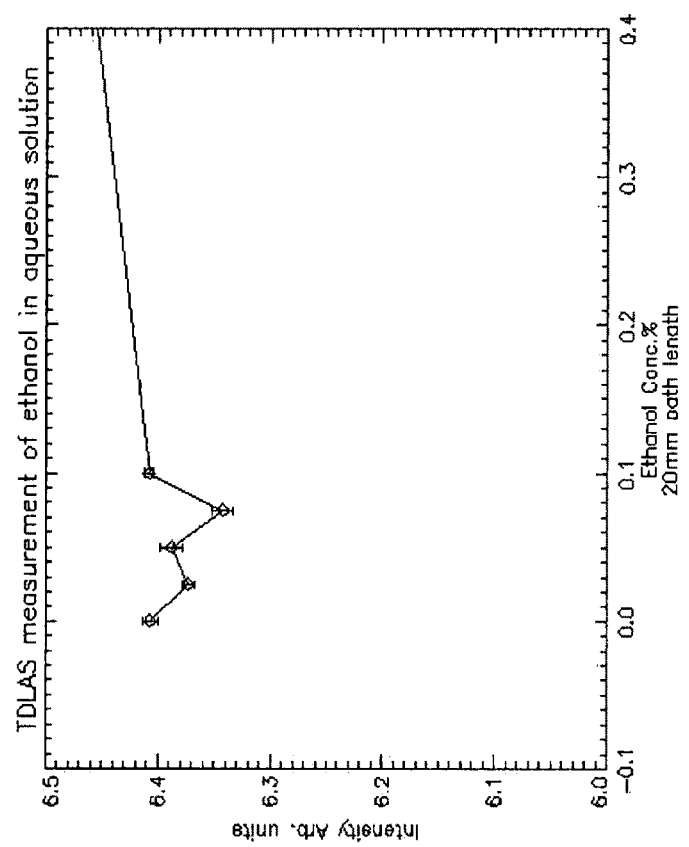

After re-engineering the sample holder and altering the collimating optics to create a system less susceptible to vibration, new data were collected as shown in FIG. 29. FIG. 29 shows statistically significant ethanol measurements at the 1310 nm band. The odd behavior (non-Beer's) at 0.05% may not be an artifact and instead may be a real non-linear phenomenon.

The data in FIG. 29 shows the apparent non-linear, response of ethanol to the 1310 nm laser light. This dramatic effect may be used to identify alcohol content below 0.1%. An additional refinement should be used to clearly discriminate 0% ethanol from high concentrations of ethanol (0.1%); absorption measurements at a second wavelength will be used for further systemic refinements.

While the potential efficacy of this spectroscopic technique was demonstrated at the 1310 nm band, a simultaneous measurement of the same sample at a second wavelength should be made for accurate determination due to the non-linear nature of the response at the 1310 nm band.

In summary, it has been demonstrated that the highly non-linear absorption of ethanol in the NIR region of the spectrum, specifically 1310 nm, may be used to identify quantities of ethanol consistent with BAC of 0.05% or higher. The one caveat is that to enhance quantitative determination of ethanol at 0% and 0.1%, a second wavelength should be used; further ethanol absorption in this second wavelength region (or regime) should have slightly different optical absorption than at the 1310 nm region (or regime) used previously. The efficacy of using diode lasers as a narrowband source to detect ethanol without any light dispersing technology was also demonstrated. It should be possible to construct an "ethanol sensor" utilizing two or more diode lasers and a single cooled and amplified InGaAs photodiode to detect small quantities of ethanol in solution and in-vivo.

Figure 30:
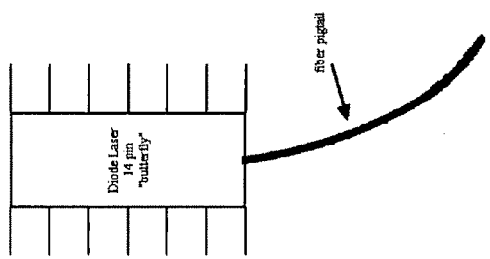
FIG. 30 shows a schematic of a butterfly packaged diode laser with integral fiber optic pigtail pursuant to aspects of an embodiment of the present invention.

In view of the forgoing and as envisioned in one embodiment of the present invention, a substance sensor device includes two lasers, one at a 1310 nm band and another at another wavelength band that are coupled together via a fiber mixer. As shown in FIG. 30, each laser is packaged in a 14 pin "butterfly" package with an integral fiber optic pigtail. The laser unit is composed of the laser diode, an integral photodiode to monitor laser output, a thermistor and TEC to stabilize laser temperature. A fiber collimating optic at the "finger slide" is also included to collimate the light incident on the finger, and then post-finger optics are used to re-image the collimated beam onto an integral InGaAs photodiode/pre-amp system with integral temperature control. A 12-bit DAC is provided to digitize the analog photo-diode output into a digital "word" accessible by any number of microcontrollers/microprocessors.

Figure 31:
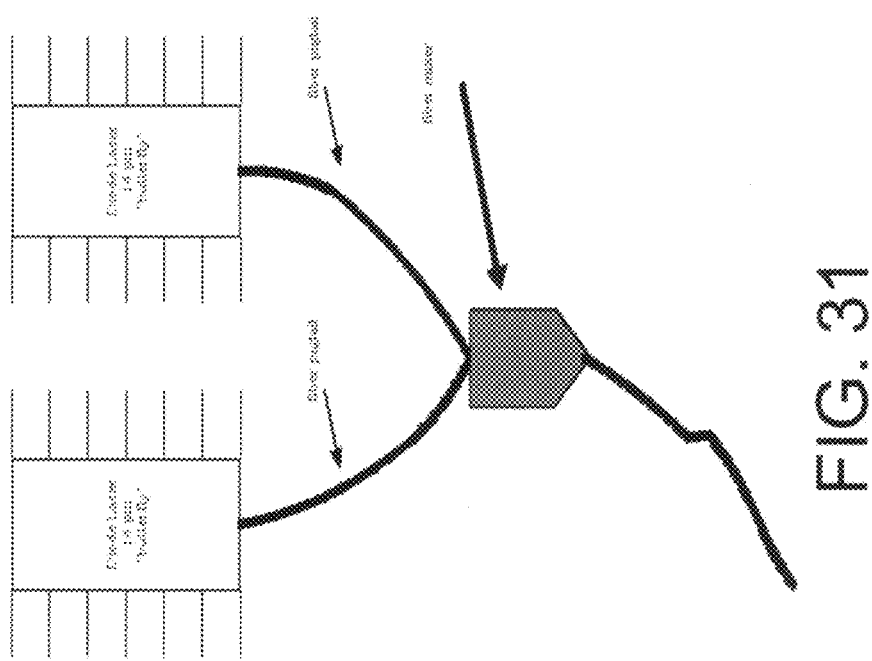
FIG. 31 shows two diode lasers with pigtails, each at a distinct wavelength pursuant to aspects of an embodiment of the present invention.

In more detail, FIG. 30 shows a schematic of a butterfly packaged diode laser with integral fiber optic pigtail, and FIG. 31 shows two diode lasers with pigtails, each at a distinct wavelength. In FIG. 31, the lasers are mixed into a single fiber via a fiber mixer.

As envisioned, an entire substance sensor system according to an embodiment of the present invention is monitored and controlled by a microcontroller. In one embodiment, this system is designed to be a GO/NO-GO device and not a precision measure of BAC. As such, the system may further include a statistical model to ensure device efficacy.

Also, in view of the forgoing and as envisioned, suitable embodiments of the present invention provide a system designed to prevent an intoxicated individual from operating a vehicle or other device, whether it is a car, boat, plane, bus, heavy equipment, or entry point. In addition, suitable embodiments of the present invention provide a system to reduce theft prevention. Through the use of biometric fingerprint scanning technology, the system is designed as a theft-deterrent which prevents unauthenticated individuals from operating a motor driven vehicle. One representative embodiment provides a system that is adapted to verify that the person being tested by the system for intoxication is actually the driver of the vehicle.

In addition, suitable embodiments of the present invention can be applied to a rental car fleet to reduce the risk of a driver receiving a DUI, wrecking their vehicle in an alcohol related incident, and/or theft.

Other embodiments of the present invention can be applied to an aircraft (e.g., to reduce the risk of hijackings and/or other suitable aviation risks); to a mass transit vehicle (e.g., bus, locomotive, trolley bus, taxicab, etc. to ensure that a vehicle's operator is sober and/or authorized operator of that vehicle); to a watercraft (e.g., boat, cargo, passenger, tankers, ocean going ships, etc.), and/or to a industrial equipment (e.g., heavy construction equipment, such as dump trucks, cranes, tractors, forklifts, etc., industrial machinery such as conveyor systems, large machinery, presses and any other suitable piece of large industrial equipment where human/operator error could result in loss of life or damage to property).

Moreover, certain embodiments of the present invention can be used to increase and/or ensure building security (e.g., incorporated with a time clock). These embodiments utilize authentication (e.g., fingerprint authentication) to allow an individual to gain entry to a building or room within a building, and/or are adapted to include detection of illegal or controlled substances to prevent security breaches, industrial accidents and other incidents where intoxication of a worker could lead to an accident.

Figure 32:
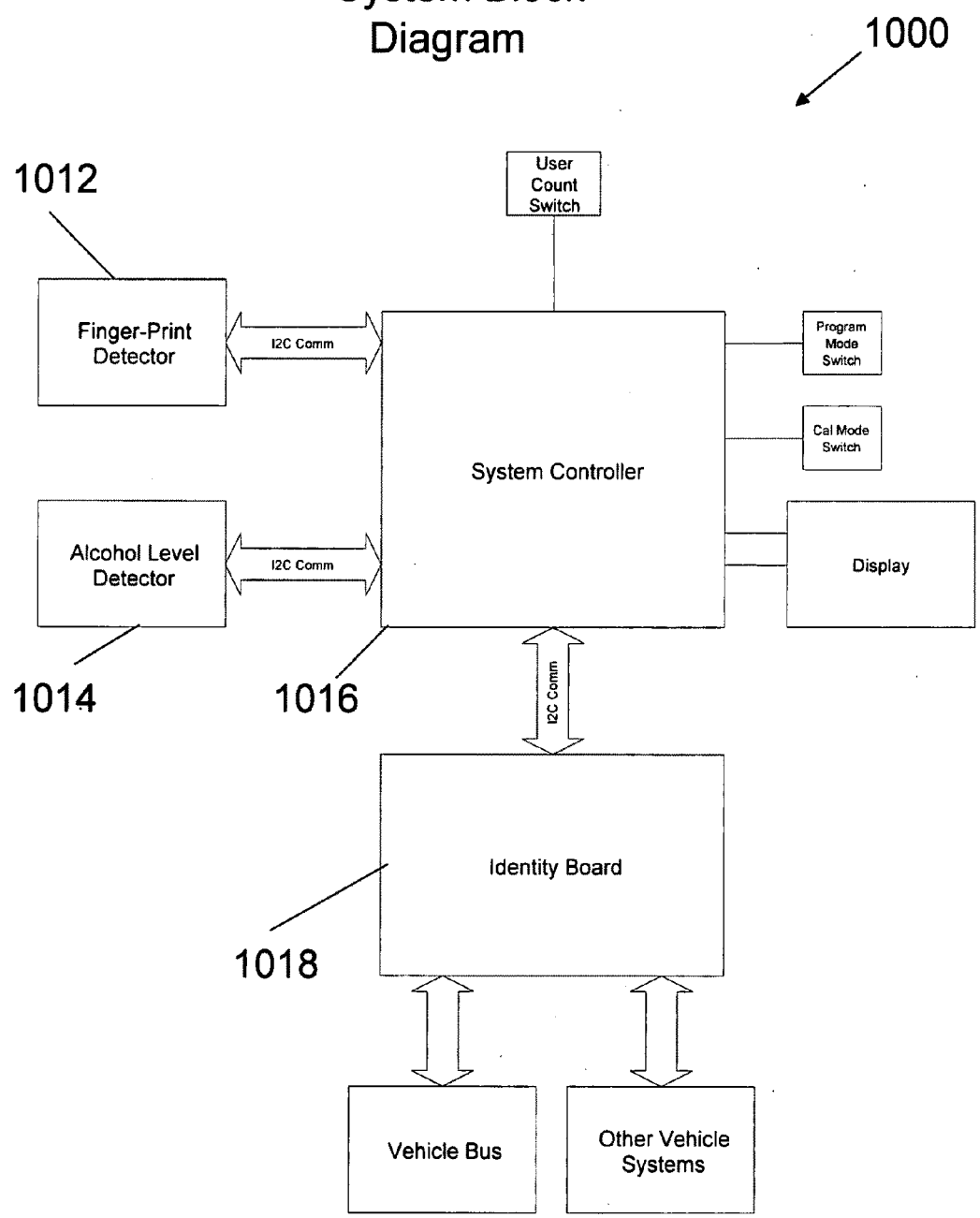
FIG. 32 shows a block diagram of a system for controlling a vehicle given to a third party, for in-vivo measurement of a concentration of a substance in a tissue of a person, and/or for preventing use of a vehicle by an operator of the vehicle pursuant to aspects of an embodiment of the present invention.

In more detail, FIG. 32 shows a block diagram of a system for controlling a vehicle given to a third party, for in-vivo measurement of a concentration of a substance in a tissue of a person, and/or for preventing use of a vehicle by an operator of the vehicle according to certain embodiments of the present invention. As shown in FIG. 32, the system 1000 includes a control module (or system controller) 1016, a biometric authenticator (or fingerprint detector) 1012, a substance detecting sensor (or detecting device or alcohol level detector) 1014, and/or an identity board 1018. The biometric authenticator 1012 is coupled to the control module 1016 via a bus (e.g., via I2C Comm), and the identity board 1018 is also coupled to the control module 1016 via a bus (e.g., I2C Comm). The substance detecting sensor 1014 can be a substance detecting sensor adapted to provide a substance level in a user (e.g., the third part, the person, the operator, etc.) to the control module 1016 via a bus (e.g., via I2C Comm). Here, the control module 1016 is adapted to communicate a driving restriction to the vehicle if the substance level in the operator is above a tolerance level or if the operator is not authenticated by the authenticator 1012.

Also, in one embodiment of the present invention, the substance level is determined at an extremity of the operator, the operator is also authenticated at the extremity, and the extremity is selected from the group composed of finger, thumb, toe, ear, palm, sole, foot, hand, and/or head.

In one embodiment, the control module 1016 is further adapted to communicate with the vehicle to permit the vehicle to start if the operator has been authenticated by the authenticator 1012 and the substance level in the operator is not above the tolerance level.

In one embodiment, the substance detecting sensor 1014 is adapted to detect an alcohol level in the operator. Here, the substance detecting sensor 1014 may include a broadband detector (e.g., a single photodiode detector). In addition, the substance detecting sensor may include a diode laser configured to direct a light beam at a specific wavelength toward the broadband detector.

In addition, FIG. 32 shows that the control module 1016 is coupled to a user count switch, a program mode switch, a calibration mode switch and a display, and the identity board 1018 is coupled to a vehicle bus and other vehicle system.

Figure 33:
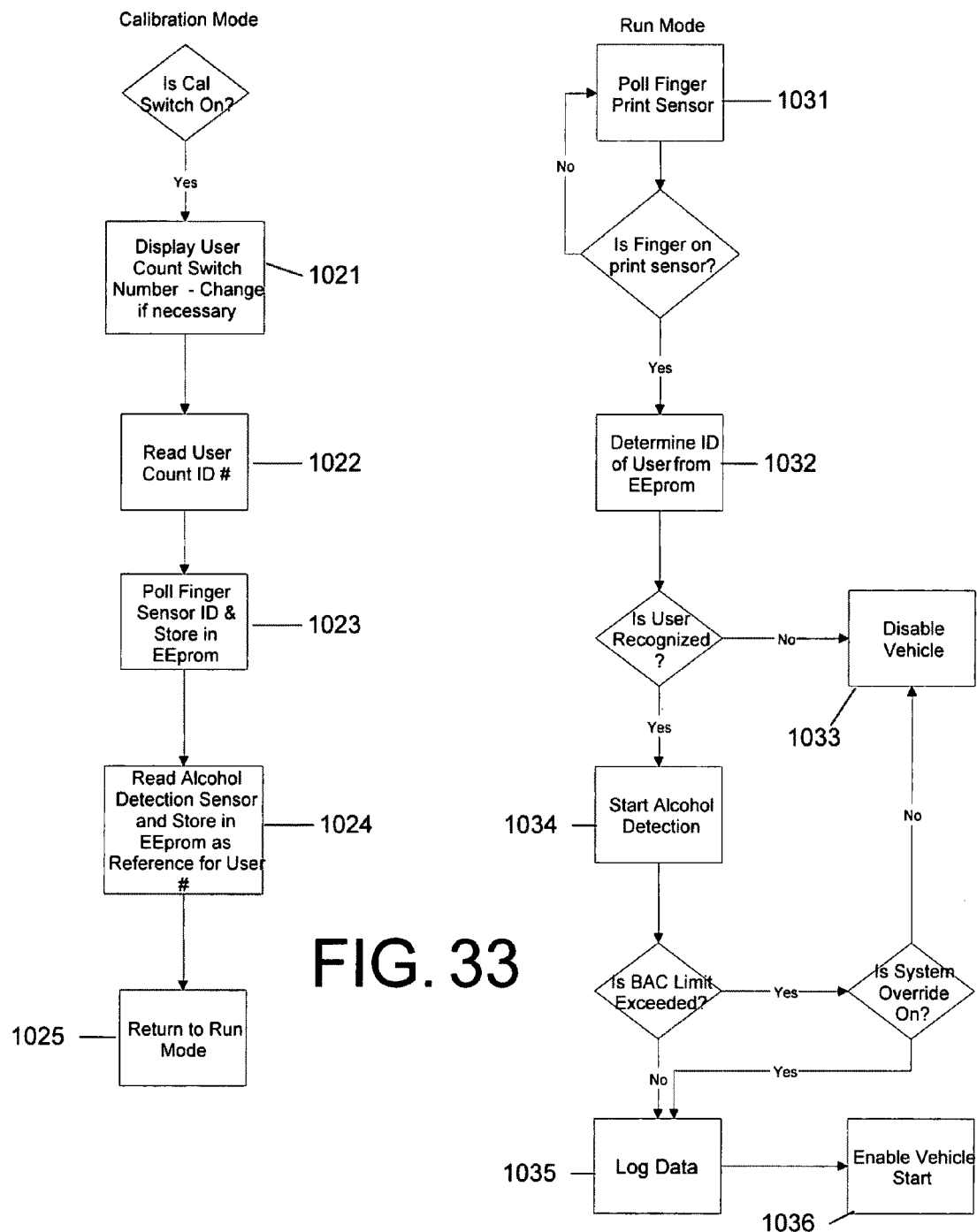
FIG. 33 shows a flowchart of process blocks of system logics for controlling a vehicle given to a third party, for in-vivo measurement of a concentration of a substance in a tissue of a person, and/or for preventing use of a vehicle by an operator of the vehicle pursuant to aspects of an embodiment of the present invention.

FIG. 33 shows a flowchart of process blocks of system logics for controlling a vehicle given to a third party, for in-vivo measurement of a concentration of a substance in a tissue of a person, and/or for preventing use of a vehicle by an operator of the vehicle according to certain embodiments of the present invention. As shown in FIG. 33, the system logics can be operating either in a calibration mode or a run mode. In the calibration mode, the system logics determine if a calibration switch is turned on. If the calibration switch is turned on, the system logics display user count switch number (that may change) in block 1021. In block 1022, the system logics read user count identification number. In block 1023, the system logics poll the finger sensor identification and store in a persistent memory (e.g., an EEprom). In block 1024, the system logics read alcohol detection sensor and store the reading in the persistent memory as reference for a user (e.g., the third party, the person, the operator, etc.), and return to the run mode in blocks 1025.

In the run mode, the system logics poll the fingerprint sensor in block 1031. Here, if the finger of the user is not on the fingerprint sensor, the system logics return back to block 1031. If the finger of the user is on the fingerprint sensor, the system logics determine identification of the user from the persistent memory in block 1032.

The system logics then determine if the user is recognized. If the user is not recognized, the system logics disable the vehicle in block 1033. If the user is recognized, the logics start alcohol detection in block 1034.

If the BAC limit is exceeded, the system logics then determined if the system override is on. If the system override is not on, the system logics move to block 1033 to disable the vehicle. By contrast, if the system override is on or the BAC limit has not been exceeded, the system logics log this data in block 1035, and enable the vehicle to start in block 1036.

Figure 34:
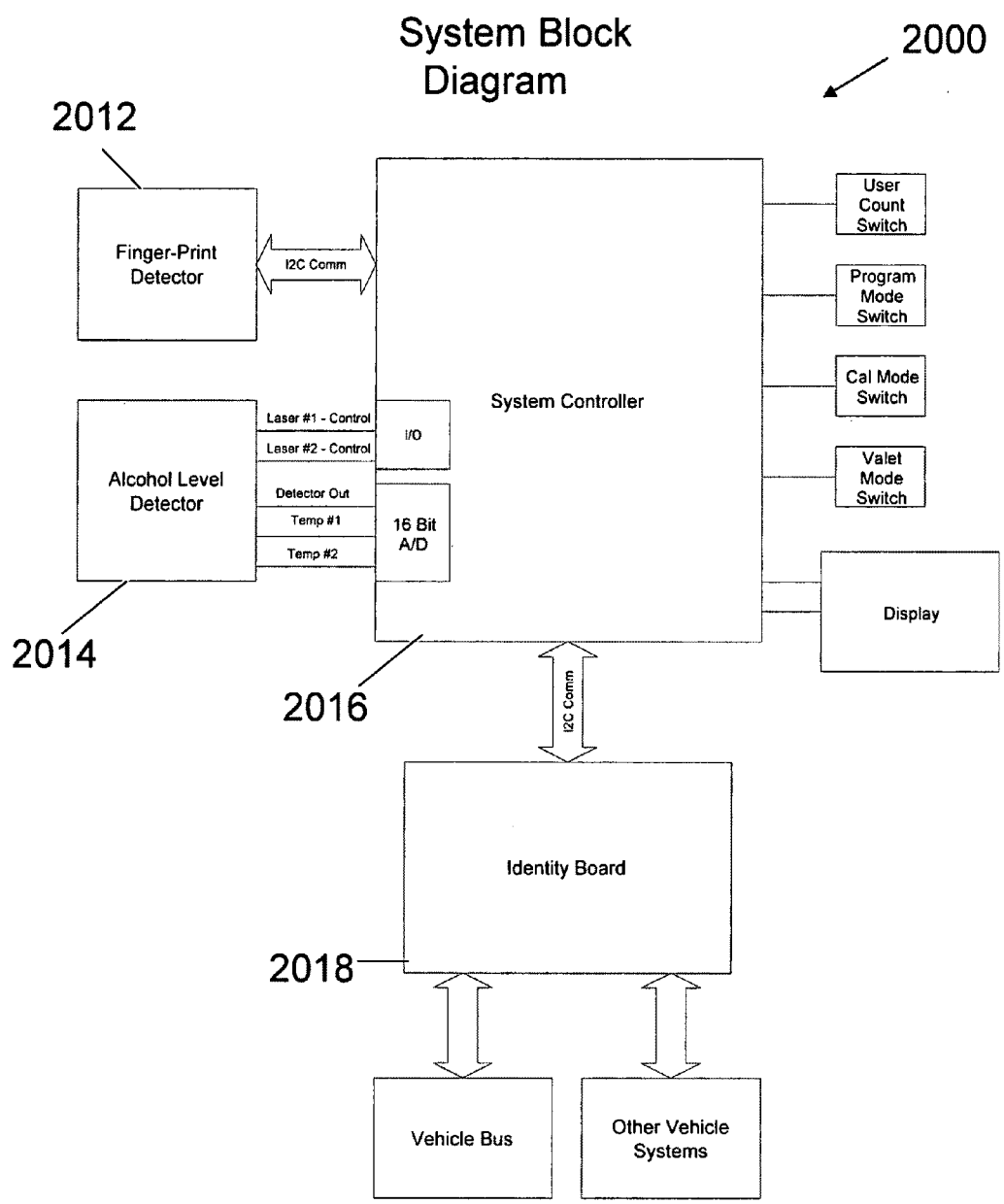
FIG. 34 shows a block diagram of another system for controlling a vehicle given to a third party, for in-vivo measurement of a concentration of a substance in a tissue of a person, and/or for preventing use of a vehicle by an operator of the vehicle pursuant to aspects of an embodiment of the present invention.

FIG. 34 shows a block diagram of another system for controlling a vehicle given to a third party, for in-vivo measurement of a concentration of a substance in a tissue of a person, and/or for preventing use of a vehicle by an operator of the vehicle according to certain embodiments of the present invention. As shown in FIG. 34, the system 2000 includes a control module (or system controller) 2016, a biometric authenticator (or fingerprint detector) 2012, a substance detecting sensor (or detecting device or alcohol level detector) 2014, and/or an identity board 2018. The biometric authenticator 2012 is coupled to the control module 2016 via a bus (e.g., via I2C Comm), and the identity board 2018 is also coupled to the control module 2016 via a bus (e.g., I2C Comm). The substance detecting sensor 2014 can be a substance detecting sensor adapted to provide a substance level in a user (e.g., the third party, the person, the operator, etc.) to the control module 2016 via a bus having a first laser control communication line (Laser#1—Control), a second laser control communication line (Laser#2—Control), a detector communication line (Detector Out), a first temperature communication line (Temp #1), and a second temperature communication line (Temp #2). Here, the control module 2016 is adapted to communicate a driving restriction to the vehicle if the substance level in the operator is above a tolerance level or if the operator is not authenticated by the authenticator 2012.

Also, in one embodiment of the present invention, the substance level is determined at an extremity of the operator, the operator is also authenticated at the extremity, and the extremity is selected from the group composed of finger, thumb, toe, ear, palm, sole, foot, hand, and/or head.

In one embodiment, the control module 2016 is further adapted to communicate with the vehicle to permit the vehicle to start if the operator has been authenticated by the authenticator 2012 and the substance level in the operator is not above the tolerance level.

In one embodiment, the substance detecting sensor 2014 is adapted to detect an alcohol level in the operator. Here, the substance detecting sensor 2014 may include a broadband detector (e.g., a single photodiode detector) as described above. In addition, the substance detecting sensor may include a first diode laser configured to direct a light beam at a first specific wavelength toward the broadband detector and a second diode laser configured to direct a light beam at a second specific wavelength toward the broadband detector. Here, the broadband detector may be coupled to a 16 bit analog/digital (A/D) interface of the control module 2016 via the detector communication line (Detector Out). The first diode laser may be coupled to an input/output (I/O) interface of the control module 2016 via the first laser control communication line (Laser#1—Control) and coupled to the 16 bit A/D interface of the control module 2016 via the first temperature communication line (Temp #1), and the second diode laser may be coupled to the I/O interface of the control module 2016 via the second laser control communication line (Laser#2—Control) and the 16 bit A/D interface of the control module 2016 via the second temperature communication line (Temp #2).

In addition, FIG. 34 shows that the system controller 1010 is coupled to a user count switch, a program mode switch, a calibration mode switch, a valet mode switch and a display, and the identity board is coupled to a vehicle bus and other vehicle system.

Figure 35:
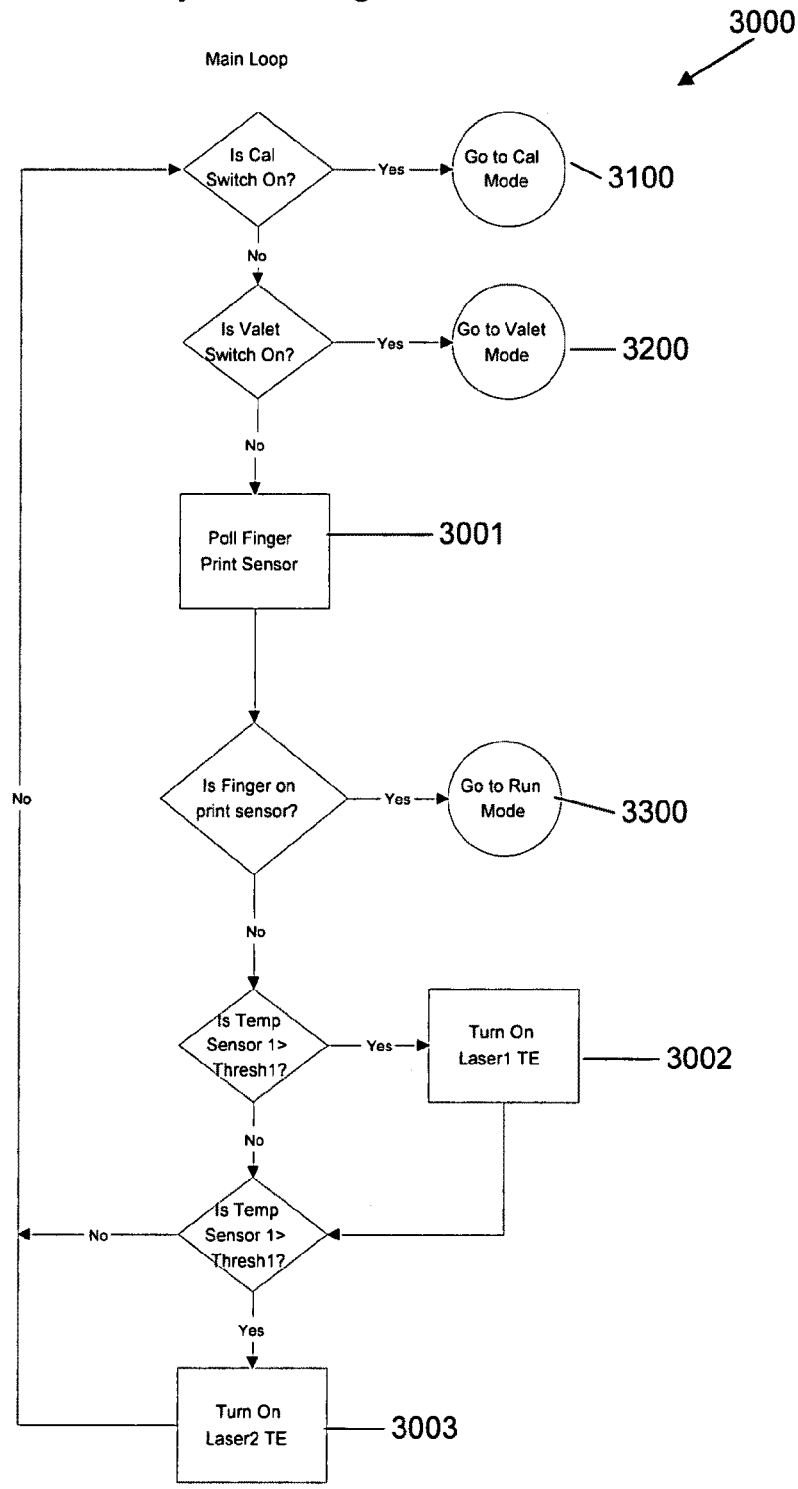
FIGS. 35, 36, 37, and 38 show flowcharts of process blocks of system logics for controlling a vehicle given to a third party, for in-vivo measurement of a concentration of a substance in a tissue of a person, and/or for preventing use of a vehicle by an operator of the vehicle pursuant to aspects of an embodiment of the present invention.
Figure 36:
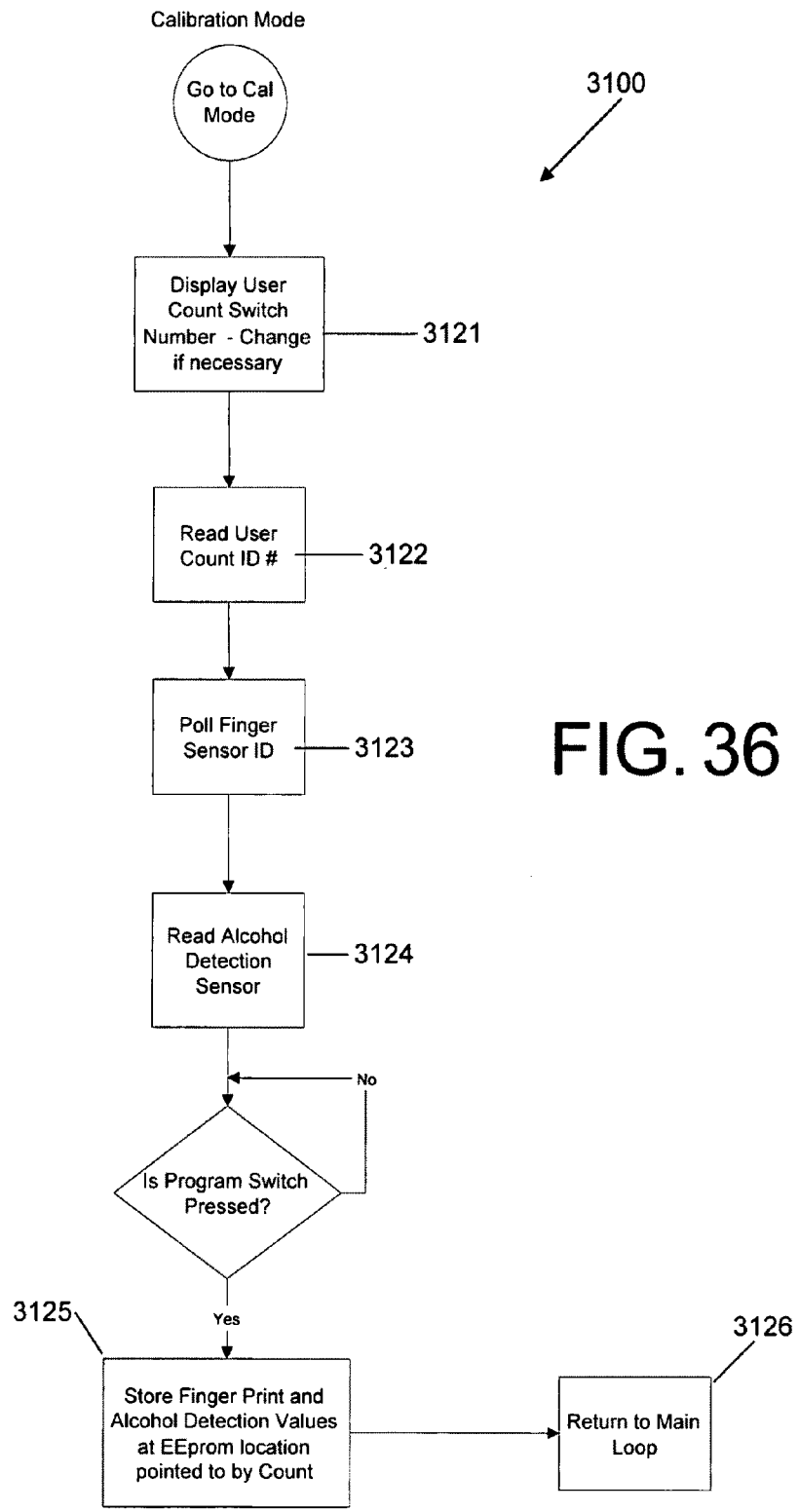

FIGS. 35, 36, 37, and 38 show flowcharts of process blocks of system logics for controlling a vehicle given to a third party, for in-vivo measurement of a concentration of a substance in a tissue of a person, and/or for preventing use of a vehicle by an operator of the vehicle according to certain embodiments of the present invention. As shown in FIG. 35, the system logics has a main loop 3000 that can be operating either in a calibration mode 3100, a run mode 3300, or a valet mode 3200. As shown in the main loop 3000 of FIG. 35, the system logics determine if a calibration switch is turned on. As shown in FIGS. 35 and 36, if the calibration switch is turned on, the system logics go into the calibration mode 3100 by first displaying user count switch number (that may change) in block 3121. Referring to FIG. 36, in block 3122, the system logics read user count identification number. In block 3123, the system logics poll finger sensor identification. In block 3124, the system logics read alcohol detection sensor. The system logics then determine if a program switch has been pressed. If the program switch has been pressed, the system logics store the fingerprint and alcohol detection values at a persistent memory location (e.g., EEprom location) pointed to by the count reading in block 3125, and return to the main loop 3000 in blocks 3126.

Figure 37:
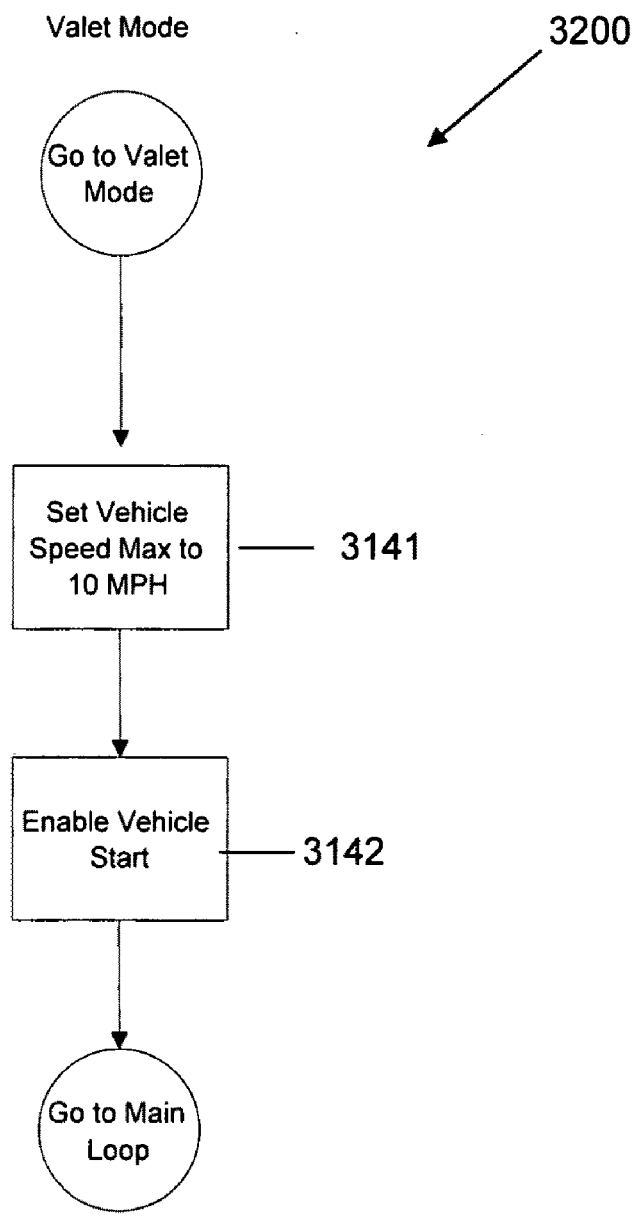

Referring back to FIG. 35, in the main loop 3000, if the calibration switch is not turned on, the system logics then determine if a valet switch is turned on. As shown in FIGS. 35 and 37, if the valet switch is turned on, the system logics go into the valet mode 3200 by setting the vehicle's maximum speed to 10 miles per hour (MPH) in block 3141, enabling the vehicle to start in block 3142, and returning to the main loop 3000.

Figure 38:
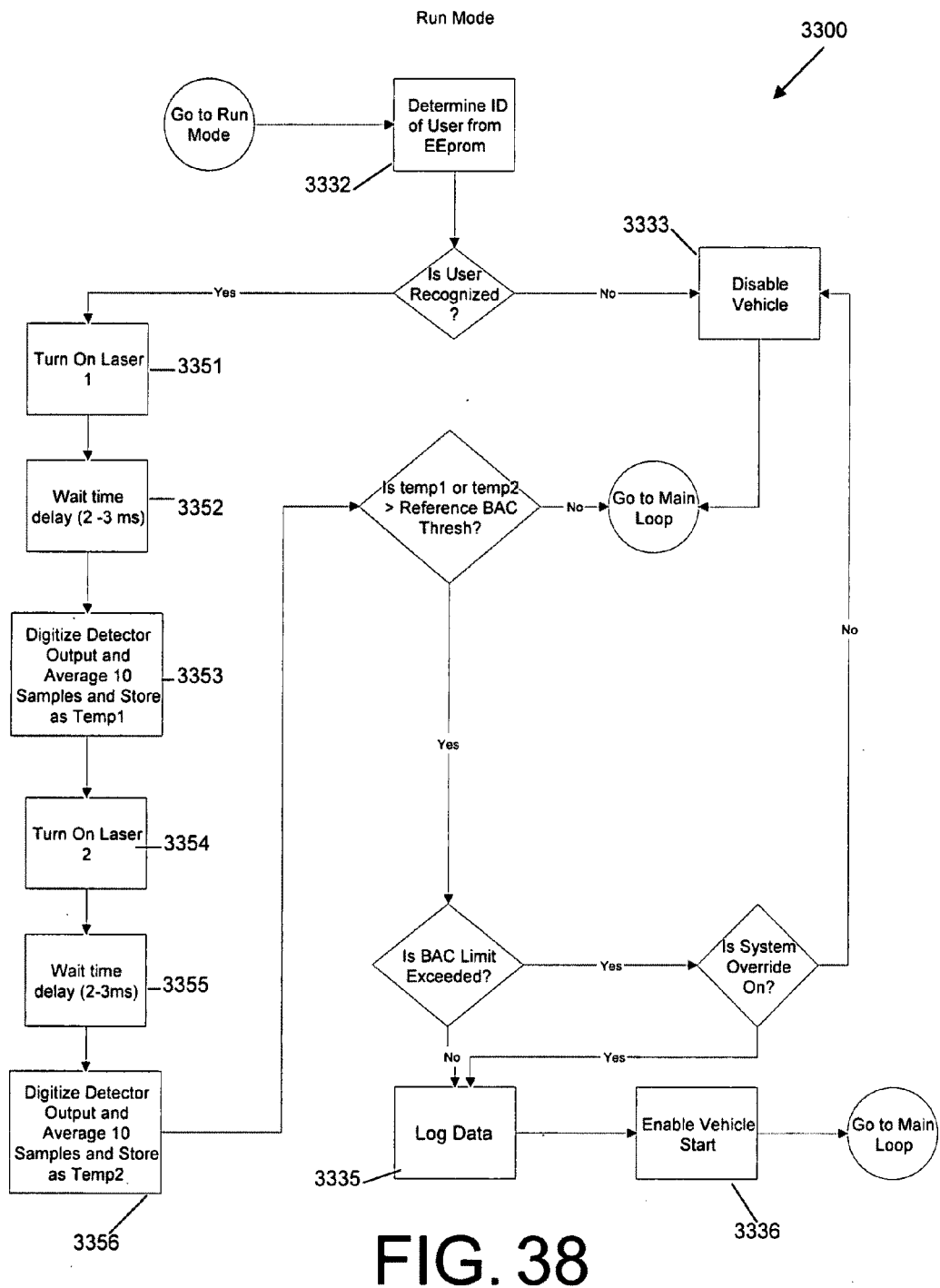

Referring back to FIG. 35, in the main loop 3000, if the valet switch is not turned on, the system logics then poll the fingerprint sensor in block 3001 and determine if the finger is on the fingerprint sensor. Referring to FIGS. 35 and 38, if the finger of the user is on the fingerprint sensor, the system logics determine identification of the user from the persistent memory in block 3332.

The system logics then determine if the user is recognized. If the user is not recognized, the system logics disable the vehicle in block 3333. If the user is recognized, the logics start alcohol detection. That is, the system logics turn on a first laser in block 3351, provide a wait time delay (e.g., from about 2 to about 3 ms) in block 3352. In block 3353, the system logics then digitize the detector output sample, and average several samples (e.g., about 10 samples) to store this average first laser value. In addition, as shown in FIG. 38, the system logics turn on a second laser in block 3354, provide a wait time delay (e.g., from about 2 to about 3 ms) in block 3355. In block 3356, the system logics then digitize the detector output sample, and average several samples (e.g., about 10 samples) to store this average second laser value.

Then, as shown in FIG. 38, the system logic determine if the first laser value or the second laser value is greater than a BAC threshold(s). If the BAC threshold(s) is not exceeded, the system logics then return to the main loop 3000. If the BAC threshold(s) is exceeded, the system logics then determined if the BAC limit is exceeded. If the BAC limit is exceeded, the system logics determine if the system override is on. If the system override is not on, the system logics move to block 3333 to disable the vehicle. By contrast, if the system override is on or the BAC limit has not been exceeded, the system logics log this data in block 3335, enable the vehicle to start in block 3336, and return to the main loop 3000.

Referring back to FIG. 35, in the main loop 3000, if the finger is not on the fingerprint sensor, the system logics then determine if a value from a temperature sensor of the first laser is greater than a first threshold. If the value is greater than the first threshold, the system logics turn on a first laser TEC to cool the first laser. If the value is not greater than the first threshold, the system logics then determine if a value from a temperature sensor of the second laser is greater than a second threshold. If the value is greater than the second threshold, the system logics turn on a second laser TEC to cool the second laser. If the value is not greater than the second threshold, return back to the starting point of the main loop 3000.

In view of the foregoing, embodiments of the present inventions provide a light source at a specific wavelength band for non-invasive and/or in-vivo testing of a concentration of a substance in a tissue of a person; provide two or more specific wavelength bands for non-invasive and/or in-vivo substance analysis; provide a base reading and a later reading for comparison and/or determination of a concentration of a substance in a tissue of a person; couple a biometric sensor with a substance sensor at close proximate locations for concurrent and/or substantial simultaneous authentication and substance evaluation; and/or provide a method and system for controlling a vehicle given to a third party (e.g., a valet). In one embodiment of the present invention, an optical substance detector includes a light source (e.g., a halogen lamp) and a fiber optic bundle attached to the halogen lamp to illuminate a test sample (e.g., an area of the test sample) with a configured wavelength filtering system. The desired wavelength bands are reflected back to a detector. Through an evaluation involving a statistical modeling analysis, the test sample's blood alcohol concentration (BAC) is determined with respect to a legal limit to operate an vehicle and, if the BAC is not within the legal limit, the vehicle is disabled.

It should be appreciated from the above that the various structures and functions described herein may be incorporated into a variety of apparatuses (e.g., an imaging device, a monitoring device, etc.) and implemented in a variety of ways. Different embodiments of the imaging and/or monitoring devices may include a variety of hardware and software processing components. In some embodiments, hardware components such as processors, controllers, state machines and/or logic may be used to implement the described components or circuits. In some embodiments, code such as software or firmware executing on one or more processing devices may be used to implement one or more of the described operations or components.

While the present invention has been described in connection with certain exemplary embodiments, it is to be understood that the invention is not limited to the disclosed embodiments, but, on the contrary, is intended to cover various modifications and equivalent arrangements included within the spirit and scope of the appended claims, and equivalents thereof.

What is claimed is:

1. A system for controlling a vehicle given to a third party, the system comprising:
   a system controller;
   a mode-indicating device coupled to the system controller; and
   a biometric authenticator coupled to the system controller, the biometric authenticator adapted to detect at least one biometric parameter at a first dermal location of an operator of the vehicle,
   a substance detecting device coupled to the system controller and adapted to provide a substance level to the system controller, the substance detecting device adapted to detect a level of a substance in an operator of the vehicle at a second dermal location proximate to the first dermal location,
   wherein the system controller is adapted to communicate a driving restriction to the vehicle upon an activation of the mode-indicating device by an authorized driver, as determined by the biometric authenticator, and until a deactivation of the mode-indicating device by the authorized driver, wherein the system controller is adapted to restrict the activation of the mode-indicating device unless the authorized driver has been authenticated by the biometric authenticator, wherein the system controller is adapted to restrict the deactivation of the mode-indicating device unless the authorized driver has been authenticated by the biometric authenticator and the substance level in the authorized driver, as determined by the substance detecting device, is not above a tolerance level, and wherein the driving restriction comprises a limit selected from the group consisting of a limit in number of starts, a limit in speed, a limit in acceleration, a limit in number of minutes, a limit in distance, a limit in gears, a limit in locations, and combinations thereof.

2. The system of claim 1, wherein the system controller is further adapted to communicate with the vehicle to permit the vehicle to start if the substance level in the third party is not above a tolerance level.

3. The system of claim 2, wherein the system controller is further adapted to communicate another driving restriction to the vehicle if the substance level in the third party is above the tolerance level.

4. The system of claim 3, wherein the driving restriction comprises a command adapted to be sent via a vehicle bus of the vehicle to limit a maximum speed of the vehicle, and wherein the another driving restriction comprises a command adapted to be sent via the vehicle bus of the vehicle to block the vehicle from starting.

5. The system of claim 1, wherein the substance detecting device comprises an optical detector.

6. The system of claim 5, wherein the substance detecting device further comprises a light source configured to direct a first light beam at a specific wavelength band toward the second dermal location, wherein the optical detector is positioned to detect a resulting light beam from the interaction of the first light beam with the second dermal location.

7. The system of claim 6, wherein the specific wavelength band is within a range from about 1300 nm to about 2400 nm.

8. The system of claim 7, wherein the range is selected from the group consisting of a first range from about 1400 nm to about 1500 nm, a second range from about 1650 nm to about 1750 nm, and a third range from about 2200 nm to about 2400 nm.

9. The system of claim 6, wherein the specific wavelength band is at about 1450 nm.

10. The system of claim 6, wherein the optical detector is selected from the group consisting of a single detector, a plurality of detectors and a detector array.

11. The system of claim 10, wherein the optical detector is an InGaAs detector.

12. The system of claim 1, wherein the substance detecting device comprises an optical detector, a first light beam at a first specific wavelength band directed toward the second dermal location, and a second light beam at a second specific wavelength band directed toward the second dermal location and wherein the optical band detector is positioned to detect a resulting light beam from the interaction of the first light beam and the second light beam with the second dermal location.

13. The system of claim 12, wherein the first specific wavelength band is at a wavelength where ethanol is less absorptive than water and the second specific wavelength band is at a wavelength where ethanol is more absorptive than water.

14. The system of claim 12, wherein the optical detector is selected from the group consisting of a single detector, a plurality of detectors and a detector array.

15. The system of claim 14, wherein the optical detector is an InGaAs detector.

16. The system of claim 12, wherein the first specific wavelength band is within a range from about 1400 nm to about 1500 nm and the second specific wavelength band is within a range from about 1650 nm to about 1750 nm.

17. The system of claim 12, wherein the first specific wavelength band is within a range from about 1400 nm to about 1500 nm and the second specific wavelength band is within a range from about 2200 nm to about 2400 nm.

18. The system of claim 1, wherein the substance detecting device comprises an optical detector, a first light beam at a first specific wavelength band directed toward the second dermal location broadband detector, a second light beam at a second specific wavelength band directed toward the second dermal location, and a third light beam at a third specific wavelength band directed toward the second dermal location and wherein the optical detector is positioned to detect a resulting light beam from the interaction of the first, second and third light beams with the second dermal location.

19. The system of claim 18, wherein the optical detector is selected from the group consisting of a single detector, a plurality of detectors and a detector array.

20. The system of claim 18, wherein the first specific wavelength band is within a range from about 1400 nm to about 1500 nm, the second specific wavelength band is within a range from about 1650 nm to about 1750 nm, and the third specific wavelength band is within a range from about 2200 nm to about 2400 nm.

21. The system of claim 20, wherein the first specific wavelength band is at about 1450 nm.

22. The system of claim 18, further comprising a light source configured to provide the first, second, and third light beams.

23. The system of claim 22 further comprising a filtering system disposed between the light source and the optical detector and adapted to provide the first, second, and third light beams at the first, second, and third specific wavelength bands.

24. The system of claim 1, wherein the substance detecting device comprises an optical detector selected from the group consisting of a PbS detector, a PbSe detector, an InAs detector, an InGaAs detector, an InSb detector, and a HgCdTe detector and a light source adapted to direct a first light beam at a specific wavelength to the second dermal location, and wherein the optical detector is positioned to detect a resulting light beam from the interaction of the first light beam with the second dermal location.

25. The system of claim 24, further comprising a wavelength filtering system disposed between the light source and the optical detector and adapted to provide the light beam at the specific wavelength band.

26. The system of claim 25, wherein the wavelength filtering system is disposed closer in distance to the optical detector than to the light source.

27. The system of claim 25, further comprising a platform coupled to both the light source and the optical detector, wherein the platform is configured to contact a surface of the extremity of the operator and has an index of refraction substantially equal to that of the surface of extremity of the operator.

28. The system of claim 1, wherein the substance detecting device comprises an optical detector, and a diode laser configured to direct a first light beam at a specific wavelength toward the second dermal location, and wherein the optical detector is positioned to detect a resulting light beam from the interaction of the first light beam with the second dermal location.

29. The system of claim 28, wherein the specific wavelength is at about 1310 nm.

30. The system of claim 29, wherein the optical detector is a single photodiode detector.

31. The system of claim 1, wherein the substance detecting device comprises an optical detector, a first diode laser configured to direct a first light beam at a first specific wavelength toward the second dermal location, and a second diode laser configured to direct a second light beam at a second specific wavelength toward the second dermal location, and wherein the optical detector is positioned to detect a resulting light beam from the interaction of the first and second light beams with the second dermal location.

32. The system of claim 31, wherein the first specific wavelength is at a wavelength where ethanol is less absorptive than water and the second specific wavelength is at a wavelength where ethanol is more absorptive than water.

33. The system of claim 1, wherein the substance detecting device comprises an optical detector, a first diode laser configured to direct a first light beam at a first specific wavelength toward the second dermal location, a second diode laser configured to direct a second light beam at a second specific wavelength toward the second dermal location, and a third diode laser configured to direct a third light beam at a third specific wavelength toward the second dermal location, and wherein the optical detector is positioned to detect a resulting light beam from the interaction of the first, second and third light beams with the second dermal location.

34. The system of claim 1, wherein the driving restriction further comprises another limit selected from the group consisting of a limit in activatable accessories, a limit in openable compartments, and combinations thereof.

35. The system of claim 34, wherein the system controller is further adapted to send a message to a cell phone if the limit has been exceeded to notify a designated individual remotely.

36. The system of claim 35, wherein the system controller is further adapted to create an alert if the limit has been exceeded to notify the authorized driver when the authorized driver retakes control of the vehicle.

37. The system of claim 1, wherein the third party is a valet.

38. The system of claim 1 wherein the substance detecting device comprises a wide band light source and a spectroscopic evaluation device selected from the group consisting of a dispersive spectrometer, a filtering spectrometer, a single or multiple slit monochrometer and a scanning slit monochrometer, to detect the level of a substance in an operator of a vehicle.

39. The system of claim 1 wherein the substance detecting device comprises a single or multiple narrow band light source, and single or multiple optical detectors.

* * * * *

UNITED STATES PATENT AND TRADEMARK OFFICE
CERTIFICATE OF CORRECTION

| | | |
|---|---|---|
| PATENT NO. | : 7,812,712 B2 | Page 1 of 1 |
| APPLICATION NO. | : 11/702795 | |
| DATED | : October 12, 2010 | |
| INVENTOR(S) | : Steve C. White et al. | |

It is certified that error appears in the above-identified patent and that said Letters Patent is hereby corrected as shown below:

In the Claims

Column 42, Claim 18, line 19      Delete "broadband detector"

Signed and Sealed this

Thirteenth Day of September, 2011

David J. Kappos
*Director of the United States Patent and Trademark Office*

UNITED STATES PATENT AND TRADEMARK OFFICE
CERTIFICATE OF CORRECTION

PATENT NO. : 7,812,712 B2  Page 1 of 1
APPLICATION NO. : 11/702795
DATED : October 12, 2010
INVENTOR(S) : Steve C. White et al.

It is certified that error appears in the above-identified patent and that said Letters Patent is hereby corrected as shown below:

In the Claims

Column 41, Claim 12, line 62   Delete "band"

Column 42, Claim 18, line 19   Delete "broadband detector"

This certificate supersedes the Certificate of Correction issued September 13, 2011.

Signed and Sealed this
Twenty-second Day of November, 2011

David J. Kappos
*Director of the United States Patent and Trademark Office*